US012280144B2

(12) United States Patent
Yusuf

(10) Patent No.: US 12,280,144 B2
(45) Date of Patent: Apr. 22, 2025

(54) GEL COMPOSITIONS FOR MITIGATION OF BURN INJURIES, KITS CONTAINING THE GEL COMPOSITIONS, AND ASSOCIATED METHODS

(71) Applicant: Zaki Yusuf, Louisville, KY (US)

(72) Inventor: Zaki Yusuf, Louisville, KY (US)

( * ) Notice: Subject to any disclaimer, the term of this patent is extended or adjusted under 35 U.S.C. 154(b) by 748 days.

(21) Appl. No.: 16/951,335

(22) Filed: Nov. 18, 2020

(65) Prior Publication Data

US 2021/0186873 A1    Jun. 24, 2021

Related U.S. Application Data

(60) Provisional application No. 62/950,643, filed on Dec. 19, 2019.

(51) Int. Cl.
| | |
|---|---|
| *A61K 9/06* | (2006.01) |
| *A61K 9/00* | (2006.01) |
| *A61K 9/08* | (2006.01) |
| *A61K 31/045* | (2006.01) |
| *A61K 33/14* | (2006.01) |
| *A61K 47/02* | (2006.01) |
| *A61K 47/12* | (2006.01) |
| *A61K 47/38* | (2006.01) |
| *A61P 17/02* | (2006.01) |

(52) U.S. Cl.
CPC .............. *A61K 9/06* (2013.01); *A61K 9/0014* (2013.01); *A61K 31/045* (2013.01); *A61K 33/14* (2013.01); *A61K 47/02* (2013.01); *A61K 47/12* (2013.01); *A61K 47/38* (2013.01); *A61P 17/02* (2018.01); *A61K 9/08* (2013.01)

(58) Field of Classification Search
None
See application file for complete search history.

(56) References Cited

U.S. PATENT DOCUMENTS

| | | | |
|---|---|---|---|
| 3,993,750 | A | 11/1976 | Fox, Jr. |
| 4,070,289 | A | 1/1978 | Akeasu |
| 4,414,202 | A | 11/1983 | Silvetti |
| 4,548,716 | A | 10/1985 | Boeve |
| 4,732,755 | A | 3/1988 | Grana |
| 5,271,943 | A | 12/1993 | Bogart et al. |
| 5,616,619 | A | 4/1997 | Stofer |
| 6,958,159 | B2 | 10/2005 | Smith |
| 7,705,032 | B2 | 4/2010 | Dittrich |
| 8,741,353 | B1 | 6/2014 | Al-Mutawaa |
| 9,381,214 | B2 | 7/2016 | Sampson et al. |
| 2006/0233783 | A1 | 10/2006 | Gomez Torres |
| 2009/0175926 | A1 | 7/2009 | Adams |
| 2009/0214628 | A1 | 8/2009 | de Rijk |
| 2015/0196585 | A1 | 7/2015 | Young et al. |
| 2017/0087199 | A1 | 3/2017 | Patron et al. |

FOREIGN PATENT DOCUMENTS

| | | |
|---|---|---|
| EP | 2364713 A1 | 9/2011 |
| WO | 2005030168 A1 | 4/2005 |
| WO | 2016111855 A1 | 7/2016 |
| WO | 2019077540 A1 | 4/2019 |

OTHER PUBLICATIONS

Aldana (Abstract for the internet article "Hyperkalemia in electrical burns: A retrospective study in Colombia" Burns, vol. 44(4) (Feb. 2018) obtained from the website: https://www.researchgate.net/publication/322889167_Hyperkalemia_in_electrical_burns_A_retrospective_study_in_Colombia) (Year: 2018).*
Pan, Shin-Chen et al.: "Deep partial thickness burn blister fluid promotes neovascularization in the early stage of burn wound healing by the Wound Healing Society", Wound Rep. Reg. vol. 18, 2010, p. 311-318.
Murphy, J. F., Purdue G. F. and Hunt J. L.: "Acute Adrenal Insufficiency in the Patient With Burns" The Journal of Burn Care & Rehabilitation, vol. 14, No. 2, Mar. 1993, p. 155-157.
Baxter C.: "Fluid and Electrolyte Disorders in the Thermally Injured." Chapter 17, Therapy of Renal Diseases and Related Disorders. Suki W.N., Massry S.G. (eds.) Kluwer Academic Publishers, 1991, p. 277-278.
Niedzwiecki M. M. et al: "Human Suction Blister Fluid Composition Determined Using High-Resolution Metabolomics" Analytical Chemistry, vol. 90, No. 6, 2018p. 3786-3792.
Guilabert, P. et al: "Fluid resuscitation management in patients with burns: Update." British Journal of Anaesthesia, vol. 117, 2016, p. 284-296.
Saffle, J. R.: "The Phenomenon of "Fluid Creep" in Acute Burn Resuscitation" Journal of Burn Care & Research, vol. 28, No. 3, May 2007, p. 382-395.
Pham, T. N. et al: "Burn Shock Resuscitation American Burn Association Practice Guidelines" Journal of Burn Care & Research, vol. 29, No. 1, Jan./Feb. 2008, p. 257-266.

(Continued)

*Primary Examiner* — Sin J Lee
(74) *Attorney, Agent, or Firm* — Richard Joseph McNeely

(57) ABSTRACT

Compositions and methods are provided for treating first, second degree burns to rapidly minimize hyperkalemia, hyponatremia, blistering, and pain management by externally applying gel mixture on unopened injured burn areas from onset of burn shock. The substrate is a gel mixture matrix containing concentrated sodium ion that creates a concentration gradient, allowing in situ diffusion of sodium ion (in vitro) into blister, edema, and extracellular fluids (in vivo) to reduce hyponatremia and (in situ), delivering the pH control constituents in vivo to prevent initial acidosis, followed by minimizing subsequent alkalosis and normalizing SID while simultaneously in situ expelling potassium ions in vitro from the same fluids transdermally while restoring normal homeostasis. The in situ restoration of homeostasis and electrophysiology also brings pain relief and retards transcapillary vascular fluid loss to help defend kidney and cardiac functions by rectifying transmembrane potential across skeletal, neural, cardiac, and renal cell membranes.

5 Claims, 27 Drawing Sheets

(56) References Cited

OTHER PUBLICATIONS

Zeebe R.E.: "On the molecular diffusion coefficients of dissolved CO2; HCO3-, and CO3-2and their dependence on isotopic mass" Geochimica et Cosmochimica Acta, vol. 75, 2011, p. 2483-2498.
Sen, S. et al.: "Sodium variability is associated with increased mortality in severe burn injury" Burns & Trauma, vol. 5, No. 34, 2017, p. 2-6.
Leaist, D. G. et al: "Multicomponent diffusion of aqueous sodium carbonate and aqueous sodium bicarbonate" Can. J. Chem., vol. 63, 1985, p. 2319-2323.
Fried, L. et al: "New options for the management of chronic hyperkalemia" Kidney International Supplements vol. 7, 2017, p. 164-170.
McCullough, P. A. et al: "Acute and Chronic Cardiovascular Effects of Hyperkalemia: New Insights into Prevention and Clinical Management" Reviews in Cardiovascular Medicine vol. 5, 2014.
Sharma,V.: "The rheology of aqueous solutions of ethyl hydroxyethyl cellulose (EHEC) and its hydrophobically modified analogue (hmEHEC): extensional flow response in capillary break-up, jetting (ROJER) and in a cross-slot extensional rheometer" Soft Matter, vol. 11, 2015, p. 3251-3270.
Di Serafino, et al., "Nontraumatic adrenal hemorrhage: the adrenal stress", Radiology Case Reports, vol. 1, No. 2, pp. 483-487, 2017.
Haberal, et al., "Fluid management in major burn injuries", Indian J. Plast Surg., vol. 43 (Suppl), Sep. 2010, S29-S36.
Reiff, D. A. et al: "Risk Factors Associated With Adrenal Insufficiency in Severely Injured Burn Patients" Journal of Burn Care & Research, vol. 28, No. 6, Nov. 2007, p. 854-858.
Volden, G. et al: "Biochemical Composition of Suction Blister Fluid Determined by High Resolution Multicomponent Analysis" (Capillary Gas Chromatography Mass Spectrometry and Two-Dimensional Electrophoresis) The Journal of Investigative Dermatology, vol. 75, No. 5, Nov. 1980, p. 421-424.
Satahoo, et al., "Fluid Resuscitation in Burns: 2 cc, 3 cc, or 4 cc?", Current Trauma Reports, vol. 5, pp. 99-105, 2019.
Cancio, et al., "A history of burn care", Handbook of Burns, pp. 3-280, 2012.
Chan, et al., "Fluid resuscitation in burns: an update", Hong Kong Journal of Emergency Medicine, vol. 16, No. 1, pp. 51-62, Jan. 2009.
Loannovich, et al., "Parkland Formula as a Guide for Resuscitation", Annals of the MBC, vol. 2, No. 1, pp. 1-8, Mar. 1989.
ISBI, "ISBI Practice Guidelines for Burn Care", ScienceDirect, vol. 42, pp. 953-1021, 2016.
Jelenko, et al., "Water Loss from the Body Surface", Studies in Burns, pp. 83-96, Jan. 1967.
Jeschke, et al., "Burn injury" Nature Reviews Primer, vol. 6, No. 1, pp. 1-25, 2020.
Kaddoura, et al., "Burn Injury: Review of Pathophysiology and Therapeutic Modalities in Major Burns", Annals of Burns and Fire Disaster, vol. xxx, No. 2, pp. 1-8, Jun. 2017.
McLaughlin, et al., "Burns Prevention, Causes and Treatment", Surgery—Procedures, Complications, and Results, pp. 1-281, 2012.
Namdar, et al., "Transdermal fluid loss in severely burned patients", Open Access, GMS German Medical Science, vol. 8, pp. 1-5, 2010.
Pan, "Burn blister fluids in the neovascularization stage of burn wound healing: A comparison between superficial and deep partial-thickness burn wounds", Burns & Trauma, vol. 1, Issue 1, pp. 27-31, Jun. 2013.
Bacomo, et al., "A primer on burn resuscitation", Symposium, Journal of Emergencies, Trauma, and Shock I, vol. 4, No. 1, pp. 109-114, 2011.
Sarwar, et al., "Hyperkalemia in Hearty Failure", Journal of the American College of Cardiology, vol. 68, No. 14, pp. 1575-1589, Oct. 4, 2016.
Dobson, et al., "Hyperkalemic cardioplegia for adult and pediatric surgery: end of an era?", Frontiers in Physiology, vol. 4, pp. 1-28, Aug. 2013.
Fried, et al., "New options for the management of chronic hyperkalemia", Kidney International Supplements, vol. 7, pp. 164-170, 2017.
Jeschke, et al., "Long-Term Persistance of the Pathophysiologic Response to Severe Burn Injury", PLOS OneAccess, vol. 6, Issue 7, pp. 1-12, Jul. 2011.
Guilabert, et al., "Fluid resuscitation management in patients with burns: update", British Journal of Anaesthesia, vol. 117, No. 3, pp. 284-296, 2016.
An, et al., "Severe hyperkalemia requiring hospitalization: predictors of mortality", Critical Care, vol. 16, pp. 1-14, 2012.
Ji, et al., "Hypertonic saline soaks in treatment of burned skin", ScienceDirect Burns, pp. 152-153, 2009.
Kara, "Burn Etiology and Pathogenesis", Hot Topic in Burn Injuries, pp. 16-34, 2018.
Khanagavi, et al., "Hyperkalemia among hospitalized patients and association between duration of hyperkalemia and outcomes", Clinical Research, pp. 251-259, Apr. 2014.
Krishnan, et al., "Acute and Chronic Cardiovascular Effects of Hyperkalemia: New Insights Into Prevention and Clinical Management", Reviews in Cardiovascular Medicine, vol. 17, Suppl. 1, pp. S9-S21, 2016.
Lam. et al., "Risk Factors and Outcome of Hypernatremia Amongst Sever Adult Burn Patients", Annals of Burns and Fire Disasters, vol. XXXI, No. 4, pp. 271-277, Dec. 2018.
Mitchell, et al., "New Management Strategy for Fluid Resuscitation: Quantifying vol. in the First 48 Hours After Burn Injury". Journal of Burn Care & Research, vol. 34, No. 1, pp. 196-202, 2013.
Pham, et al., "American Burn Association Practice Guidelines Burn Shock Resuscitation", Journal of Burn Care & Research, pp. 257-266, 2008.
Saffle, "Telemdeicine for acute burn treatment: the time has come", Journal of Telemedicine and Telecare, vol. 12, pp. 1-3, 2006.
Saffle, "Protective Ventilation for Patients with Acute Respiratory Distress Syndrome", New England Journal of Medicine, vol. 338, No. 6, pp. 385-389, Feb. 5, 1998.
Saline, "ISBI Practice Guidelines for Burn Care", ScienceDirect Burns, vol. 42, pp. 953-1021, 2016.
Sojka, et al., "Burn Shock and resuscitation: Many Priorities, One Goal", Clinical Management of Shock, pp. 1-36, 2019.
Summer, et al., "Burn Injury Pain: The Continuing Challenge", The Journal of Pain, vol. 8, No. 7, pp. 533-548, Jul. 2007.
Zeebe, "On the molecular diffusion coefficients of dissolved $CO_2$, $HCO_3$, and $CO^{2/3}$—and their dependence on isotopic mass", ScienceDirect, vol. 75, pp. 2483-2498, 2011.
Pham, et al., "American Burn Association Practice Guidelines Burn Shock Resuscitation", Journal of Burn Care & Research, pp. 256-266, 2008.
Sigel, et al., "Interrelations between Essential Metal Ions and Human Diseases", Metal Ions in Life Sciences 13, vol. 13, pp. 1-603, 2005.

* cited by examiner

| Ion Type | Conc. mEq/L | Cell |
|---|---|---|
| Na⁺ | ~ 140 | ~ 12 mEq/L |
| K⁺ | ~ 4 | ~ 140 mEq/L |
| Ca²⁺ | ~ 2 | ~ 10⁻⁴ mEq/L |

$7.35 \geq pH \geq 7.45$

Extracellular Fluid

Typical intracellular ion concentrations versus extracellular fluids/plasma ion concentrations

FIG. 1

Action Potentials (Depolarization, Repolarization and Hyperpolarization) of Neuron

| Ion Type | Conc. mEq/L | Cell |
|---|---|---|
| $Na^+$ | ≤135 | ≥ 12 mEq/L |
| $K^+$ | ≥ 5.5 | ≤ 135 mEq/L |
| $Ca^{2+}$ | ~ 1 | ~ $10^{-4}$ mEq/L | pH≤7.35 (Acidosis)

Local Blister Fluid (After Burn Shock)

An example of severely burn injured patient's intracellular cell ion concentration with initial acidosis and hyperkalemia versus extracellular fluids/plasma ion concentrations

FIG. 3

Burn Shock Flowchart with Hyperkalemia and Hyponatremia
in Extracellular and Intravascular Fluids

| Ion Type | Local Conc. mEq/L | Cell |
|---|---|---|
| $Na^+$ | ≤135 | ≥ 12 mEq/L |
| $K^+$ | ≥ 70 | ≤ 135 mEq/L |
| $Ca^{2+}$ | ~ 1 | ~ $10^{-4}$ mEq/L | pH≥7.45 (Alkalosis)

Local Blister Fluid (After Burn Shock)

An example of severely burn injured patient's intracellular cell ion concentration with subsequent local alkalosis and local hyperkalemia in extracellular fluids/plasma ion concentrations

FIG. 5

Post Admission Percent Death and Ventricular
Fibrillation or Cardiac Arrest versus Serum
Potassium ($K^+$) Ion

Extracellular concentrations of potassium ($K_e^+$) results in the classic electrocardiographic changes

This figure exemplifies the local surge in extracellular/blister potassium ($K_e^+$) ion concentration which eventually disperses across the vast network of the vast network of the circulatory system over time, thus raising the overall extracellular potassium ($K_e^+$) ion concentration over 5.5 mEq/L once dispersed for a severely burned patient.

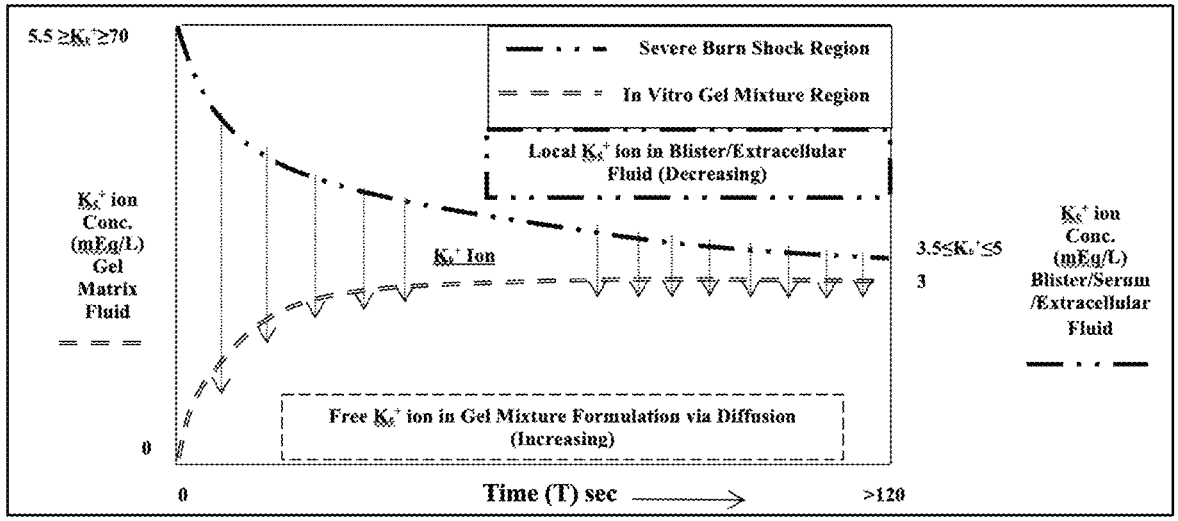

A qualitative example of excessively high extracellular local potassium ($K_e^+$) ion surge and their expulsion through transdermal route outside to the gel mixture matrix (*in vitro*) with multiple consecutive replacement of freshly applied gel mixture formulation in order to rapidly remove the locally accumulated potassium ($K_e^+$) ions before they disperse into the vast network of the circulatory system

FIG. 9

Simplified Schematics of Intricate Network of Human Circulatory System

The severe changes in the electrocardiogram is observed when the case hyperkalemia becomes very pronounced Sodium (Na⁺) ions in extracellular fluid or plasma is balanced by chloride (Cl⁻) ions and other anions, *viz.*, bicarbonate ($HCO_3^-$), lactate, charged proteins (amino acid anions) etc. Here, excess chloride (Cl⁻) ion increase leads to hyperchloremia leading to undesirable acidosis Example of Counter Diffusional Mass Transfer of Sodium ($Na^+$) and Local Extracellular/Blister Potassium ($K_e^+$) Ions across the Transdermal Barrier with Initial Acidosis at the onset of Burn Shock ($T \approx 0$)

Example of Counter Diffusional Mass Transfer of Sodium ($Na^+$) and Local Extracellular/Blister Potassium ($K_e^+$) Ions across the Transdermal Barrier with Initial Acidosis at (T>0) and subsequent pH Balance Example of Sodium (Na⁺) and Local Extracellular/Blister Potassium ($K_e^+$) Ion Concentration across the Transdermal Barrier with Initial Acidosis (at T≫0)

Example of Counter Diffusional Mass Transfer of Sodium ($Na^+$) and Local Extracellular/Blister Potassium ($K_e^+$) Ions across the Transdermal Barrier with Alkalosis at the onset of Burn Shock ($T \approx 0$)

Example of Counter Diffusional Mass Transfer of Sodium ($Na^+$) and Local Extracellular/Blister Potassium ($K_e^+$) Ions across the Transdermal Barrier with Alkalosis (at T>0) and Subsequent pH Rectification Example of Counter Diffusional Mass Transfer of Sodium ($Na^+$) and Local Extracellular/Blister Potassium ($K_e^+$) Ions across the Transdermal Barrier with Alkalosis (at T≫0) and subsequent pH Rectification

| Ingredients gm(s) in 1 Liter | Example 1 | Example 2 | Example 3 | Example 4 | Example 5 | Example 6 | Example 7 | Example 8 | Example 9 | Example 10 |
|---|---|---|---|---|---|---|---|---|---|---|
| DI Water (gm) | 1000 | 1000 | 1000 | 1000 | 1000 | 1000 | 1000 | 1000 | 1000 | 1000 |
| Sodium Chloride (gm) | 300 | 300 | 300 | 300 | 300 | 300 | 300 | 300 | 300 | 300 |
| Sodium Bicarbonate (gm) | 17.69 | 0.35 | 0.126 | 0.0378 | 0.0038 | 0.00168 | 0.00109 | 0.35 | 0.126 | 0.0378 |
| Sodium Carbonate | 17.93 | | | | | | | | | |
| Sodium Lactate (gm) | 156.00 | 156.00 | 44.80 | 14.50 | 14.30 | 8.69 | 8.39 | 156.00 | 44.80 | 14.50 |
| Sodium Acetate (gm) | 82.00 | 8.20 | 4.40 | 3.70 | | 0.16 | 0.05 | 8.20 | 4.40 | 3.70 |
| Trisodium Citrate (gm) | 420.00 | 420.00 | 36.00 | 42.80 | | 25.80 | 9.00 | 420.00 | 26.00 | 42.80 |
| Lactic Acid (gm) | | | | | | | | | | |
| Citric Acid (gm) | | | | | | | | | | |
| Acetic Acid (gm) | | | | | | | | | | |
| Gelling Agent (gm) | Hydroxy Ethyl Cellulose | Hydroxy Ethyl Cellulose | Hydroxy Ethyl Cellulose | Hydroxy Ethyl Cellulose | Hydroxy Ethyl Cellulose | Hydroxy Ethyl Cellulose | Hydroxy Ethyl Cellulose | Hydroxy Ethyl Cellulose | Hydroxy Ethyl Cellulose | Hydroxy Ethyl Cellulose |
| | Oligomers of Cellulose | Oligomers of Cellulose | Oligomers of Cellulose | Oligomers of Cellulose | Oligomers of Cellulose | Oligomers of Cellulose | Oligomers of Cellulose | Oligomers of Cellulose | Oligomers of Cellulose | Oligomers of Cellulose |
| | Pectin | Pectin | Pectin | Pectin | Pectin | Pectin | Pectin | Pectin | Pectin | Pectin |
| | Carboxy Methyl Cellulose | Carboxy Methyl Cellulose | Carboxy Methyl Cellulose | Carboxy Methyl Cellulose | Carboxy Methyl Cellulose | Carboxy Methyl Cellulose | Carboxy Methyl Cellulose | Carboxy Methyl Cellulose | Carboxy Methyl Cellulose | Carboxy Methyl Cellulose |
| | Guar Gum | Guar Gum | Guar Gum | Guar Gum | Guar Gum | Guar Gum | Guar Gum | Guar Gum | Guar Gum | Guar Gum |
| | Gum Arabic | Gum Arabic | Gum Arabic | Gum Arabic | Gum Arabic | Gum Arabic | Gum Arabic | Gum Arabic | Gum Arabic | Gum Arabic |
| Greater Than or Equal to gm | 100.18 | 94.23 | 63.77 | 63.01 | 65.73 | 66.29 | 65.47 | 89.23 | 63.77 | 53.01 |
| Sodium Polyacrylate (ppm) | ≤300 | ≤300 | ≤300 | ≤300 | ≤300 | ≤300 | ≤300 | ≤300 | ≤300 | ≤300 |
| Polyacrylic acid (ppm) | | | | | | | | | | |
| Sodium Polystyrene Sulfonate (Na-PSS; Kayexalate) ppm | ≤300 | ≤300 | ≤300 | ≤300 | ≤300 | ≤300 | ≤300 | ≤300 | ≤300 | ≤300 |
| Total (gm) | 2103.80 | 1978.93 | 1444.09 | 1428.25 | 1389.23 | 1392.14 | 1374.91 | 1873.93 | 1339.99 | 1218.25 |
| Properties | P (Buffered) | R | Q | P | E | R | T | E | U | S |
| pH | 10 | 9.00 | 8.75 | 8.50 | 8.50 | 8.00 | 7.70 | 9.00 | 8.75 | 8.50 |
| Viscosity of Gel Mixture mm2/s(cP) at (-20 °C) | 100-150,000 | 100-150,000 | 100-150,000 | 100-150,000 | 100-150,000 | 100-150,000 | 100-150,000 | 100-150,000 | 100-150,000 | 100-150,000 |
| Injury Type | Severe & Deep | Severe & Deep | Severe & Deep | Severe & Deep | Severe | Severe | Mild | Severe & Deep | Severe & Deep | Severe & Deep |
| Time of Application | Immediately | Immediately | Immediately | Immediately | Immediately | Immediately | Immediately | Immediately | Immediately | Immediately |
| Type of Patient | Normal | Normal | Normal | Normal | Normal | Normal | Normal | Normal | Normal | Normal |
| Physiological pH Condition | Acidosis | Acidosis | Acidosis | Acidosis | Acidosis | Acidosis | Acidosis | Acidosis | Acidosis | Acidosis |
| Total Injured Burn Area (%) | ≥10-20 | ≥20 | ≥10-20 | ≥10-20 | ≥20 | ≥20 | ≤10 | ≥20 | ≥10-20 | ≥10-20 |

FIG. 21

| Ingredients gm(s) in 1 Liter | Example 11 | Example 12 | Example 13 | Formulation (B) (Alkalosis Condition) Example 14 | Example 15 | Example 16 | Example 17 | Example 18 | Example 19 | Example 20 |
|---|---|---|---|---|---|---|---|---|---|---|
| DI Water (gm) | 1000 | 1000 | 1000 | 1000 | 1000 | 1000 | 1000 | 1000 | 1000 | 1000 |
| Sodium Chloride (gm) | 90 | 90 | 90 | 90 | 90 | 300 | 90 | 90 | 90 | 250 |
| Sodium Bicarbonate (gm) | - | - | - | - | - | - | - | - | - | - |
| Sodium Carbonate | - | - | - | - | - | - | - | - | - | - |
| Sodium Lactate (gm) | 12.30 | 12.30 | 12.30 | 12.30 | 302.08 | 12.60 | 342.88 | 12.80 | 12.60 | 12.60 |
| Sodium Acetate (gm) | - | - | - | - | - | 35.71 | - | - | - | 35.71 |
| Trisodium Citrate (gm) | - | - | - | - | - | 937 | 374 | - | - | 937 |
| Lactic Acid (gm) | 0.0618 | 0.0203 | 0.0625 | 0.0618 | 0.2790 | 0.0823 | 0.63 | 0.0203 | 0.0823 | 0.0828 |
| Citric Acid (gm) | - | - | - | - | - | 0.192 | 0.077 | - | - | 0.192 |
| Acetic Acid (gm) | - | - | - | - | - | 0.3 | - | - | - | 0.3 |
| Gelling Agent (gm) | Hydroxy Ethyl Cellulose Oligomers of Cellulose Pectin Carboxy-Methyl Cellulose Guar Gum Gum Arabic | Hydroxy Ethyl Cellulose Oligomers of Cellulose Pectin Carboxy-Methyl Cellulose Guar Gum Gum Arabic | Hydroxy Ethyl Cellulose Oligomers of Cellulose Pectin Carboxy-Methyl Cellulose Guar Gum Gum Arabic | Hydroxy Ethyl Cellulose Oligomers of Cellulose Pectin Carboxy-Methyl Cellulose Guar Gum Gum Arabic | Hydroxy Ethyl Cellulose Oligomers of Cellulose Pectin Carboxy-Methyl Cellulose Guar Gum Gum Arabic | Hydroxy Ethyl Cellulose Oligomers of Cellulose Pectin Carboxy-Methyl Cellulose Guar Gum Gum Arabic | Hydroxy Ethyl Cellulose Oligomers of Cellulose Pectin Carboxy-Methyl Cellulose Guar Gum Gum Arabic | Hydroxy Ethyl Cellulose Oligomers of Cellulose Pectin Carboxy-Methyl Cellulose Guar Gum Gum Arabic | Hydroxy Ethyl Cellulose Oligomers of Cellulose Pectin Carboxy-Methyl Cellulose Guar Gum Gum Arabic | Hydroxy Ethyl Cellulose Oligomers of Cellulose Pectin Carboxy-Methyl Cellulose Guar Gum Gum Arabic |
| Greater Than or Equal to gm | 54.64509 | 54.641015 | 54.63814 | 54.64509 | 69.11395 | 114.29824 | 99.85535 | 54.641015 | 54.63814 | 111.79324 |
| Sodium Polyacrylate (ppm) | ≤300 | - | ≤300 | - | - | - | - | - | ≤300 | - |
| Polyacrylic acid (ppm) | - | - | ≤300 | - | - | - | - | - | ≤300 | - |
| Sodium Polystyrene Sulfonate (Na-PSS; Kayexalate) ppm | - | - | ≤300 | - | - | - | ≤300 | - | ≤300 | ≤300 |
| Total (gm) | 1148 | 1147 | 1147 | 1148 | 1451 | 2488 | 2097 | 1147 | 1147 | 2348 |
| Properties | P | R | Q | P | E | R | T | L | E | S |
| pH | 6.9 (Buffered) | 6.8 (Buffered) | 6.7 (Buffered) | 6.9 (Buffered) | 6.8 (Buffered) | 6.7 (Buffered) | 6.7 (Buffered) | 6.8 (Buffered) | 6.7 (Buffered) | 6.7 (Buffered) |
| Viscosity of Gel Mixture sm².s(cP) at (-20 °C) | 100-150,000 | 100-150,000 | 100-150,000 | 100-150,000 | 100-150,000 | 100-150,000 | 100-150,000 | 100-150,000 | 100-150,000 | 100-150,000 |
| For Injury Type | Severe | Severe & Deep | Severe & Deep | Severe | Severe & Deep | Severe & Deep | Severe & Deep | Severe & Deep | Severe & Deep | Severe & Deep |
| Time of Application | Delayed | Delayed | Delayed | Delayed | Delayed | Delayed | Delayed | Delayed | Delayed | Delayed |
| Type of Patient | Alkalosis Patient | Alkalosis Patient | Alkalosis Patient | Alkalosis Patient | Alkalosis Patient | Alkalosis Patient | Alkalosis Patient | Alkalosis Patient | Alkalosis Patient | Alkalosis Patient |
| Physiological pH Condition | Alkalosis | Alkalosis | Alkalosis | Alkalosis | Alkalosis | Alkalosis | Alkalosis | Alkalosis | Alkalosis | Alkalosis |
| Total Injured Burn Area (%) | ≥20 | ≥20 | ≥20 | ≥20 | ≥20 | ≥20 | ≥20 | ≥20 | ≥20 | ≥20 |

| Ingredients (wt%) | Formulation (I) Acidosis Condition | | | | | | |
|---|---|---|---|---|---|---|---|
| | Example 1 | Example 2 | Example 3 | Example 4 | Example 5 | Example 6 | Example 7 |
| Sterile DI Water (gm) | 1000 | 1000 | 1000 | 1000 | 1000 | 1000 | 1000 |
| (H2O) (%) | 86.92 | 86.93 | 86.95 | 86.92 | 68.73 | 46.80 | 58.74 |
| Sodium Chloride (gm) (NaCl) (%) | 80 / 6.95 | 80 / 6.95 | 80 / 6.96 | 80 / 6.95 | 80 / 5.50 | 80 / 3.74 | 80 / 4.68 |
| Sodium Bicarbonate (gm) (NaHCO3) (%) | - | - | - | - | - | - | - |
| Sodium Carbonate and (NaHCO3) Buffer (%) | - | - | - | - | - | - | - |
| Sodium Lactate (gm) (C3H5O3Na) (%) | 12.90 / 1.12 | 12.80 / 1.11 | 12.60 / 1.10 | 12.99 / 1.12 | 303.08 / 20.76 | 12.66 / 0.59 | 342.08 / 31.73 |
| Sodium Acetate (gm) (CH3COONa) (%) | - | - | - | - | - | - | - |
| Trisodium Citrate (gm) (C6H5O7·3Na) (%) | - | - | - | - | - | 937 / 43.85 | 374 / 17.79 |
| Lactic Acid (gm) (CH3CH(OH)COOH) (%) | 0.0018 / 0.0002 | 0.0203 / 0.0018 | 0.0028 / 0.0002 | 0.0018 / 0.0002 | 0.2798 / 0.0192 | 0.0028 / 0.0001 | 0.63 / 0.0369 |
| Citric Acid (gm) (C6H8O7) (%) | - | - | - | - | - | 0.001133 | 0.877 / 0.0368x3 |
| Acetic Acid (gm) (CH3COOH) (%) | - | - | - | - | - | - | - |
| Gelling Agent (gm) | Hydroxy Ethyl Cellulose / Carboxy Methyl Cellulose / Oligomers of Cellulose / Pectin / Guar Gum / Gum Arabic ≥5 | Hydroxy Ethyl Cellulose / Carboxy Methyl Cellulose / Oligomers of Cellulose / Pectin / Guar Gum / Gum Arabic ≥5 | Hydroxy Ethyl Cellulose / Carboxy Methyl Cellulose / Oligomers of Cellulose / Pectin / Guar Gum / Gum Arabic ≥5 | Hydroxy Ethyl Cellulose / Carboxy Methyl Cellulose / Oligomers of Cellulose / Pectin / Guar Gum / Gum Arabic ≥5 | Hydroxy Ethyl Cellulose / Carboxy Methyl Cellulose / Oligomers of Cellulose / Pectin / Guar Gum / Gum Arabic ≥5 | Hydroxy Ethyl Cellulose / Carboxy Methyl Cellulose / Oligomers of Cellulose / Pectin / Guar Gum / Gum Arabic ≥5 | Hydroxy Ethyl Cellulose / Carboxy Methyl Cellulose / Oligomers of Cellulose / Pectin / Guar Gum / Gum Arabic ≥5 |
| Sodium Polyacrylate (ppm) | ≤300 | ≤300 | ≤300 | ≤300 | ≤300 | ≤300 | ≤300 |
| Polyacrylic acid (ppm) | - | - | - | - | - | - | - |
| Sodium Polystyrene Sulfonate (Na-PSS; Kayexalate) ppm | ≤300 | ≤300 | ≤300 | ≤300 | ≤300 | ≤300 | ≤300 |
| Total (wt. %) | 100 | 100 | 100 | 100 | 100 | 100 | 100 |
| Properties | | | | | | | |
| pH | 10 (Buffered) | 9.35 | 8.75 | 8.50 | 8.50 | 8.89 | 7.78 |
| Viscosity of Gel Mixture mm2/s (cP) at (~20 °C) | 100-150,000 | 100-150,000 | 100-150,000 | 100-150,000 | 100-150,000 | 100-150,000 | 100-150,000 |
| Injury Type | Severe & Deep | Severe & Deep | Severe & Deep | Severe & Deep | Severe | Severe | Mild |
| Time of Application | Immediately | Immediately | Immediately | Immediately | Immediately | Immediately | Immediately |
| Physiological pH Condition | Acidosis | Acidosis | Acidosis | Acidosis | Acidosis | Acidosis | Acidosis |
| Total Injured Burn Area (%) | ≥20 | ≥20 | ≥10-20 | ≥10-20 | ≥20 | ≥10 | ≤10 |

FIG. 24

| Ingredients gps(s) in 1 Liter | Example 1 | Example 2 | Example 3 | Example 4 | Example 5 | Example 6 | Example 7 | Example 8 | Example 9 | Example 10 |
|---|---|---|---|---|---|---|---|---|---|---|
| | | | | Formulation (I) | (Acidosis) | Condition | | | | |
| DI Water (gm) | 1000 | 1000 | 1000 | 1000 | 1000 | 1000 | 1000 | 1000 | 1000 | 1000 |
| Sodium Chloride (gm) | 300 | 300 | 300 | 300 | 300 | 300 | 300 | 300 | 300 | 300 |
| Sodium Bicarbonate (gm) | 17.69 | 0.38 | 0.126 | 0.0378 | 0.0038 | 0.00363 | 0.00109 | 0.38 | 0.126 | 0.0378 |
| Sodium Carbonate | 27.93 | | | | | | | | | |
| Sodium Lactate (gm) | 156.00 | 156.00 | 44.80 | 14.80 | 14.80 | 0.69 | 0.39 | 156.00 | 44.80 | 14.80 |
| Sodium Acetate (gm) | 82.00 | 8.28 | 4.40 | 3.78 | | 0.16 | 0.05 | 8.28 | 4.40 | 3.78 |
| Trisodium Citrate (gm) | 420.00 | 420.00 | 26.00 | 42.00 | | 25.00 | 9.00 | 420.00 | 26.00 | 42.00 |
| Lactic Acid (gm) | | | | | | | | | | |
| Citric Acid (gm) | | | | | | | | | | |
| Acetic Acid (gm) | | | | | | | | | | |
| Gelling Agent (gm) | Hydroxy Ethyl Cellulose, Oligomers of Cellulose, Pectin, Carboxy Methyl Cellulose, Guar Gum, Gum Arabic | Hydroxy Ethyl Cellulose, Oligomers of Cellulose, Pectin, Carboxy Methyl Cellulose, Guar Gum, Gum Arabic | Hydroxy Ethyl Cellulose, Oligomers of Cellulose, Pectin, Carboxy Methyl Cellulose, Guar Gum, Gum Arabic | Hydroxy Ethyl Cellulose, Oligomers of Cellulose, Pectin, Carboxy Methyl Cellulose, Guar Gum, Gum Arabic | Hydroxy Ethyl Cellulose, Oligomers of Cellulose, Pectin, Carboxy Methyl Cellulose, Guar Gum, Gum Arabic | Hydroxy Ethyl Cellulose, Oligomers of Cellulose, Pectin, Carboxy Methyl Cellulose, Guar Gum, Gum Arabic | Hydroxy Ethyl Cellulose, Oligomers of Cellulose, Pectin, Carboxy Methyl Cellulose, Guar Gum, Gum Arabic | Hydroxy Ethyl Cellulose, Oligomers of Cellulose, Pectin, Carboxy Methyl Cellulose, Guar Gum, Gum Arabic | Hydroxy Ethyl Cellulose, Oligomers of Cellulose, Pectin, Carboxy Methyl Cellulose, Guar Gum, Gum Arabic | Hydroxy Ethyl Cellulose, Oligomers of Cellulose, Pectin, Carboxy Methyl Cellulose, Guar Gum, Gum Arabic |
| Greater Than or Equal to gm | 108.18 | 94.33 | 68.77 | 68.61 | 65.73 | 66.29 | 65.47 | 89.23 | 63.77 | 58.01 |
| Sodium Polyacrylate (ppm) | | | | | | | | | | |
| Polyacrylic acid (ppm) | | | | | | | | | | |
| Sodium Polystyrene Sulfonate (Na-PSS: Kayexalate) ppm | ≤ 300 | ≤ 300 | ≤ 300 | ≤ 300 | ≤ 300 | ≤ 300 | ≤ 300 | ≤ 300 | ≤ 300 | ≤ 300 |
| Total (gm) | 2103.80 | 1978.81 | 1444.09 | 1428.25 | 1360.23 | 1391.14 | 1374.91 | 1873.81 | 1339.49 | 1213.25 |
| Properties | | | | | | | | | | |
| pH | 10 (Buffered) | 9.00 | 8.75 | 8.50 | 8.50 | 8.00 | 7.75 | 9.00 | 8.75 | 8.50 |
| Viscosity of Gel Mixture cm2/s (cP) at (~20 °C) | 100-150,000 | 100-150,000 | 100-150,000 | 100-150,000 | 100-150,000 | 100-150,000 | 100-150,000 | 100-150,000 | 100-150,000 | 100-150,000 |
| Injury Type | Severe & Deep | Severe & Deep | Severe & Deep | Severe & Deep | Severe | Severe | Mild | Severe & Deep | Severe & Deep | Severe & Deep |
| Time of Application | Immediately | Immediately | Immediately | Immediately | Immediately | Immediately | Immediately | Immediately | Immediately | Immediately |
| Type of Patient | Normal | Normal | Normal | Normal | Normal | Normal | Normal | Normal | Normal | Normal |
| Physiological Treatment | | | | | | | | | | |
| Sodium (Na+) ion Deficiency | Hyponatremia | Hyponatremia | Hyponatremia | Hyponatremia | Hyponatremia | Hyponatremia | Hyponatremia | Hyponatremia | Hyponatremia | Hyponatremia |
| Potassium (K+) ion proliferation | Hyperkalemia | Hyperkalemia | Hyperkalemia | Hyperkalemia | Hyperkalemia | Hyperkalemia | Hyperkalemia | Hyperkalemia | Hyperkalemia | Hyperkalemia |
| Physiological pH Condition | Acidosis | Acidosis | Acidosis | Acidosis | Acidosis | Acidosis | Acidosis | Acidosis | Acidosis | Acidosis |
| Total Injured Burn Area (%) | ≥ 1.20 | ≥ 1.20 | ≥ 1.20 | ≥ 1.20 | ≥ 1.20 | ≥ 1.10 | ≤ 1.0 | ≥ 1.20 | ≥ 1.20 | ≥ 1.20 |

| Ingredients gm(s) to 1 Liter | Example 11 | Example 12 | Example 13 | Example 14 | Example 15 | Example 16 | Example 17 | Example 18 | Example 19 | Example 20 |
|---|---|---|---|---|---|---|---|---|---|---|
| DI Water (gm) | 1000 | 1000 | 1000 | 1000 | 1000 | 1000 | 1000 | 1000 | 1000 | 1000 |
| Sodium Chloride (gm) | 80 | 80 | 80 | 80 | 80 | 300 | 80 | 80 | 80 | 250 |
| Sodium Bicarbonate (gm) | | | | | | | | | | |
| Sodium Carbonate | | | | | | | | | | |
| Sodium Lactate (gm) | 12.90 | 12.90 | 12.90 | 12.90 | 362.80 | 12.60 | 542.86 | 12.89 | 12.90 | 12.60 |
| Sodium Acetate (gm) | | | | | | 35.71 | | | | 35.71 |
| Trisodium Citrate (gm) | | | | | | 937 | 374 | | | 937 |
| Lactic Acid (gm) | 0.0018 | 0.0303 | 0.0028 | 0.0018 | 0.2798 | 0.0028 | 0.63 | 0.0303 | 0.0028 | 0.0028 |
| Citric Acid (gm) | | | | | | 0.192 | 0.077 | | | 0.192 |
| Acetic Acid (gm) | | | | | | 6.3 | | | | 6.3 |
| Gelling Agent (gm) | Hydroxy Ethyl Cellulose Oligomers of Cellulose Pectin Carboxy Methyl Cellulose Guar Gum Gum Arabic | Hydroxy Ethyl Cellulose Oligomers of Cellulose Pectin Carboxy Methyl Cellulose Guar Gum Gum Arabic | Hydroxy Ethyl Cellulose Oligomers of Cellulose Pectin Carboxy Methyl Cellulose Guar Gum Gum Arabic | Hydroxy Ethyl Cellulose Oligomers of Cellulose Pectin Carboxy Methyl Cellulose Guar Gum Gum Arabic | Hydroxy Ethyl Cellulose Oligomers of Cellulose Pectin Carboxy Methyl Cellulose Guar Gum Gum Arabic | Hydroxy Ethyl Cellulose Oligomers of Cellulose Pectin Carboxy Methyl Cellulose Guar Gum Gum Arabic | Hydroxy Ethyl Cellulose Oligomers of Cellulose Pectin Carboxy Methyl Cellulose Guar Gum Gum Arabic | Hydroxy Ethyl Cellulose Oligomers of Cellulose Pectin Carboxy Methyl Cellulose Guar Gum Gum Arabic | Hydroxy Ethyl Cellulose Oligomers of Cellulose Pectin Carboxy Methyl Cellulose Guar Gum Gum Arabic | Hydroxy Ethyl Cellulose Oligomers of Cellulose Pectin Carboxy Methyl Cellulose Guar Gum Gum Arabic |
| Greater Than or Equal to gm | 54.64809 | 54.64815 | 54.63814 | 54.64869 | 89.13395 | 134.29024 | 98.83535 | 54.64815 | 54.63814 | 133.79024 |
| Sodium Polyacrylate (ppm) | | | | | | | | | | |
| Polyacrylic acid (gm) | ≤300 | ≤300 | ≤300 | ≤300 | ≤300 | ≤300 | ≤300 | ≤300 | ≤300 | ≤300 |
| Sodium Polystyrene Sulfonate (Na-PSS; Kayexalate) ppm | | | | | | | | | | ≤300 |
| Total (gm) | 1148 | 1147 | 1147 | 1148 | 1481 | 2409 | 2897 | 1147 | 1147 | 2348 |
| Properties | P | R | Q | P | E | R | T | T | E | S |
| pH | 6.9 (Buffered) | 6.8 (Buffered) | 6.7 (Buffered) | 6.9 (Buffered) | 6.8 (Buffered) | 6.7 (Buffered) | 6.7 (Buffered) | 6.8 (Buffered) | 6.7 (Buffered) | 6.7 (Buffered) |
| Viscosity of Gel Mixture mm2/s (cP) at (~20 °C) | 100-150,000 | 100-150,000 | 100-150,000 | 100-150,000 | 100-150,000 | 100-150,000 | 100-150,000 | 100-150,000 | 100-150,000 | 100-150,000 |
| For Injury Type | Severe | Severe & Deep | Severe & Deep | Severe | Severe & Deep | Severe & Deep | Severe & Deep | Severe & Deep | Severe & Deep | Severe & Deep |
| Time of Application | Delayed | Delayed | Delayed | Delayed | Delayed | Delayed | Delayed | Delayed | Delayed | Delayed |
| Type of Patient | Alkalosis Patient | Alkalosis Patient | Alkalosis Patient | Alkalosis Patient | Alkalosis Patient | Alkalosis Patient | Alkalosis Patient | Alkalosis Patient | Alkalosis Patient | Alkalosis Patient |
| Physiological treatment Sodium (Na+) ion Deficiency Potassium (K+) ion proliferation | Hyponatremia Hyperkalemia | Hyponatremia Hyperkalemia | Hyponatremia Hyperkalemia | Hyponatremia Hyperkalemia | Hyponatremia Hyperkalemia | Hyponatremia Hyperkalemia | Hyponatremia Hyperkalemia | Hyponatremia Hyperkalemia | Hyponatremia Hyperkalemia | Hyponatremia Hyperkalemia |
| pH Condition | Alkalosis | Alkalosis | Alkalosis | Alkalosis | Alkalosis | Alkalosis | Alkalosis | Alkalosis | Alkalosis | Alkalosis |
| Total Injured Burn Area (%) | ≥1.30 | ≥1.30 | ≥20 | ≥1.20 | ≥1.20 | ≥1.20 | ≥1.20 | ≥1.20 | ≥1.20 | ≥1.20 |

Picture showing the condition of burn injured area after the application of modified Formulation (I) over burn injured area and its vicinities at the onset of the injury showing no blister formation (Picture taken after 4 days)

GEL COMPOSITIONS FOR MITIGATION OF BURN INJURIES, KITS CONTAINING THE GEL COMPOSITIONS, AND ASSOCIATED METHODS

CROSS REFERENCE TO RELATED APPLICATION

This application claims the benefit of priority under 35 U.S.C. § 119(e) to U.S. Provisional Application Ser. No. 62/950,643, filed Dec. 19, 2019, the contents of which are hereby incorporated by reference in its entirety.

TECHNICAL FIELD

The present application is directed to gel compositions for mitigation of burn injuries, to kits containing the gel compositions, and to methods for using the gel compositions.

BACKGROUND

The human body is susceptible to extreme heat or cold due to delicate nature of the chemical makeup of its exterior and interior organic building blocks; the ubiquitous existence of aqueous phase (blood/plasma/serum, extracellular fluid etc.) present in the interior of the human body; its delicate homeostatic ion balances ($Na^+$ and $K^+$) and the ionic ratios ($Na^+/K^+$) in blood plasma/serum and/or extracellular fluid; milder and narrow functional/process parameters, viz., pH ($7.35 \geq pH \geq 7.45$) i.e., its moderate buffer strength which are interdependent ion transport capabilities etc.

These are the essential features for the optimal functioning of human body within a temperature narrow range (avg. ~98.6° F./37° C.) to ensure optimum thermodynamic and kinetic balances inside human body due to the delicate thermochemical vulnerability of its protective exterior layers (skin) which too are primarily composed of protein and lipid materials.

Potassium ($K^+$) ion the most abundant cation in the intracellular fluid and plays vital role in normal human physiology and electrophysiology. The bulk of total body potassium ($K^+$) is intracellular 3500 mEq (~98%), with only approximately 70 mEq (~2%) in the extracellular fluid for a 70 kg human being. This large gradient between intracellular potassium ($K_i^+$) (~120-140 mEq/L) and extracellular potassium ($K_e^+$) (~4 mEq/L), as shown in FIG. 1, not only determines the optimal resting membrane potential of most type of cells, they also dictate the depolarization and polarization rate, i.e., the action potentials (See FIG. 2) of the electrically active cell (e.g., cardiac, nerve etc.) membranes. From now onwards, unless specified, $K_e^+$ is going to be denoted as $K^+$. The delicate ionic ratios, viz., intracellular potassium ($K_i^+$) ion to extracellular potassium ($K_e^+$) ion ratios ($K_i^+/K_e^+$), as well as intracellular sodium ($Na_i^+$) ion to extracellular sodium ($Na_e^+$), ion ratios ($Na_i^+/Na_e^+$) and their intracellular and extracellular concentrations, i.e., the concentration gradients of the ions and their absolute values are also vitally important for the generation of correct action potentials within the cells; and therefore, are critical for the normal functions of neurons, skeletal muscles, cardiac muscles and renal function. As a result, very small absolute changes in the extracellular potassium ($K^+$) ion concentration will have a major effect on this ratio and accordingly, on the function of the all the electrically excitable nerve, cardiac or skeletal muscle cells etc. Therefore, potassium ($K^+$), sodium ($Na^+$) ions, ions drive the action potentials in nerve, cardiac and muscle cells by actively crossing the cell membrane and shifting the membrane potentials, which is the difference in electrical potential between the exterior and interior of the cells.

However, calcium ions ($Ca^{2+}$) also play a significant role in membrane potentials of the cardiac cells along with sodium ($Na^+$) and potassium ($K^+$) ions. Besides the active transport of potassium ($K^+$) ions across the cell membranes, these ions also move passively (bypassing the gated ion channels) between the extracellular and intracellular compartments. An overload of passive potassium ($K^+$) ion transport, caused by higher levels of extracellular/serum potassium ($K^+$), is capable of raising the resting membrane potential in the absence of a stimulus. Excess potassium ($K^+$) ions ($\geq 5.5$ mEq/L) in extracellular/serum fluid, known as hyperkalemia (See FIGS. 3 and 4), can disrupt the transmembrane potential in cardiac cells that regulate ventricular conduction and contraction. Therefore, the effects of hyperkalemia on cardiac electrophysiology are of greatest concern because they can cause arrhythmias and death.

The release of potassium ($K^+$) ions into the extracellular, blister and intravascular fluid occurs during severe burning due to cell lysis, tissue necrosis and thus releasing exorbitant amount of potassium ($K^+$) ions. On top of that, as a result of burn injury, respiratory acidosis (e.g., $CO_2$ inhalation) may occur in extracellular fluid, i.e., there is a pH drop due to increase in the hydrogen ($H^+$) ion concentration in blood serum or extracellular fluid. Eventually, this excess hydrogen ($H^+$) ion makes its way into the healthy cells in exchange of $K^+$ ion release, which in turn, makes their ($K^+$) way out in the extracellular fluid and blood serum, thus further complicating hyperkalemia (See FIGS. 4 and 5). On the same note, since the skin layers are primarily composed of complex organic (protein, lipid etc.) materials, it is also unable to withstand any extreme and prolonged abnormal ambient temperatures.

Although there are various treatment procedures for treating burn wound, understanding the burn fluid chemistry is very important not only to correctly and rapidly treat the burn injuries while simultaneously offering pain management. Therefore, it is indispensable to apply gel mixture formulation disclosed herein to minimize blister proliferation, blister membrane protection, suppression of hyponatremia ($Na^+ \leq 135$ mEq/L) with simultaneous removal of excessive potassium ($K^+$) ions from the extracellular and vascular fluid, i.e., rectification of hyperkalemia, with pH balance to protect major organs from the onset of burn shock.

SUMMARY

Embodiments of this disclosure include gel formulations, methods for using the gel formulations, burn kits including the gel formulations, and methods for using the burn kits.

The present disclosure relates to gel formulations for protecting, treating and rejuvenating (first and second-degree) burned exterior skin layer and corresponding minimization and/or retarding blister and edema formation; and more particularly, a formulation method and its composition of topical (pH-7.01-10.0 at ~37° C.) gel mixture(s) for its external (in vitro) application as aqueous concentrated sodium chloride (NaCl) as ($Na^+$) ion pump and other dissolved aqueous sodium ($Na^+$) cation of polyelectrolytes, cation exchange resins and anions as (bicarbonate, acetate, citrate, lactate etc.) as pH and SID control ingredients and/or sodium salt containing buffers, dissolved inside non-cross-linked polymeric substrate/gel/matrix, where the gel mixture is prepared using sterile and deionized water, applied on the exterior of the skin surface to diffuse the ions via transdermal route, to regulate and minimize the formation of blister, edema and excess extracellular fluid which take place from the onset of burn shock via capillary loss of water/plasma/serum in vivo, while impeding and minimizing hyponatremia ($Na^+ \leq 135$ mEq/L) as a result of the dilution of the extracellular and vascular fluid resulting in initial acidosis (pH drop below 7.35) to rectify acidosis (from pH~7.2→7.35≤pH≤7.45); with simultaneous counter diffusional excretion/expulsion/removal (in vitro) of excess accumulated potassium ($K^+$) and hydrogen ($H^+$) ions from the blister/extracellular/vascular fluids as a result of cell lysis, and/or tissue necrosis from the edema/blister and extracellular fluid, through the transdermal route via counter diffusional absorption of excess potassium ($K^+$) ions in the gel matrix (in vitro) for controlling or reducing or minimizing local and overall hyperkalemia in blister/edema, intravascular, extracellular and interstitial fluid from the onset of burn shock; resulting in minimizing subsequent alkalosis (pH≥7.45 increase) in the extracellular fluid, to restore the normal homeostasis and rectify the transmembrane potentials of assortment of cells, while simultaneously slowing down/stop vascular transmembrane fluid loss.

When gel matrix mixture Formulation (I) is applied as pH control agent on the exterior of the burn injured skin surface the sodium bicarbonate present in gel mixture formulation rectifies local initial acidosis (pH), thereby diminishing hydrogen ion ($H^+$) or hydroxyl ($OH^-$) ion concentration respectively, thus preventing potassium ($K^+$) ion release from healthy cells and push back part of the locally released $K^+$ ions in the unharmed cells to prevent subsequent alkalosis (pH≥7.45); and also simultaneously acts to reduce and minimize pain from the right from the onset or during the hypovolemic phase of burn shock; as the internal electrolyte ($K^+/Na^+/H^+$) balances are rectified and consequently fluid imbalances are slowed down and/or reversed and subsequently restored, to defend, protect, rectify and restore the organ functionalities by correcting the cell action potentials during the polarization and depolarizations phases of transmembrane ion transport.

Embodiments of this disclosure include a method for preparing an assortment of gel mixture Formulations (I and II) in different variations that is used as first responder to mitigate first and second degree burn shock at the onset or its aftermath by its immediate application on the exterior of the injured skin surfaces and its vicinities to minimize hyponatremia ($Na^+ \leq 135$ mEq/L) and hyperkalemia (overall $K^+ \geq 5.5$ mEq/L) to protect cardiac and renal functions and also as a pain management regimen. This gel mixture is viscous in nature, comprised of ionized and concentrated sodium chloride dissolved in deionized and sterile aqueous medium in biodegradable sugar-based biopolymers/oligomers and their derivatives as substrate/gel/matrix dissolved in pH-controlled condition (pH 7.01-10.0), to restore interior pH (7.35≤pH≤7.45) of extracellular/blister/serum fluid. The ionic diffusion of sodium ($Na^+$) ions as ion pump help suppress and minimize blister and edema formation by correcting hyponatremia of the fluid while suppressing the vascular transcapillary permeability to minimize and control the translocation of serum fluids into the extracellular or interstitial spaces while simultaneously extracting potassium ($K^+$) ions (in vitro) via ionic counter diffusion across transdermal route to repair hyperkalemia in blood plasma, blister and extracellular fluids which occurs due to cell lysis, tissue necrosis and respiratory, metabolic and hyperchloremic acidosis. The presence of sodium bicarbonate ($NaHCO_3$) and/or other biocompatible sodium salts of organic acids alone or in combination, present as pH control (7.55≥pH≥10) in the gel mixture Formulation (I) would rectify the pH imbalance or hydrogen ($H^+$) ions imbalances in blister and extracellular fluids during the initial stages of the burn shock. Since, initial acidosis is followed by subsequent alkalosis (pH≥7.45) after potassium ($K^+$) ions gets expelled from intercellular compartments when proliferation of hydrogen ($H^+$) ions move inside the healthy cells due to initial acidosis (due to lactic acid dissociation from metabolic release and or respiratory acidosis) in the extracellular/blister fluids cause further rise in potassium ($K^+$) ion concentrations in the extracellular/blister/serum fluids.

These series of actions in turn, also reduces the requirement of introducing excessive resuscitation fluid via intravenous and enteral routes and thus reduce the negative impact of introducing excess resuscitation liquid and avoid "fluid creep". This gel mixture is applicable to thermal and electrical first and second-degree burn injuries, however, is not applicable for chemical related burn injury.

BRIEF DESCRIPTION OF THE DRAWINGS

FIG. 1: A diagram showing typical intracellular ion concentrations versus extracellular fluids/plasma ion concentrations.

FIG. 3: A diagram example of severely burn injured patient's intracellular cell ion concentration with initial acidosis and hyperkalemia versus extracellular fluids/plasma ion concentrations.

FIG. 5: A diagram showing an example of severely burn injured patient's intracellular cell ion concentration with subsequent local alkalosis and local hyperkalemia in extracellular fluids/plasma ion concentrations

FIG. 9: A graph of excessively high extracellular local potassium ($K_e^+$) ion expulsion through transdermal route outside to the gel mixture matrix (in vitro) with multiple replacement of freshly applied gel mixture formulation to rapidly remove the local potassium ($K_e^+$) ion before their dispersion into the vast network of the circulatory system.

FIG. 21: Table of example formulations according to embodiments of this disclosure.

FIG. 22: Table of example formulations according to embodiments of this disclosure.

Figure 23:
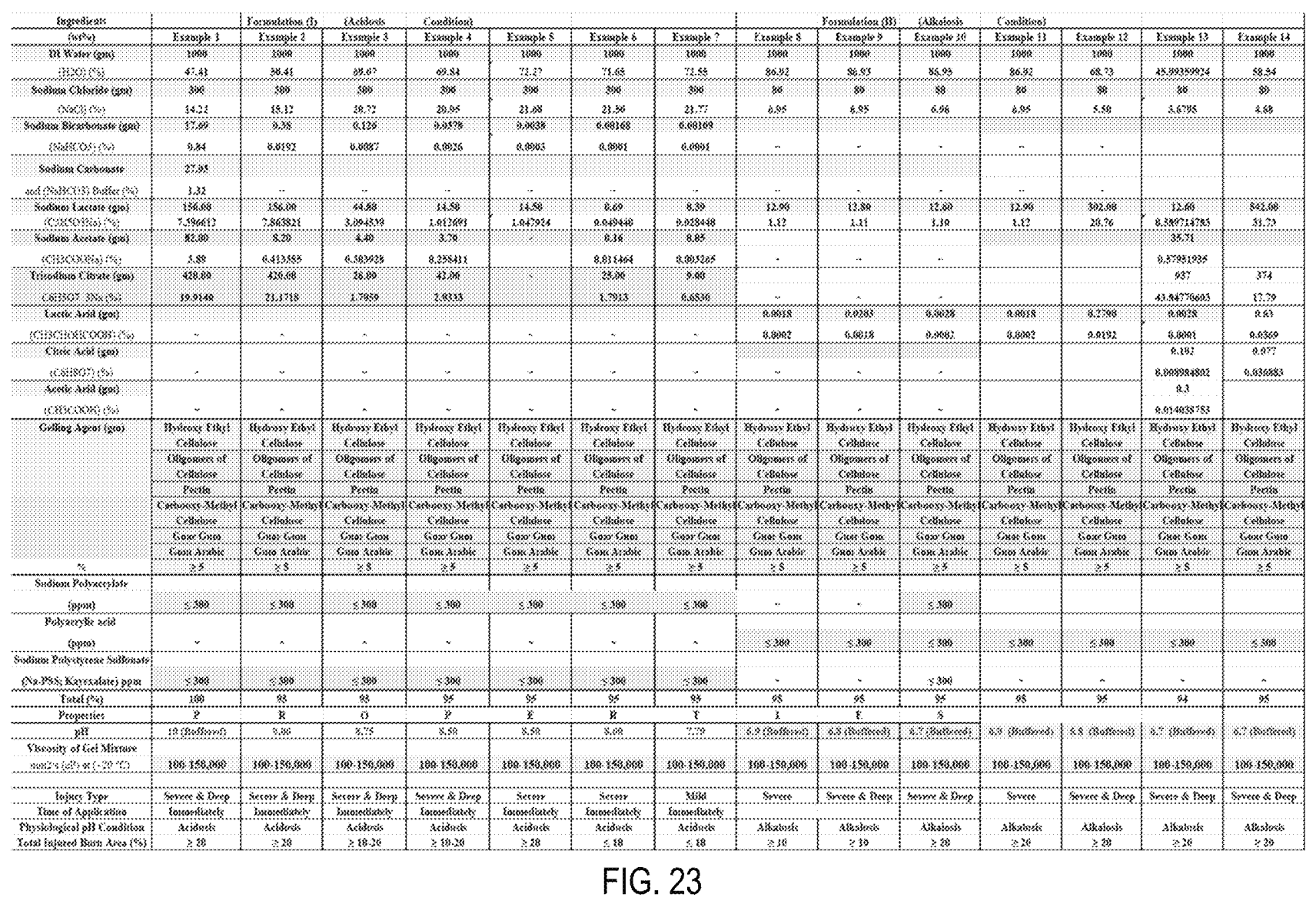

FIG. 23: Table of example formulations according to embodiments of this disclosure.

FIG. 24: Table of example formulations according to embodiments of this disclosure.

FIG. 25: Table of example formulations according to embodiments of this disclosure.

FIG. 26: Table of example formulations according to embodiments of this disclosure.

DETAILED DESCRIPTION

Figure 2:
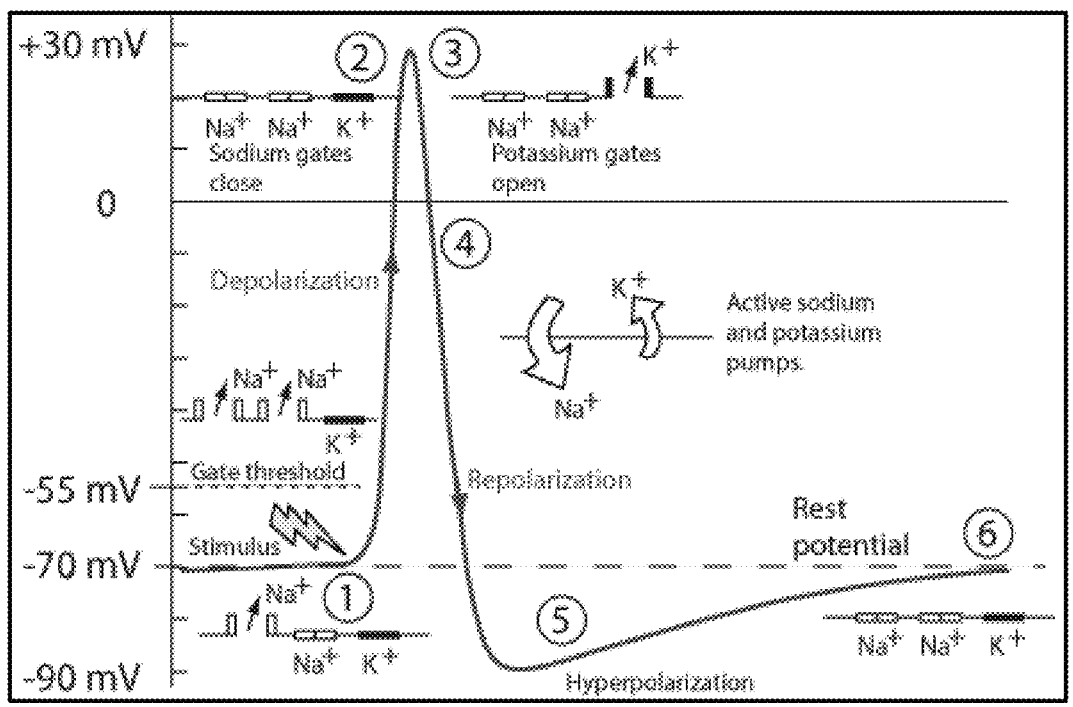
FIG. 2: A graph showing action potentials (depolarization, repolarization and hyperpolarization) of neurons.

Embodiments of this disclosure include gel formulations, methods for using the gel formulations, burn kits including the gel formulations, and methods for using the burn kits.

Gel formulations according to embodiments include sodium chloride, sodium bicarbonate, sodium carbonate, sodium lactate, sodium acetate, trisodium citrate a gelling agent, and water from a sterilized and deionized source. The gel formulations contains only pharmaceutical grade ingredients and have a total sodium-ion concentration greater than or equal to 154 g/L; a total bicarbonate-ion concentration from $6 \times 10^{-5}$ g/L to 17.70 g/L; a yield point of greater than or equal to 1000 poise; and an apparent viscosity from 100 centipoise to 150,000 centipoise.

In some embodiments, the gel formulation may have a pH from 7.01 to 10.00 and may include, per liter of the gel formulation at 25° C.: from 80 g to 340 g sodium chloride; from $6 \times 10^{-5}$ g to 42 g sodium bicarbonate; from $1.0 \times 10^{-6}$ g to 1.3 g sodium carbonate; from $1.6 \times 10^{-2}$ g to 156 g sodium lactate; from $1.53 \times 10^3$ g to 82 g sodium acetate; from 0.198 g to 420 g trisodium citrate; and the gelling agent, wherein the gelling agent is selected from the group consisting of hydroxyethyl cellulose, oligomers of cellulose, pectin, carboxymethyl cellulose, guar gum, gum Arabic, and mixtures thereof.

In embodiments, the gel formulation may be a Formulation (I) or a Formulation (II). Generally, the Formulation (I) may be appropriate for use immediately after a burn injury. Generally, the Formulation (II) may be appropriate for use following earlier application of a Formulation (I), particularly to avoid blistering. Other distinguishing characteristics and physiological effects provided by Formulation (I) and Formulation (II) will be described subsequently. Thus, in some embodiments, the gel formulation may be a Formulation (I), having a pH from 7.45 to 10.00 and comprising, per liter of the gel formulation at 25° C.: from 300 g to 340 g sodium chloride; from $3.5 \times 10^{-4}$ g to 42 g sodium bicarbonate; from $1 \times 10^{-6}$ g to 1.3 g sodium carbonate; from $1.2 \times 10^{-1}$ g to 156 g sodium lactate; from $1.15 \times 10^{-2}$ g to 82 g sodium acetate; and from 1.471 g to 420 g trisodium citrate. In some embodiments, the gel formulation may be a Formulation (II), having a pH from 7.01 to 7.35 and comprising, per liter of the gel formulation at 25° C.: from 80 g to 300 g sodium chloride; from $6.0 \times 10^{-5}$ g to 17.7 g sodium bicarbonate; from $1.0 \times 10^{-6}$ g to $2.3 \times 10^{-4}$ g sodium carbonate; from $1.6 \times 10^{-2}$ g to $7.67 \times 10^{-2}$ g sodium lactate; from $1.53 \times 10^{-3}$ g to $7.2 \times 10^{-2}$ g sodium acetate; and from 0.198 g to 0.954 g trisodium citrate.

In some embodiments, the gel formulation may further include sodium polyacrylate, polyacrylic acid, and less than 300 mg sodium polystyrene sulfonate (Na-PSS; Kayexalate) per liter of the gel formulation.

In some embodiments, the gel formulation may further include a pain-relieving agent. Examples of pain-relieving agents include menthol and its derivatives. When menthol is present in the gel formulation, the menthol may have a concentration from 5 g/L to 100 g/L, or from 40 g/L to 50 g/L.

In some embodiments, all salts present in the gel formulation are sodium salts and the gel formulation does not contain any potassium salts or potassium ions. In some embodiments, all salts of the gel formulation are completely dissolved in a gel matrix of the gelling agent and the water.

In one example embodiment, the gel formulation may have a pH from 7.01 to 10.00 and consist of, per liter of the gel formulation at 25° C.: from 80 g to 340 g sodium chloride; from $6 \times 10^{-5}$ g to 42 g sodium bicarbonate; from $1.0 \times 10^{-6}$ g to 1.3 g sodium carbonate; from $1.6 \times 10^{-2}$ g to 156 g sodium lactate; from $1.53 \times 10^{-3}$ g to 82 g sodium acetate; from 0.198 g to 420 g trisodium citrate; the gelling agent, wherein the gelling agent is selected from the group consisting of hydroxyethyl cellulose, oligomers of cellulose, pectin, carboxymethyl cellulose, guar gum, gum Arabic, and mixtures thereof; and balance water from the sterilized and deionized source.

Features of the gel formulations and their respective ingredients will be described subsequently in detail.

The gel formulations according to embodiments may be used in methods for mitigating a burn injury to a burn victim. Such methods may include applying the gel formulation within 10 minutes of a burn injury on injured skin of the burn victim. The methods may further include spreading the applied gel formulation on the injured skin to prevent loss of vascular fluid into extracellular regions, to expedite sodium-ion transfer across transdermal membranes in vivo, to expel potassium ions across the transdermal membranes in vitro, and to prevent blister formation or proliferation. The methods may further include reapplying fresh gel formulation on the injured skin to maintain high sodium ion concentration gradient across transdermal membranes in vitro to in vivo and high potassium ion concentration gradient across the transdermal membranes in vivo to in vitro.

In the methods for mitigating a burn injury to a burn victim, the gel formulation may have a pH from 7.01 to 10.00 and may include, per liter of the gel formulation at 25° C.: from 80 g to 340 g sodium chloride; from $6\times10^{-5}$ g to 42 g sodium bicarbonate; from $1.0\times10^{-6}$ g to 1.3 g sodium carbonate; from $1.6\times10^{-2}$ g to 156 g sodium lactate; from $1.53\times10^{-3}$ g to 82 g sodium acetate; from 0.198 g to 420 g trisodium citrate; and a gelling agent selected from the group consisting of hydroxyethyl cellulose, oligomers of cellulose, pectin, carboxymethyl cellulose, guar gum, gum Arabic, and mixtures thereof. In some embodiments, all salts present in the gel formulation are sodium salts and the gel formulation does not contain any potassium salts or potassium ions. In one example embodiment, the gel formulation may have a pH from 7.45 to 10.00 and consist essentially of, per liter of the gel formulation at 25° C.: from 300 g to 340 g sodium chloride; from $3.5\times10^{-4}$ g to 42 g sodium bicarbonate; from $1\times10^{-6}$ g to 1.3 g sodium carbonate; from $1.2\times10^{-1}$ g to 156 g sodium lactate; from $1.15\times10^{-2}$ g to 82 g sodium acetate; from 1.471 g to 420 g trisodium citrate; a gelling agent selected from the group consisting of hydroxyethyl cellulose, oligomers of cellulose, pectin, carboxymethyl cellulose, guar gum, and gum arabic; and balance water from a sterilized and deionized source.

In the methods for mitigating a burn injury to a burn victim, the gel formulation may include sodium chloride in an amount sufficient to mitigate hyponatremia in blister fluids, extracellular fluids, and blood plasma with simultaneous pain management while restoring sodium/potassium ion imbalances from the burn injury. In the methods for mitigating a burn injury to a burn victim, the gel formulation may include sodium bicarbonate in an amount sufficient to result in mitigating respiratory and metabolic acidosis and SID in blister fluids when pH drops below 7.35 in extracellular fluid and blood plasma with simultaneous pain management while restoring sodium/potassium ion imbalances from the burn injury. In the methods for mitigating a burn injury to a burn victim, the gel formulation may include sodium lactate in an amount sufficient to result in mitigating metabolic acidosis and SID management in blister fluid, extracellular fluid, and blood plasma. In the methods for mitigating a burn injury to a burn victim, the gel formulation may include gelling agent in an amount sufficient to prevent hyperkalemia and acidosis in blister fluids, extracellular fluids, and blood plasma by receiving in vitro excess $K^+$ and $H^+$ ions from blister fluids, blood plasma, extracellular fluid, while delivering hydroxyl ($OH^-$) ions from the gel formulation in vivo into the blister fluid, extracellular fluid, and blood plasma to prevent acidosis and sodium ($Na^+$) ions from the gel formulation in vivo into the blister fluid, extracellular fluid, and blood plasma to prevent hyponatremia. Thereby, the combination of water, sodium chloride, sodium bicarbonate, sodium lactate, and gelling agent in the gel formulation simultaneously rectifies pH imbalances due to respiratory and metabolic acidosis, expels excess $K^+$ ions in vitro, repletes $Na^+$ ion deficiency in vivo, restores dynamic physiological $Na^+/K^+$ ion imbalances, and mitigates SID imbalances within blister fluid, extracellular fluid and blood plasma/serum with simultaneous pain management while restoring sodium/potassium ion imbalances from the burn injury.

Further embodiments of this disclosure include burn treatment kits that include a Formulation (I) as previously described and a Formulation (II) as previously described, packaged for use by a person having a burn injury. In this regard the Formulation (I) and the Formulation (II) may be contained in any suitable container such as a bottle or a squeezable tube, for example. The formulations may be further packaged together or separately, optionally with instructions describing their use to mitigate burn injuries. Thus, burn treatment kits according to embodiments may include a first gel formulation that mitigates acidosis, hyponatremia, hyperkalemia when applied following a burn injury; and a second gel formulation that mitigates alkalosis, hyponatremia, hyperkalemia after blister formation is apparent after the burn injury.

In burn treatment kits according to embodiments, the first gel formulation may include, per liter of the first gel formulation at 25° C.: from 300 g to 340 g sodium chloride; from $3.5\times10^{-4}$ g to 42 g sodium bicarbonate; from $1\times10^{-6}$ g to 1.3 g sodium carbonate; from $1.2\times10^{-1}$ g to 156 g sodium lactate; from $1.15\times10^{-2}$ g to 82 g sodium acetate; from 1.471 g to 420 g trisodium citrate; a gelling agent selected from the group consisting of hydroxy ethyl cellulose, oligomers of cellulose, pectin, carboxy-methyl cellulose, guar gum, and gum arabic, and combinations thereof, and water from a sterilized and deionized source. In such embodiments, the first gel formulation has a pH from 7.45 to 10; a total sodium-ion concentration greater than or equal to 154 g/L; a total bicarbonate-ion concentration from 0.01 g/L to 17.70 g/L; a yield point of greater than or equal to 1000 poise; and an apparent viscosity from 100 centipoise to 150,000 centipoise.

In burn treatment kits according to embodiments, the second gel formulation may include, per liter of the second gel formulation at 25° C.: from 80 g to 300 g sodium chloride; from $6.0\times10^{-5}$ g to 17.7 g sodium bicarbonate; from $1.0\times10^{-6}$ g to $2.3\times10^{-4}$ g sodium carbonate; from $1.6\times10^{-2}$ g to $7.67\times10^{-2}$ g sodium lactate; from $1.53\times10^{-3}$ g to $7.2\times10^{-2}$ g sodium acetate; from 0.198 g to 0.954 g trisodium citrate; a gelling agent selected from the group consisting of hydroxy ethyl cellulose, oligomers of cellulose, pectin, carboxy-methyl cellulose, guar gum, gum arabic, and combinations thereof; and water from a sterilized and deionized source. In such embodiments, the second gel formulation has a pH from 7.01 to 7.35; a total sodium-ion concentration greater than or equal to 120 g/L; a total lactate-ion concentration from 0.01 g/L to 0.08 g/L; a yield point of greater than or equal to 1000 poise; and an apparent viscosity of less than or equal to 150,000 centipoise.

In some embodiments of the burn treatment kit all salts present in the first gel formulation and all salts present in the second gel formulation are sodium salts and the gel formulations do not contain any potassium salts or potassium ions.

Further embodiments are directed to methods for mitigating burn injuries to a human using the burn treatment kit as previously described. Such methods may include applying the first gel formulation to a human having acidosis, hyponatremia, hyperkalemia in extracellular blister fluid within 10 minutes after a burn injury occurs, then applying the second gel formulation to the human having alkalosis, hyponatremia, hyperkalemia to a blister that becomes prominent after ten minutes. During the methods, application of the first gel formulation results in mitigation of acidosis, hyponatremia, hyperkalemia; and application of the second gel formulation results in mitigation of alkalosis, hyponatremia, hyperkalemia after blister formation is visible.

According to embodiments of methods for using the burn kits, the first gel formulation includes, per liter of the first gel formulation at 25° C.: from 300 g to 340 g sodium chloride; from $3.5\times10^{-4}$ g to 42 g sodium bicarbonate; from $1\times10^{-6}$ g to 1.3 g sodium carbonate; from $1.2 \times 10^{-1}$ g to 156 g sodium lactate; from $1.15 \times 10^{-2}$ g to 82 g sodium acetate; and from 1.471 g to 420 g trisodium citrate; a gelling agent selected from the group consisting of hydroxy ethyl cellulose, oligomers of cellulose, pectin, carboxy-methyl cellulose, guar gum, and gum arabic, and combinations thereof, and water from a sterilized and deionized source. In such embodiments, the first gel formulation has a pH from 7.45 to 10; a total sodium-ion concentration greater than or equal to 154 g/L; a total bicarbonate-ion concentration from 0.01 g/L to 17.70 g/L; a yield point of greater than or equal to 1000 poise; and an apparent viscosity from 100 centipoise to 150,000 centipoise.

According to embodiments of methods for using the burn kits, the first gel formulation includes, per liter of the second gel formulation at 25° C.: from 80 g to 300 g sodium chloride; from $6.0 \times 10^{-5}$ g to 17.7 g sodium bicarbonate; from $1.0 \times 10^{-6}$ g to $2.3 \times 10^{-4}$ g sodium carbonate; from $1.6 \times 10^{-2}$ g to $7.67 \times 10^{-2}$ g sodium lactate; from $1.53 \times 10^{-3}$ g to $7.2 \times 10^{-2}$ g sodium acetate; from 0.198 g to 0.954 g trisodium citrate; a gelling agent selected from the group consisting of hydroxy ethyl cellulose, oligomers of cellulose, pectin, carboxy-methyl cellulose, guar gum, gum arabic, and combinations thereof, and water from a sterilized and deionized source. In such embodiments, the second gel formulation has a pH from 7.01 to 7.35; a total sodium-ion concentration greater than or equal to 120 g/L; a total lactate-ion concentration from 0.01 g/L to 0.08 g/L; a yield point of greater than or equal to 1000 poise; and an apparent viscosity of less than or equal to 150,000 centipoise. In some embodiments of the methods for using the burn kits, all salts present in the first gel formulation and all salts present in the second gel formulation are sodium salts, and the gel formulations do not contain any potassium salts or potassium ions.

According to embodiments of methods for using the burn kits the first gel formulation comprises sodium chloride in an amount sufficient to mitigate hyponatremia in blister fluids, extracellular fluids, and blood plasma with simultaneous pain management while restoring sodium/potassium ion imbalances from the burn injury. According to embodiments of methods for using the burn kits, the first gel formulation comprises sodium bicarbonate in an amount sufficient to result in mitigating respiratory and metabolic acidosis and SID in blister fluids when pH drops below 7.35 in extracellular fluid and blood plasma with simultaneous pain management while restoring sodium/potassium ion imbalances from the burn injury. According to embodiments of methods for using the burn kits, the first gel formulation comprises sodium lactate in an amount sufficient to result in mitigating metabolic acidosis and SID management in blister fluid, extracellular fluid, and blood plasma. According to embodiments of methods for using the burn kits, the first gel formulation comprises gelling agent in an amount sufficient to prevent hyperkalemia and acidosis in blister fluids, extracellular fluids, and blood plasma by receiving in vitro excess $K^+$ and $H^+$ ions from blister fluids, blood plasma, extracellular fluid, while delivering hydroxyl ($OH^-$) ions from the gel formulation in vivo into the blister fluid, extracellular fluid, and blood plasma to prevent acidosis and sodium ($Na^+$) ions from the gel formulation in vivo into the blister fluid, extracellular fluid, and blood plasma to prevent hyponatremia.

According to embodiments of methods for using the burn kits, the second gel formulation comprises sodium chloride in an amount sufficient to result in mitigating hyponatremia in blister fluid, extracellular fluid and blood plasma with simultaneous pain management while restoring sodium/ potassium ion imbalances from the burn injury. According to embodiments of methods for using the burn kits, the second gel formulation comprises sodium lactate and lactic acid in an amount sufficient to result in mitigating alkalosis when plasma pH increase above 7.45 and SID management in blister fluid, extracellular fluid and blood plasma with simultaneous pain management while restoring sodium/potassium ion imbalances from the burn injury. According to embodiments of methods for using the burn kits, the second gel formulation comprises gelling agent in an amount sufficient to result in preventing hyperkalemia (alkalosis) in blister fluid, extracellular fluid and blood plasma by receiving (in vitro) excess $K^+$ ion; by delivering the stored sodium ($Na^+$) ions in vivo in blister fluid, extracellular fluid and blood plasma.

According to embodiments of methods for using the burn kits, in the first gel formulation, the combination of water, sodium chloride, sodium bicarbonate, sodium lactate, and gelling agent in the gel formulation simultaneously rectifies pH imbalances due to respiratory and metabolic acidosis, expels excess $K^+$ ions in vitro, repletes $Na^+$ ion deficiency in vivo, by restores dynamic physiological $Na^+/K^+$ ion imbalances, and mitigates SID imbalances within blister fluid, extracellular fluid and blood plasma/serum with simultaneous pain management while restoring sodium/potassium ion imbalances from the burn injury. According to embodiments of methods for using the burn kits, in the second gel formulation, the combination of water, sodium chloride, sodium bicarbonate, sodium lactate, and gelling agent simultaneously rectifies pH imbalances due to respiratory and metabolic alkalosis, expels excess $K^+$ ions in vitro, repletes $Na^+$ ion deficiency in vivo by restoring dynamic physiological $Na^+/K^+$ ion imbalances and SID imbalances within blister fluids, extracellular fluids and blood plasma/serum with simultaneous pain management while restoring sodium/potassium ion imbalances from the burn injury.

Having described now the various gel formulations, methods for using the gel formulations, burn kits including a Formulation (I) and a Formulation (II), and methods for using the burn kits to mitigate burn injuries, the various ingredients, their synergies and interactions, and their physiological effects will now be described in detail, along with protocols for preparing the gel formulations according to embodiments.

The human body functions best within a relatively very narrow temperature range (~36-39° C.), provided the cellular homeostasis can be maintained within their usual concentration ranges. Therefore, the core of the body optimally carries out majority of its biochemical activities (transport of materials/ions, thermodynamics, kinetics etc.) within a very narrow and milder temperature ranges within the constraints of normal homeostasis. The self-sustaining activities of human body are carried out via innumerable parallel and consecutive sophisticated biochemical activities/processes by utilizing external food and optimal oxygen ($O_2$) and carbon dioxide ($CO_2$) transport. Even the carbon dioxide ($CO_2$) concentration present in blood and blood plasma released as cellular respiration product also plays a vital role in maintaining the pH (within $7.35 \geq pH \geq 7.45$) at buffered condition at ~37° C. when it forms weak aqueous carbonic acid ($H_2CO_3$) with water. Thus, the kinetics, thermodynamics and the electrophysiology of the biochemical, electrochemical and neurochemical, $Na^+/K^+$ and other ion transport processes across the cell membranes inside the human body preferentially remain self-optimized as long as it receives adequate protection due to the presence of its protective and almost continuous skin layer.

The skin also provides much needed reasonable fortifications even during the small fluctuations in the milder exterior ambient or interior environmental elements in relation to the human body. Skin is the body's largest organ which might apparently seem to be more likely perceived as barely like an organic cellular wrapping paper, however, skin has an assortment of other roles that ranges from protecting and withstanding the external invasion of microorganisms to regulation of the internal body temperature. When the exterior and the interior of the skin gets subjected to excessive heat related exposures (due to accidents/mishaps/injuries), it may not only result in skin damages, it may also trigger severe multiple organ malfunctions in case of severe burn injuries. The skin also has considerable vulnerability, viz., severely damaged skin may heal, but it may not be able regenerate by itself if the burn turns out to be a third-degree burn; which may instead often result in forming undesirable scar tissues. In some cases, the marks from severe burn injuries are not only just cosmetic defects, pervasively formed scar tissues could potentially inhibit movements of a person and/or in general, may lack sweat glands that prevent the body from cooling off due to limited provision for evaporation. These scars seem to be thicker than normal skin; nonetheless, the tissues are essentially weaker in nature.

Although the biochemistry of exterior human skin layer provides smooth and uninterrupted intervention from the extremities of the ambient conditions within a limit, yet, the both exterior and interior skin layer (organic materials) in general, cannot withstand prolonged higher or lower thermal exposure well beyond the optimal operational body temperature, for a longer duration of time. Thus, the exterior protective layer of un-attired human body is the skin layer that only provides protection for the inner core of the biochemistry of the body within a very narrow temperature range. Above or below certain boundary limits of the ambient temperature, the skin layer may sustain skin damages due to the transfer of thermal energy at slow/moderate/elevated rates. Such events consequently may allow transport of external/internal thermal energy deeper into or out of the interior section via the transdermal (skin) route and also may negatively stimulate the nerve endings due to the direct or indirect thermal/colder exposure of the exterior skin layers.

Depending on the length of the thermal exposure with steeper temperature gradient, it may very likely to cause mild to severe skin damages, resulting into moderate to unbearable pain and may disrupt the usual biochemical pathways, viz., triggering ionic, acid/base and aqueous imbalances at vascular, intracellular or extracellular levels. In case of exposure to higher thermal shock or even electrical burn shock, the interior and exterior skin layer may be damaged even when the subjects are covered or protected by everyday outfits (as the regular, everyday attires are often combustible materials). Thus, it is necessary to understand the biochemistry, chemistry, physics, electrochemistry, and neurochemistry of skin layers and the interior organs to devise practical solutions and mitigate organ damages during the aftermath (burn shock) of elevated and/or prolonged thermal exposure. Moreover, it is also critically important to provide simultaneous pain management solutions for speedier pain minimization and patient relief.

Additionally, it is vitally critical to almost instantly prevent and manage excessive aquatic, pH and ionic imbalances across the vicinity of the internal injuries on an immediate basis (within minutes, preferably within the first minute) in case of abnormally high and/or lengthy thermal exposures, followed by initial respiratory (e.g., $CO_2$ inhalation) and metabolic acidosis (lactic acid dissociation in extracellular fluid when lactic is released from the muscle cells during burn injury); followed by subsequent alkalosis ($pH \geq 7.45$) when excess hydrogen ($H^+$) ions (released due to respiratory and metabolic acidosis) move into healthy cells followed by ejection of potassium ($K^+$) ions into the extracellular fluid in addition from cell death/cell lysis and/or tissue necrosis with simultaneous excessive swelling of blister into excessively larger (due to serum/fluid translocation or fluid loss from blood vessels) sizes resulting in edema (serum shifting into the interstitial space in abnormal amount) formation.

Figure 4:
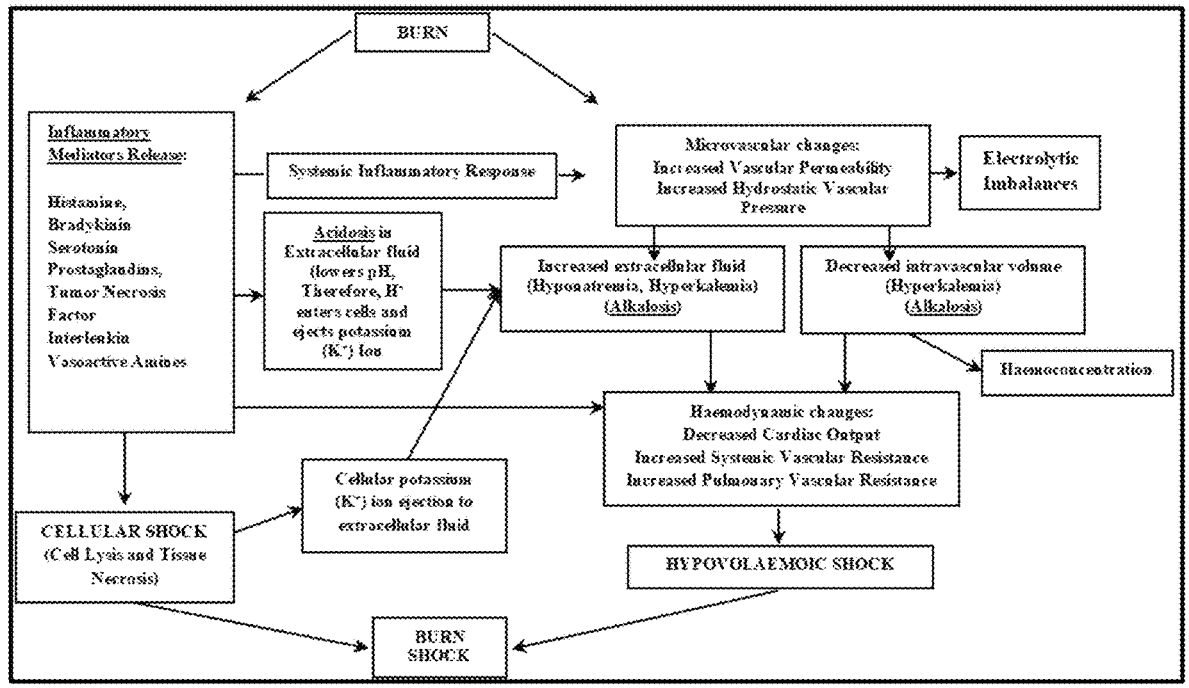
FIG. 4: A flowchart of burn shock with hyperkalemia and hyponatremia in extracellular and intravascular fluids.

The sequence of events from the aftermath of burn and its consequences, i.e., burn shock are shown in the flow diagram of FIG. 4. Cell death could also occur due to various reasons and therefore, could lead to potassium ($K^+$) ions ejection viz., due to cell lysis, tissue necrosis and/or initial acidosis (pH drops) in the blister, edema, intravascular and extracellular fluid. It should be noted that severe hyperkalemia (serum $K^+ \geq 6.5$ mEq/L) is a potentially life-threatening electrolyte disorder that has been reported to occur in 1% to 10% of all hospitalized patients, especially the burn patients and constitutes a medical emergency requiring immediate treatment (See FIG. 6). Therefore, it is indispensable to quickly restore the overall serum potassium ($K^+$) ion levels within the narrow range of tightly controlled between 3.5-5.0 mEq/L levels with minimum time delay, both in intravascular and extracellular fluids to reestablish the regular internal thermodynamic protocols and electrophysiological homeostasis conditions to normalize the organ functionality.

Consequently, it is vitally important to quickly remove the undesirably excess higher concentration of accumulated $K^+$ ions (due to hyperkalemia) in situ via transdermal route before these $K^+$ ions start dispersing across the entirety of the vast, intricate and complex network of the human circulatory system; in parallel, it is also equally important to rectify lower Na ion concentration (hyponatremia, $Na^r$ 135 mEq/L) and also restore pH balances in the plasma and extracellular fluid; all are important for safeguarding and normal functioning of the internal organs, e.g., kidney, heart etc. Simultaneously, it is equally important to almost rapidly minimize the blister formation, their proliferation and swelling. This is realized only if the ion and pH imbalances (hyponatremia, hyperkalemia, initial acidosis etc.) could be slowed down from the very beginning of the burn shock to prevent cardiac arrest ($Na^+$ to $K^+$ ion ratio changes in vascular fluid/blood/extracellular fluid, with abnormally high absolute values of $K^+$ ion) and/or renal failure, when there is an excessive concentration of $K^+$ ion imbalances in vascular and extracellular fluid that surpasses beyond the threshold levels after any severe burn shock injuries (See FIG. 6).

The average normal $Na^+$ ion to $K^+$ ion ratio in blood during regular homeostasis condition is ~140 mEq/L to 4 mEq/L i.e., ~35:1 (35 $Na^+$)/(1 $K^+$). In addition, there may also be a systemic transdermal fluid shift into extracellular or interstitial space causing edema/blister formation during any second-degree burn wounds from severe burn injury. This in turn would lower the $Na^+$ ion concentration in extracellular and vascular serum causing hyponatremia ($Na^+ \leq 135$ mEq/L). Moreover, larger blister formations are highly undesirable as it often leads to the thinning of the skin membrane due to excessive blister swelling and make them susceptible to puncture resulting in fluid, electrolyte and body heat loss through transdermal route.

Additionally, blister puncture may also lead to opening of wound leading to infections, hypothermia i.e., drop in body temperature (due to heat/fluid loss), physical loss of fluid and electrolytes. Blister membrane damage and immediate or subsequent peeling of epidermal skin may also lead to severe discomfort due to the exposure of the nerve endings of the burn patient during recovery period. However, minimal blister fluid inside undamaged blister is necessary to quicken neovascularization during burn wound healing.

Borderline hyponatremia begins when the potassium ($Na^+$) ion concentration reach 135 mEq/L; it aggravates further when the sodium ($Na^+$) ion concentration falls below 135 mEq/L in serum/extracellular fluids. The normal body maintains an extracellular concentration of potassium ($K^+$) ion between 3.5-5 mEq/L including the serum or blood plasma. Borderline hyperkalemia begins when the potassium ($K^+$) ion concentration reach 5.5 mEq/L; it becomes severe as the potassium ($K^+$) ion concentration surpasses 5.5 mEq/L in serum/extracellular fluids. If for some reason, $K^+$ ion levels increase in the extracellular space, i.e., the magnitude of the concentration gradient across the cell membrane (intracellular to extracellular) is reduced and so is the absolute value of the resting membrane potential, thus, raising the membrane potential to its threshold levels, causing disruption of normal functions of neurons, skeletal and cardiac muscles cells. Abnormal shifting of this intracellular to extracellular $Na^+/K^+$ ion ratio and the departure of their absolute values in extracellular fluids are going to have a negative impact on the action potential and depolarization of membrane potential in most cells including myocyte cells, where the action potential changes into flatter rates (See FIG. 7), thus, in many cases reducing the number of $Na^+$ ion channel openings, as they are only activated by the value of the respective membrane potentials at the onset of their respective threshold potentials for the ion channel to open during depolarization stage.

With immediate application of Formulation (I) over the burn injured areas, there would be simultaneous local (in situ) and or (in vivo) diffusion of $Na^+$ and $OH^-$ ions and counter-diffusion (in vitro) of $K^+$ and/or $H^+$ ion, and other anion(s) of sodium salt(s) respectively through the transdermal route, swiftly helps restore the homeostasis (ion balances), initial acidosis and subsequent alkalosis conditions (See FIGS. 8 and 9); which in turn, rectifies the action potentials of various cell functionalities by controlling and correcting the transmembrane potentials and the respective concentrations of extracellular and vascular fluid's potassium ($K^+$) and sodium ($Na^+$) ion concentrations while reestablishing the regular concentration gradient of $K^+$ and $Na^+$ ions across the membranes of skeletal, neural, cardiac and other cells. Thus, these overall actions, especially correcting the transmembrane potential of nerve cells also help reduce pain as a result of burn injury. The speedier restoration is contingent upon how rapidly the gel mixture formulation is applied across the injured surface areas before the highly concentrated local potassium ($K^+$) ions from cell lysis and hydrogen ($H^+$) ions initial acidosis disperses into the vast and intricate network of the circulatory system.

This external application of gel mixture also helps reduce the burden on renal function by excreting higher levels of potassium ($K^+$) ions from extracellular and vascular fluid via (alternate) transdermal route (in vitro); and thus, providing cardiac protection as the overall increase in the concentration of potassium ($K^+$) ions in extracellular/vascular fluid below 5 mEq/L is regulated to repair the action potentials of different varieties of cells by regularizing the transport of sodium ($Na^+$) and potassium ($K^+$) ions across the cell membrane from and to the extracellular fluid and/or vascular fluid and vice versa during the depolarization and repolarization phases of different cells respectively while the transmembrane potentials of neural, skeletal, pace maker and cardiac myocytes cells gets corrected.

During the burn shock, the local concentration of potassium ($K^+$) ions suddenly jumps to abnormally high levels, right after cell lysis, tissue necrosis and initial acidosis in extracellular fluid, followed by possible dispersion of potassium ($K^+$) ions throughout the vast network of the circulatory system, thus, raising the overall concentration of $K^+$ ion in both vascular and extracellular fluids from its normal concentration, thus, misbalancing the overall homeostasis conditions in the extracellular/blister/plasma fluids. Therefore, it is critical to purge out (in vitro) high levels locally concentrated potassium ($K^+$) and hydrogen ($H^+$) ions in blister fluid, plasma or extracellular fluids via an alternate, shorter and local routes; since the excretion of potassium ($K^+$) ion via kidney takes an unusually (~4 hours) long period since the length of the vast network of the circulatory system is very long and thus also jeopardies the renal functions due to high levels of extracellular fluid and higher concentrations of potassium ($K^+$) ion. Therefore, to contain the potassium ($K^+$) ion and hydrogen ($H^+$) ion concentration in plasma within controllable limits, application of this gel mixture formulation on the burn areas and their vicinities is most critical, provided it is applied right from the beginning of burn shock, i.e., before the highly concentrated localized potassium ($K^+$) and hydrogen ($H^+$) ions begins to disperse into the vast network of the circulatory system. The speedy containment of potassium ($K^+$) ion concentration right below 5.5 mEq/L in plasma and extracellular fluid is indispensable to ensure protection of the vital organs (cardiac and renal functions).

Description of the Skin Layer

Figure 10:
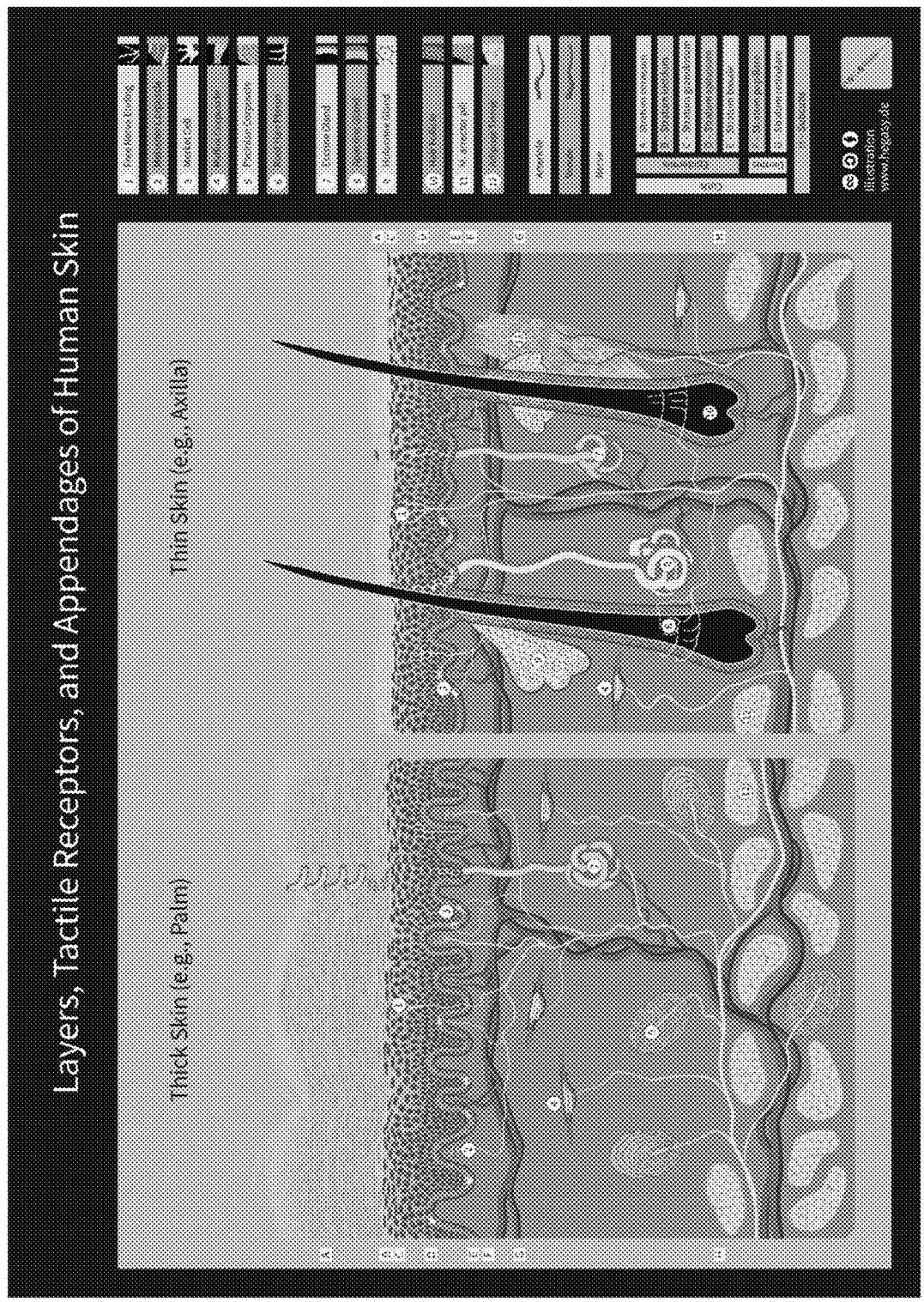
FIG. 10: A diagram of various layers of human skin.

In humans, skin is the largest organ within the integumentary system. The skin has up to seven layers of ectodermal tissue that guard the underlying muscles, bones, ligaments and internal organs; and the primary defense barrier against external pathogens. It is critical to understand the skin layer classification, their functions and the physicochemical impact from the first-degree and second-degree burning. Skin layers are primarily composed of three layers and several other sublayers (See FIG. 10). They are as follows:

1. Epidermis
   A. Stratum corneum
   B. Stratum lucidum
   C. Stratum granulosum
   D. Stratum spinosum
   E. Stratum basale
2. Dermis
   F. Stratum papillare
   G. Stratum reticulare
3. Hypodermis—
   H. subcutis Epidermis and dermis layers together are also termed as "Cutis." The "thick" versus the "thin" skin is almost identical except for the thickness of the exterior layer as shown in FIG. 10.

In addition, there are different biological entities of skin layers with different functionalities. They are as follows:
1. Free Nerve Ending
2. Meissner Corpuscle
3. Merkel Cell
4. Ruffini Corpuscle
5. Pacinian Corpuscle 6. Root Hair Plexus
7. Eccrine Gland
8. Apocrine Gland
9. Holocrine Gland
10. Hair Follicle
11. M. arrector Pili
12. Adipose Tissue In terms of surface area, the skin is the second largest organ in the human body. For the average adult human, the skin has a surface area of between 1.5-2.0 meter squared ($m^2$). The thickness of the skin varies considerably over all parts of the body. An example is the skin on the forearm that is on average ~1.3 mm in the male and 1.26 mm in the female in thickness. The average square inch (6.5 $cm^2$) of skin holds 650 sweat glands (cooling effect, lowering skin pH), 20 blood vessels (for delivering nourishments, $O_2/CO_2$ transport), 60,000 melanocytes, and more than 1,000 nerve endings (sensitivity). The average human skin cell is about 30 micrometer squared ($\mu^2$) in diameter with variants. The area of skin cell usually ranges from 25-40 micrometer squared ($\mu^2$), depending on a variety of factors and locations in human body.

The organization of the above mentioned biological functioning entities and organelles are naturally strategically and systematically structured and placed across the skin layers; while they pervade and repeat laterally in grown up humans skin layers as such that they play a synergistic role to gather localized (inter and intracellular) information via nerve endings, to maintain the integrity and refurbishing the exterior and interior of the skin layers with nourishments during regular situations. Additionally, during and after any anomalous/abnormal incidents or stimulations, viz., from the onset of the burn aftershocks, many consecutive and parallel, preventative damage control biological sequences (events) are activated.

Arteriole and venule are part of blood supply line and are systematically and intricately arranged to crisscross different skin layers to exchange nourishments/toxins, biochemicals, $CO_2$ and $O_2$ to and from various parts of skin cells and layers in those situations. As shown in FIG. 10, nerves also crisscross across the skin layers and nerve endings are present in the upper sublayers of epidermis (hair follicle, Meissner corpuscle, Merkel cell etc.) as well as dermis layers (hair follicle, Ruffini corpuscle, M. arrector Pili etc.). The pain receptors are free nerve endings and are three types of pain receptors, viz., stimuli: mechanical, thermal and chemical.

As skin is the direct interface between the environment and the interior of the human body; it plays the central role in protecting the interior of the body against external elements, providing assortment of sensations, a zone for vitamin D synthesis in the presence of sunlight, protection from terrestrial UV ray (pigmentation) and vitamin B folates, beautification etc. Among other functions, skin provides reasonable thermal or chemical insulation, thermoregulation through heat transfer and evaporation (cooling via heat of vaporization), excretion of sweat biochemicals from sweat gland (eccrine sweat glands, apocrine sweat glands, holocrine and sebaceous glands) openings and their exogenous origins such as metabolites of cutaneous (skin) microflora as end products (free fatty acids), viz., 3-methylbutanoic acid, E-3-methylhex-2-enoic acid, 3-hydroxy-3-methylhexanoic acid, isovaleric acid or 3-methyl butanoic acid etc.).

These are commonly known as body odorants, Therefore, outer skin layer, in most cases, have pH level below neutral (pH~[4-6], avg. 5) due to the transport and conversion (by existing microflora) to an assortment of weaker organic acids taking place on the skin exterior. The skin pH gets regulated by the above-mentioned organic acids/substances, by shifting pH into lower values by their proton-donating properties. Therefore, the pH of the exterior skin is influenced by various substances secreted to the skin surface, like sweat, sebum, and Natural Moisturizing Factor (NMF). Those secretions from the eccrine and sebaceous glands contain additional acids too, e.g., lactic acid, butyric acid, pyrrolidone carboxylic acid (PCA), amino acids, and free fatty acids. Additionally, ingredients of exogenous origin such as metabolites from cutaneous microflora, e.g., released free fatty and cosmetic products may also be present.

Various sweat glands present in dermis and subcutis supply different organic compounds/acids to the exterior of the skin for this microflora to create a lower pH environment (pH 4-6) as metabolites. However, it is apparent that the outside skin pH depends mainly on processes taking place in deeper layers of the epidermis. On the other hand, below the interior of skin layer, in general, the extracellular fluid and blood serum in blood vessel maintain a buffered pH ($7.35 \leq pH \leq 7.45$) condition. However, there is a pH-gradient through the epidermis, changing from acidic values on the skin surface to mildly alkaline (pH ~7.45) condition inside the epidermis. The exterior skin surfaces where the pH environment is substantially lower (in pH~5) help prevent the exterior pathogenic microorganisms' growth that thrive at higher pH ($7.35 \leq pH \leq 7.45$) by inhibiting their growth at the skin exterior of the body and thus are unable to sustain life in that lower pH conditions.

All these actions sequentially unfold in coordination, as a part of the body's defense mechanism scheme-embedded as instructions in the DNA sequence, to control various biochemical activities, viz., skin cell regeneration, UV protection, release of sweat etc. to continuously protect the skin layers from being damaged from the external environmental elements. Likewise, during abnormal thermal/electrical aftershocks, a combination of series and parallel events unfolds to manage damage control of the skin layers and its interior. It is noted that burn shock is a combination of distributive, hypovolemic and cardiogenic shock which begins at cellular levels.

Heat Transfer and Thermoregulation

Heat transfer in general takes place via four different modes, sometimes in various combinations including convection, conduction, radiation, and evaporation (thermoregulation). The complex kinetics and thermodynamic equilibrium of molecular level activity in humans is balanced while it functions within an optimal operating temperature range (avg. ~98.6° F./37° C.). As mentioned earlier, body temperature is primarily regulated through evaporation of water and other biochemical molecules (3-methylbutanoic acid, E-3-methylhex-2-enoic acid, 3-hydroxy-3-methylhexanoic acid, isovaleric acid etc.).

Wind/breeze velocity, shower/bath, humidity, air temperature also plays roles in heat transfer and thermoregulation of body heat via convective and/or conductive heat transfer. During abnormal conditions, excessive thermal energy could be transported or accidentally reach the skin surface via conductive, convective or radiative heat transfer mode alone or in various combinations.

The skin layers and its deeper interior can temporarily hold thermal energy as thermal reservoir to create relatively a very hot/energetic skin surface (to elevate the local surface temperature) and the interior which immediately allows the accumulated heat to dissipate further into the interior of the skin layers causing serious distress to the affected individuals. During the heat transfer from the skin surface to the interior, the accumulated thermal energy is transported either via conduction or convection or in combination. For solids and semi-solid hot skin surfaces, the governing mode of heat transfer primarily take place via unsteady state conductive heat transfer; therefore, the temperature change with respect to time (t) into the interior of the skin layers (z direction, i.e., primarily, normal to the skin surface) is given by the following:

$$\rho C_p \frac{\partial T}{\partial t} = k\nabla^2 T \qquad \text{EQN 1}$$

where: T is the temperature, $C_p$ is the average heat capacity of the semi-solid (skin matter) at constant pressure per unit mass, k is the heat conductivity (assumed constant) and p is the density of the semi-solid body mass. Additionally, for both rectangular and cylindrical coordinates, the energy flux is given by the following equation (in the z direction) by the following:

$$q_z = -k\frac{\partial T}{\partial z} \qquad \text{EQN 2}$$

where: $q_z$ is the heat flux in the z direction or perpendicular to the surface of the skin layers. During heat related mishaps or accidents, the external human skin may endure mild to moderate to severe skin damages due to the direct or indirect exposure of intense and prolonged thermal energy (in addition to external thermal energy carriers, liquid or solid surfaces).

Causes of Burns:

Dry heat (such as fire, hot objects such as hot iron, hot cooking utensils etc.), wet heat (such as steam or hot liquids such as hot beverage, hot soups etc.), radiation heat, friction, heated objects, the sun, electricity or chemicals can all cause burns. Thermal burns are the most common kind of burns encountered in regular work days. These burns occur when flames, hot metals, scalding liquids, or steam come in contact with skin as a result of many different circumstances, including house fires, vehicle accidents, kitchen accidents and electrical malfunctions etc.

As examples, during every day situation, while discharging household chores (hot drink spill, hot water burn etc.), shower malfunctions or professional work, viz., light and heavy duty industrial, utility and commercial duties (steam, hot water, electrical shock etc.), human beings may endure skin damages and consequently observe blister formation as a result of accidents when they get exposed to extreme or elevated thermal energy.

The Symptoms of Burns

The symptoms of burns depend on the cause and type of burn. They can include blisters; pain (the degree of pain is not related to the severity of the burn, as the most serious burns, i.e., the third-degree burns can be painless due to the damage to the nerve endings.); peeling of skin; red skin; shock (symptoms of shock may include pale and clammy skin, weakness, bluish lips and fingernails, and a drop in alertness); swelling; and/or white or charred skin. Therefore, it is important to understand the definition of various degrees of burn.

First-Degree Burn

A first-degree burn is in effect known as a superficial burn or wound that affects only the first layer of the skin. First-degree burns are one of the mildest forms of skin injuries, and they usually may not require medical treatment. They result in pain and reddening of the epidermis (exterior layer of the skin). The symptoms of first-degree burns are often minor and tend to heal after several days. The most common things is noticed at first are skin redness, pain, and swelling. The pain and swelling may be mild and the skin may start to peel off after a day or so. Most first-degree burns can be treated without clinical attention at home or work.

However, for children and infants, the physicians must examine the burn to determine its severity. The physicians should look at the burn to observe how deep it penetrated the skin's layers; if it's large or in an area that requires immediate treatment (within minutes), such as the eyes, nose, or mouth; and if it shows signs of infection, such as oozing, pus, or swelling. One must see the respective physician or specialists if the burn becomes infected, swollen, or extremely painful. Burns on certain areas may require a visit to the doctor on an immediate basis. These burns may heal slower than burns on other areas of the body and require a visit to the physician. These areas include the face, the groin, the anus, the hands, the palms, the feet, and the bottom of the feet. It is critical to observe the total affected area of the burn injury to minimize cosmetic defect and remedial appropriate remedial actions.

Second Degree Burn

Second-degree burns (also known as partial thickness burns) involve the epidermis and part of the dermis layer of skin. Partial thickness burn (PTB) is categorized as superficial partial thickness burn (SPTB) and deep partial thickness burn (DPTB) depending on the thickness of the burn. Burn blisters on the skin are a hallmark of not only SPTB but also DPTB. The burn site appears blistered, show redness, and may become swollen and very painful. In most cases, partial thickness second-degree burns are caused by scald injuries, flames, contact with hot objects, sunburn, chemical burns, and electrical burns. The following are the most common signs and symptoms of a second-degree (partial thickness) burn and symptoms may include blisters, deep redness, wet or shiny appearance of the skin, skin that is painful to the touch, and white or discolored skin in an irregular pattern.

The symptoms of a second-degree burn may resemble other conditions or medical problems. Therefore, in such situations, physician should be consulted for the right prognosis. In case of second-degree burn, it should be ensured that clothing, watches, jewelries near or covering the surrounding burned area must be removed too and encourage drinking plenty of fluids. It is recommended that for best results, profuse and immediate application of the gel mixture formulation (described in the present disclosure) without time delay while covering the burnt area with the mixture, and leaving the mixture on the burn injured areas for a minimum of 30 minutes would help minimize blister formation and pain management.

For severe and ten (10) percent or more burn injury, the gel mixture formulation of embodiments herein may be replaced every 2-5 minutes. However, in case of chemical spill proper medical attention should be sought before applying any ointment or mixture on the surface. If the burn does not show signs of healing within 1 hour, or if it seems to be getting worse, prompt medical care should be sought.

If speedy attention is not provided immediately (within minutes, preferably seconds) of the patient or the affected person at the onset of the burn injury, i.e., right away (with minimal time delays), then the skin damages and blister formation (ion and aquatic imbalances at vascular, cellular and extracellular levels) on the skin surface and subsequently may result into hyponatremia ($Na^+ \leq 135$ mEq/L) and/or hyperkalemia (overall $K^+ \geq 5.5$ mEq/L), with initial acidosis in the extracellular, blister and intravascular fluids; and thereby causing further severe damages to the interior of the skin layers and subsequently destabilize and disrupt various organ functionalities. This could be aggravated if the formed blisters accumulate excessive fluids—resulting in transforming the blister membranes relatively thinner as well as weaker, which in turn, even from minor infractions may cause faster or abrupt rupture of the vulnerable blister membranes that could lead to fluid, electrolyte and body heat loss. Blister may turn out to be further nuisance and cause severe discomfort during transferring patients to the clinic or hospitals or burn units for further treatments.

When the severity of this burn shock is high to begin with—it stimulates the release of inflammatory mediators (e.g. histamine, prostaglandins, thromboxane, nitric oxide etc.) that induces an intense systemic inflammatory response and are responsible for local vasoconstrictions (i.e., the narrowing of the blood vessels) right after the systemic vasodilation (is the widening of blood vessels) which causes increase in the vascular transcapillary permeability (fluid translocation into the extracellular region) in both healthy and the affected tissues. The increased permeability of capillaries triggers an outpouring of fluids from the intravascular (blood vessel) space to the interstitial (tissue) space giving rise to edema. The increase in transcapillary permeability not only results in a rapid transfer of fluid, it also results in simultaneous disbalancing solutes/ions, and plasma proteins between the intravascular and interstitial spaces.

Edema is an abnormal accumulation of fluid in the interstitium (tissue space), located beneath the skin and in the cavities of the body, which usually result in severe pain from the very beginning of the inflammatory phase. On top of that, excessive edema fluid formation is undesirable to prevent body heat loss (due to blister punctures), fluid and electrolyte imbalance when the burn severity and total burn surface area is very high.

Major burn injuries result in an area of necrotic zone, beneath this lies the zone of stasis. This occurs within minutes to hours after injury and is followed by the production of highly reactive oxygen species (ROS) during reperfusion of ischemic (is a restriction in blood supply to tissues, causing a shortage of oxygen that is needed for cellular metabolism) in tissues. ROS are toxic cell metabolites that include oxygen free radicals and cause local cellular membrane dysfunction and transmit an immune response. These short-lived entities are highly unstable reactive metabolites of oxygen; each has unpaired electron transforming them into strong oxidizing agents, viz., superoxide anion ($O^{2-}$) hydrogen peroxide ($H_2O_2$) and hydroxyl ion ($OH^-$) after any inflammatory and reperfusion of ischemic tissues. In the necrotic zone, cell death/cell lysis/tissue necrosis also occurs due to an accumulation of toxic waste products, lack of oxygen and nutrient supply.

As a result of severe burn injury, combination of intravascular hypovolemic shock and cell osmolarity shock is observed, characterized by specific microvascular and haemodynamic changes. Hypovolemic state is the initial state, which immediately (within seconds) begins at the onset of severe burn and lasts for the first up to 48-72 hours when rapid fluid shifts occur from the vascular compartments into the interstitial spaces which may result in twenty percent (20%) or more decreases in the volume of circulating blood/fluid for heart to pump blood in case of severe burn injuries.

Following any significant burn injury (second-degree), with such severe translocations of fluid, electrolytes and other soluble nutrients results in the redistribution of water and solute results in both hypovolemia and haemoconcentration (i.e., in the blood vessels, there is an increase in the proportion of red blood cells relative to the plasma), brought about by a relative decrease in the volume of plasma or relative increase in the concentration of circulating red blood cells. It is critical to point out that a number of homeostatic mechanisms that keep $Na^+$ and $K^+$ regulated at normal or regular conditions. Normal extracellular and intracellular $Na^+$ and $K^+$ ion concentrations are provided in FIG. 1.

The concentration gradient of $K^+$ ions across the cell membranes as well as for $Na^+$ ions could change the threshold potential, the slope of action potentials in membranes as well as depolarization and repolarization rates (slopes) causing severe cardiac dysfunction when the extracellular $K^+$ ion concentration overshoots the maximum safety limit (5.0 mEq/L).

Typical burn injured patient's cell initial acidosis and before hydrogen ($H^+$) infiltration in cellular compartment is shown in FIG. 3. The clinical discourse of burn injury is characterized by an initial shock phase produced by rapid loss of large quantities of extracellular fluid into the injured areas and to a smaller extent towards the intracellular region, i.e., movement of sodium and water into normal tissue cells. This sodium ($Na^+$) ions and fluid shifts into the normal tissue cells which also result in cellular edema and thus, creating hypo-osmolar (hyponatremia) intravascular fluid volume.

For the directly injured cells, sodium ($Na^+$) ion shifts happen due to the change in the transmembrane potential of the cells, increasing ion fluxes rushing them inside resulting in swelling of the cells. Resting (unstimulated) membrane potential describes the steady state potential of the cell membrane for most type of cells except the pace maker cells where resting membrane potential is absent for its complete cycle or period. The membrane potentials vary in a dynamic periodic cycle where the entire process is balanced by controlled $Na^+$ ion pumping (in some cases, additional $Ca^{2+}$ ion channels) during depolarization and ejection of $K^+$ ion during repolarization stage from the cell interior. Resting membrane potential of a cell is estimated by percent averaged equilibrium potential of different individual type of ions crossing the cell membrane.

As different cell membranes have specific ion selectivity in addition to specific voltage gated and non-voltage gated ion channels, the average transmembrane potential are specific for each type of cell membranes and the respective ions crossing the membrane. Without any stimulus, the potential does not change. To get an electrical signal or action potential started, the membrane potential has to change if the stimulus reaches their respective threshold levels (voltage) for further ion channel openings (to begin with $Na^+$ ion channels). It has also been noticed that cellular transmembrane potential in both injured and uninjured tissues decreases involving burn injury due to ionic imbalance.

During burn shock, for skeletal muscle membranes, the transmembrane potential changes from the resting membrane potential (−90 mV) to (70-80 mV) allowing $Na^+$ ions and water entering while subsequently $K^+$ ions leaving the cells. Here, it should be noted that cell deaths occur when the transmembrane potential reaches −60 mV during burn shock which may cause release of relatively highly concentrated intracellular $K^+$ ions into the extracellular fluid. For the nerve cells, the resting membrane potential is −70 mV during normal conditions (See FIG. 2).

During the normal conditions, when any stimulus causes the potential to reach threshold at −55 mV, it triggers an impulse to create action potential, causing the nerve axon's $Na^+$ ion gates to open to rapidly allow $Na^+$ ions to enter the nerve cells and changing the potential to move into the positive territory as shown in FIG. 2. Because sodium ($Na^+$) is a positively charged ion, it will immediately change the relative voltage inside the cell relative to the outside. This starts with a channel opening for $Na^+$ in the membrane and since the concentration of $Na^+$ is higher outside the cell than the inside of the cell by an order of magnitude; thus, ions will rush into the cells. This phenomenon is also largely driven by the concentration gradient of $Na^+$ ion between the extracellular fluids (higher) into intracellular region (lower). The concentration gradient for $Na^+$ ion is so strong that it will continue to enter the cell so that the sodium cation ($Na^+$) entering the cell will cause it to become less negative even after the membrane potential has reached 0 mV.

The electrical gradient also plays a role, as negative proteins below the membrane attract the $Na^+$ ion, eventually the resultant potential would settle at +30 mV momentarily, due to the presence and permeability of other ($K^+$) ions and by this time $Na^+$ ions has ceased entering the nerve cells. This increase in potential towards positive direction during this period is known as the depolarization phase. At this point, the voltage gate for $K^+$ ion is opened to allow $K^+$ ions to leave the cells due to the increased repulsion between $Na^+$ and $K^+$ ions which occurs due to their increase in the cells interior voltage. After exiting the cell, the $K^+$ ions reach its equilibrium (−93 mV) for $K^+$ ions; dipping its membrane potential well below its resting membrane potential (−70 mV). This state is known as the hyperpolarization phase (See FIG. 2). At this point, the two $K^+$ ions move in and three $Na^+$ ions move out from the cells eventually settling at the resting membrane potential at −70 mV. However, with capillary fluid leakage from blood vessels, the concentration of $Na^+$ ion gets lowered in extracellular fluid due to the dilution effect, resulting in hyponatremia ($Na^+ \leq 135$ mEq/L).

During the burn shock, with hyponatremia condition existing in extracellular fluid during the depolarization phase, the rushing of $Na^+$ ion inside the cells are slowed down due to also the smaller concentration gradient of $Na^+$ ion, resulting in slowing/flattening the rate of change of the action potentials. The risk factors for prolonged hyponatremia ($Na^+ \leq 135$ mEq/L) in extracellular fluid include liver failure, heart failure, myocardial infarction, and endocrine changes.

Hyponatremia in extracellular fluid is associated with various conditions that can be grouped into disorders, characterized by dilution as a result of water intake in excess of output; (the condition implies impaired water excretion) and disorders caused by sodium depletion in excess of water depletion or replacement of fluid losses with water alone). As a result, without adequate and prompt restoration of fluid volume or fluid deficits results in hyperdynamic circulatory state (abnormally increased circulatory volumetric flowrate) that results from severe hypermetabolism (i.e., the physiological state of increased rate of metabolic activity and is characterized by an abnormal increase in the body's basal metabolic rate). Depending on the magnitude of the injuries, these changes, together with increased vascular resistance and the decreased cardiac contractility produced by tumor necrosis factor (TNF) (cell signaling protein, cytokine and interleukin-1 to provide inflammatory responses) release can trigger a state of shock (involved in systemic inflammation and is where one of the cytokines triggers the acute phase reaction). A local increase in concentration of TNF will cause the principal signs of inflammation to occur, i.e., heat, swelling, redness, pain and loss of function.

Insensible fluid losses because of the severely burned skin are increased fourfold to tenfold above normal, while renal handling of water is impaired by high and sustained secretion of antidiuretic hormone. The continuing adrenocortical response also results in excretion of large quantities of potassium ($K^+$) ions into the extracellular fluid. Therefore, when a sudden deterioration in the patient with thermal injuries is encountered, adrenal insufficiency must also be considered.

Acute adrenal insufficiency (AI) is an uncommon disorder among critically ill (severely) burn patients, which can often go unrecognized. Therefore, because of this abnormal situation, departure from usual homeostasis of sodium ($Na^+$) and potassium ($K^+$) ion balance occurs, especially in the extracellular and intravascular fluid. The normal homeostasis is critically indispensable to the sustenance of life, i.e., proper functioning of the organs, therefore, it is critical to restore and maintain the extracellular sodium ($Na^+$) and potassium ($K^+$) ions back to normal levels as early as possible.

Figure 11:
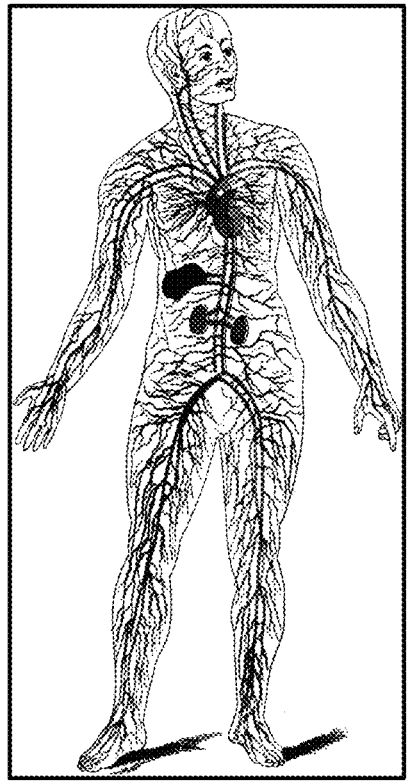
FIG. 11: A simplified schematic of the human circulatory system.

Tissue necrosis or cell lysis or major cell death can lead to the release of intracellular $K^+$ (140 mEq/L) to infiltrate into extracellular fluid causing a disorder in $K^+$ homeostasis due to the abnormal increase in the $K^+$ ion within local extracellular/blister fluid. Therefore, as the potassium ($K^+$) ions leaks out of cells in hypertonic states during burns and injuries, therefore, there is the redistribution of $K^+$ ions shifting from the intracellular space into the local extracellular space followed by further dispersion of the potassium ($K^+$) ions throughout the vast network of the circulatory system (See FIG. 11), thus, the overall potassium ion concentration in the extracellular fluid and/or serum gets elevated (to $K^+ \geq 5.5$ mEq/L) leading to hyperkalemia. Moreover, potassium ($K^+$) ions are also forced out of the cells in exchange for hydrogen ($H^+$) ions due to respiratory acidosis (e.g., $CO_2$ inhalation). Therefore, it is critically important to thrust back part of expelled (via cell lysis or tissue necrosis, metabolic and respiratory acidosis) potassium ($K^+$) ions from the blister/extracellular and intravascular fluids into the intracellular compartments by restoring the local buffer pH as fast as possible.

Serum potassium ($K^+$) ion concentration in such fluids can be restored by two general mechanisms: the first is by shifting potassium intracellularly using agents such as insulin, albuterol or intravenous addition of sodium bicarbonate. Therefore, in vitro application of gel formulation mixture according to embodiments, comprised of sodium bicarbonate based ($NaHCO_3$) pH control would help thrust back excess potassium ($K^+$) ion from blister, edema, extracellular and intravascular fluids into the interior of the cells by reversing local acidosis as bicarbonate ions diffuses into the fluids and/or hydrogen ($H^+$) ions present in the blister/extracellular fluids move out to the gel formulation matrix (in vitro) via transdermal route, consequently neutralizing themselves by reacting with hydroxyl ($OH^-$) ions present in the gel matrix Formulation (I).

From a scientific standpoint, there are at least five areas of concern with potassium ($K^+$) ion concentrations of 5.5 mEq/L and above: (1) abnormal membrane potentials/voltages and cellular ionic imbalances during global ischemic arrest and regional ischemia during reperfusion; (2) coronary vasoconstriction of varying degrees, loss of myocardial protection and possible vascular spasm; (3) activation the coronary vascular endothelium to become leaky, pro-inflammatory and promotes platelet aggregation; (4) post-operative arrhythmias and conduction disturbances; and (5) a higher incidence of low cardiac output from ventricular stunning.

Hyperkalemia in serum is characterized by irritability, nausea, decreased urine production, and cardiac arrest. Hyperkalemia (overall $K^+ \geq 5.5$ mEq/L) arrests the heart in diastole due to higher concentration of potassium's ($K^+$) ability to reduce the availability of "open" fast channels for $Na^+$ ions, which are responsible for the rapid Phase O upstroke (depolarization) of the cardiac action potential. With hyperkalemia, the resting membrane potential becomes less negative; therefore, during the initial phase of hyperkalemia it is easier to induce stimuli. The excitability is increased, arrhythmias can occur, patients can have paresthesia. During severe hyperkalemia, the although the membrane potential is even less negative, several sodium ($Na^+$) ion channels stay inactive and second phase of hyperkalemia comes with muscle weakness, paralysis, bradycardia and QRS widening on ECG. In case of extreme hyperkalemia, the whole process can end with ventricular fibrillation or the heart stops in diastole (asystole).

Figure 7:
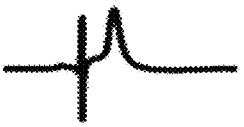
FIG. 7: A diagram showing extracellular concentrations of potassium ($K_e^+$) ions results in the classic electrocardiographic changes.
Figure 12:
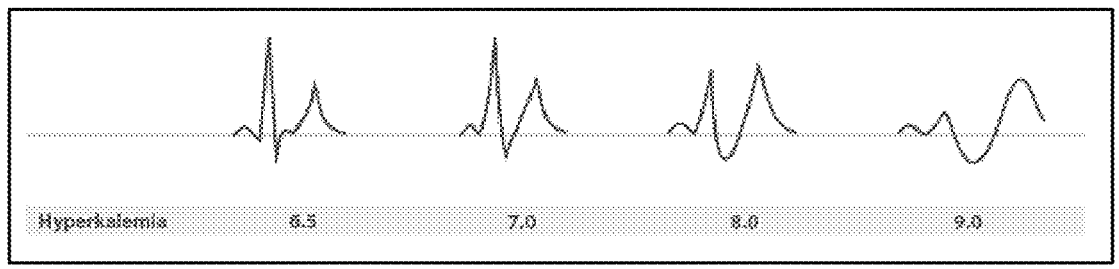
FIG. 12: A diagram of the severe changes in the electrocardiogram is observed when the case hyperkalemia becomes very pronounced.

FIG. 12 shows how the myocardial action potentials change due to hyperkalemia, as captured from the abnormalities in the electrocardiogram, i.e., the changes in the action potentials with respect to increased potassium ($K^+$) ion concentration in extracellular and serum can lead to cardiac failure (See also FIG. 7). Therefore, the action potentials for both pace maker cells and cardiac myocytes and their corresponding depolarization and repolarization phases needs to be guarded with respect to the increase in the excess potassium ($K^+$) ion concentration in the extracellular region which affects the membrane potentials and action potentials. Here, the equilibrium potential $Ca^{2+}$ (123 mV), $Na^+$ (67 mV), and $K^+$ (−92 mV) ions and their concentration levels in extracellular fluid determine the resultant transmembrane potential, which in turn, play significant roles in depolarization, repolarization and opening and closing the voltage gated channels as the action potential changes and reaches their corresponding threshold values. Therefore, wider and prolonged departure of ion concentrations from normal homeostasis condition across cell membranes imbalances the normal functioning of vital organs.

For example, with increased $K^+$ ion (overall $K^+ \geq 5.5$ mEq/L) concentrations in extracellular fluid, this may appear that there is an increase the myocyte excitability; however, raising the membrane potential near the threshold potential will not allow opening as many voltage operated $Na^+$ ion channels that is required to raise the potential inside the cells. Therefore, it is critical to note that the value of membrane potential at the onset of action potential determine the activation of the number of $Na^+$ ion channels, thus the number of available $Na^+$ ion channels decreases if the resting membrane potential gets elevated to higher level than usual situation; this happens due to the increase in $K^+$ ion concentration in the extracellular fluid during the depolarization phase. On top of that, to add insult to the injury, there is further slowing down of the influx of sodium ($Na^+$) ion due to hyponatremia ($Na^+ \leq 135$ mEq/L) in extracellular fluid, i.e., when the $Na^+$ ion concentration gradient across the cell membranes due to the fluid leakage; consequently, resulting in slowing or flattening the action potential impulses to cause conductions delays.

Additionally, hyperkalemia causes anomaly during the repolarization inside the myocytes and also causes conduction delays due to the lower magnitude of $K^+$ ion concentration gradient across the myocyte membranes. On the same note, the lower concentration of $Na^+$ and $K^+$ ions in extracellular fluid would also negatively affect the action potentials of neurons, skeletal muscles and cardiac muscles during the depolarization and repolarization of the cell membranes.

It should be noted that there is no resting potential for pacemaker cells and as it reaches −60 mV during repolarization phase and immediately jumps to the depolarization phase due to the opening of $Na^+$ ion channel to reach −40 mV potential, followed by opening of the opening of voltage gated $Ca^{2+}$ ion channel to elevate the potential to +10 mV. This is followed by repolarization phase when the voltage gated $K^+$ ion channels open to eject the $K^+$ ions outside the cell and the process repeats itself. Here, for the pacemaker cells, $Na^+$ and $Ca^{2+}$ ions play their respective roles during depolarization and $K^+$ ions during repolarization phases.

On the same note, during regular conditions, the concentration levels of $Na^+$, $Ca^{2+}$, and $K^+$ ions across the membranes play their respective roles during depolarization and repolarization phases for cardiac myocytes; in this case, the resting membrane potential reaches ∼−90 mV and the cycle is repeated during normal conditions. Although the depolarization of myocytes is complicated, as predominantly $Na^+$ ion enters the cell as the potential reaches +20 mV from −90 mV, followed by simultaneous opening of the $Ca^{2+}$ and $K^+$ ion channels, balancing the potential at 5 mV. This is followed by repolarization phase when the $K^+$ ion channels open to eject the $K^+$ ion outside the cell.

However, when there is severe burn injury, the freshly developed hyperkalemia in the extracellular fluids, the action potentials deviate from the norm during the depolarization phase due to hyponatremia ($Na^+ \leq 135$ mEq/L) and rise in the membrane potential due to hyperkalemia. This is followed by the repolarization phase when it encounters uphill battle to eject the $K^+$ ion against the smaller concentration gradient of $K^+$ ions due to the increase in the relatively higher concentration of $K^+$ ion in the extracellular fluid, while the transmembrane potential attempts to lower itself towards its resting membrane potential (the usual resting potential ∼−90 mv for myocytes, lowest potential for pace maker cell ∼−60 mV) due to the fact it encounters abnormality in $K^+$ ion concentration in extracellular fluid during the depolarization phase; thus jeopardizing the cardiac output. Additionally, with increased accumulation of $K^+$ ions in the intravascular and extracellular fluid, the decreased excretion of $K^+$ ions via kidney with the presence of excess fluid may also lead to renal failure.

It is important to note that the kidney has a relatively sluggish ability to excrete a potassium ($K^+$) load, as it takes about 4 hours to reestablish total potassium ($K^+$) body balance. Therefore, also due to the abnormally high levels of $K^+$ ions (hyperkalemia) in the extracellular and vascular fluid, hemodynamic changes occur due to may result in an acute circulatory failure leading to multiple organ failures. Thus, during the hypovolemic shock period resulting from severe thermal burn injury, it is indispensable to immediately apply one or more effective and novel (best within seconds/minutes) post-resuscitation action(s) to control these life-threatening problems associated with fluid management, electrolyte imbalances and pain management as an instant (within seconds/minutes), preventative and mitigating solutions which are not always readily available.

Alternatively, the formulations of the present disclosure provide speedier relief and quicker protection of organs in comparison with the conventional burn remedies. Conventional post-resuscitation (resuscitation is the process of correcting physiological disorders) is the management of intravascular and extravascular fluid volumes, increased water requirements, restoring to normal homeostasis condition ($Na^+$ and $K^+$ ion balance) etc. Post-resuscitation and the management of minor ions (calcium, magnesium, potassium, phosphates, etc.) require a workable understanding of the basic pathophysiology of the burn injury, the complex interaction with treatment regimens/procedures, and the differences interposed by age and associated disease.

It should be noted that effective internal (intravenous or oral or enteral) or external post resuscitation are usually not immediately (within minutes) available due to logistical issues, immediate unavailability of administering personnel, lack of availability of "off the shelf" fluid/ion management medication etc. Therefore, since during the initial period burn shock (within minutes), the conventional medical intervention (e.g., administering of intravenous fluids) practiced by medical professional may not be promptly available (in minutes) due to logistical reasons, which in turn, could lead to unrestrained increase in hyponatremia ($Na^+ \leq 135$ mEq/L) and/or hyperkalemia (overall $K^+ \geq 5.5$ mEq/L) in the extracellular and intravascular fluids, leading to out of control blister formation, edema formation and hyperkalemia, thus, further aggravating the injury.

Initially, large volumes of isotonic solutions are required and which is in general administered via intravenous regimen to treat and/or prevent burn shock during post-resuscitation. However, in general these remedies are not accessible within minutes and in many cases, even if the hospitalization is made available after an hour or so, therefore, it may be too late for the severely burnt patients. Additionally, the initial respiratory acidosis (pH$\leq$7.35) during burn shock is rapidly replaced by a respiratory alkalosis, which becomes a mixed alkalosis (pH$\geq$7.45) when excess hydrogen ($H^+$) ions released from carbonic acid ($H_2CO_3$) and/or lactic acid dissociation from metabolic acidosis (from muscle/skeletal/metabolic cells) in extracellular fluid finds their way into intracellular compartments; expelling potassium ($K^+$) ions from the cells and when these potassium ($K^+$) depletion from the cells remains unchecked.

During initial acidosis, opposite action happens, when the pH is compensated by transferring hydrogen ($H^+$) into the cells, ions of $K^+$ are in exchange released into the extracellular/plasma fluid. On the other hand, during subsequent alkalosis, when the extracellular fluid has lack of protons (H), $H^+$ emerges from the cells in exchange for $K^+$ (if positive $H^+$ ion exits from the cell, and then it must be replaced by another positive ion). In the same context, insensible water losses through blood vessels are increased fourfold to tenfold above normal, while renal handling of water is impaired by high and sustained secretion of antidiuretic hormone. The continuing adrenocortical response results in excretion of large quantities of potassium ($K^+$) ions.

Therefore, when a sudden deterioration in the patient with thermal burn injuries is encountered, adrenal insufficiency must also be considered. At this point, very large blister formation with pronounced swelling may cause skin to become excessively vulnerable which is highly detrimental for maintaining skin integrity. Although, studies have found that blister and its fluids play roles in regenerating new skin formation and prevent further damage to the interior of the skin layers. Therefore, the knowledge of blister fluid and its chemistry is vital to minimize the volume of the blisters, manage pain, prevent transdermal fluid loss and minimize damage of the skin.

Blister Fluid Composition

To understand the pathophysiology of burns and its effective and immediate (within minutes) remediation, it is important to understand the blister chemistry, its composition, thermodynamic behavior, viz., ionic equilibria, potassium ($K_i^+/K_e^+$) ion balance and pH shifts during the burn shock. It has been repeatedly demonstrated that suction blister fluids (SBF) have similar composition as human serum composition, although the burn blister (BBF) fluid composition would deviate from SBF composition due to pH and ion imbalances.

The average sodium ($Na^+$), potassium ($K^+$) and chloride ($Cl^-$) ion composition of blister fluid are ~140, 4.4 and 112 mEq/L respectively, versus the sodium ($Na^+$), potassium ($K^+$) and chloride ($Cl^-$) ion composition of serum are ~141, 4.3 and 108 mEq/L respectively in one study. It is possible that since chloride ($Cl^-$) ion is not numerically balanced or matched with total positive counter ions, the sodium ($Na^+$), potassium ($K^+$) ions; therefore, it is very likely that the excess sodium ($Na^+$) ions may be getting transported along with one of the buffer components, viz., sodium bicarbonate ($NaHCO_3$) after a while. Sodium bicarbonate ($NaHCO_3$) is one of the buffering components of plasma/serum with aqueous carbon dioxide ($CO_2$) to form aqueous carbonic acid $H_2CO_3$. The same study found out that low molecular weight organic acids, fatty acids, carbohydrates, amino acids etc. and serum like proteins are also present in the blister fluid although 25% or one fourth of the present in the serum concentration.

Interstitial fluid (ISF), that surrounds the cells and tissues of the body has molecular components similar to plasma as well as compounds produced locally in tissues. The suction blister fluid (SBF) largely consists of ISF indicating that both are similar in their properties. They collected SBF from 10 human volunteers and after analyzing the samples using untargeted high-resolution metabolomics (HRM), they were able to detect a wide range of metabolites were in SBF, viz., including amino acids, lipids, nucleotides, and compounds of exogenous origin. Various systemic and skin-derived metabolite biomarkers were found at elevated levels or found uniquely in SBF, and many other metabolites of clinical and physiological significance were well correlated between SBF and plasma although, ISF has lower concentrations of high-abundance proteins like albumin and globulin which are prevalent in plasma.

The interstitial fluid (ISF) or extracellular fluid constitutes 60% of total body fluids in humans. ISF must be explored further as a matrix for biomarker detection to effectively utilize its potential to stabilize the system from the beginning of the burn aftershock. Extracellular fluid or ISF, which nourishes (transporting nutrients), scours (metabolic waste) and surrounds cells and tissues of the body, is formed as plasma traverses blood vessels and equilibrates with the cell and tissue environment by means of thermodynamic chemical potential while simultaneously creating an environment for intercellular and neural communication. Since extracellular fluid or ISF interacts directly with intracellular fluid, it is possible that compounds that cannot be detected in plasma may be detected in ISF.

The effect of burn blister fluid in neovascularization during burn wound healing is not completely known due to limited number of studies. Burn blister fluid (BBF), containing a large amount of chemokines (signaling protein), is thought to play a role in the early stage of neovascularization. It should be noted that BBF has also severe ion imbalances due to burn shock and expected to have similar ion concentration as the extracellular fluid or ISF. Therefore, BBF and SBF are not numerically identical in terms of potassium (K$^+$) and sodium (Na$^+$) ion concentrations. This process includes angiogenesis (formation of new blood vessels from preexisting vessels) and vasculogenesis (blood vessel formation by the production of endothelial cells).

Because of different healing time of burn wounds, researchers hypothesized that neovascularization in superficial partial thickness burn (SPTB) and deep partial thickness burn (DPTB) wounds are different. However, increased time for healing may be due to the excessive damage due to DPTB. Burn blisters on the skin are a hallmark of not only SPTB but also DPTB.

The neovasculogenic effects of two different burn blister fluids were also noted to be different by researchers. It was found Day 7 DPTB wounds had a significant increase in blood vessels compared with SPTB wounds by immunohistochemistry. DPTB blister fluid significantly promotes neovascularization by increasing endothelial cell multiplication, migration and differentiation of circulating angiogenic cells relative to SPTB blister fluids. In the animal study, DPTB blister fluids markedly promoted new blood vessel formation compared with those from SPTB blister fluids using in vivo Matrigel plug assay. These results suggest that DPTB wounds require more new vessel formation than SPTB. Furthermore, the measurement of angiogenic activities in burn blister fluids serves as a possible tool for assessing burn wound status.

Burn wound healing is a complex and dynamic process, which involves an interaction between different cells and mediators. This process can be divided into inflammatory phase, proliferative phase and remodeling phase. It is noted that neovascularization begins during the inflammatory phase of wound healing and also is recognized as an imperative stage of wound healing and precedes re-epithelialization. The whole process consists of not only angiogenesis, i.e., the formation of blood vessels from preexisting vessels, but also adult vasculogenesis, the formation of vessels from the recruitment and differentiation of circulating angiogenic cells (CACs). Superficial partial thickness burn (SPTB) heals within 2 weeks without scarring. Deep partial thickness burn (DPTB), on the other hand, healing takes place in more than 2 weeks and requires aggressive treatment to prevent hypertrophic scarring (HS).

Although neovascularization plays a crucial role in burn wound healing, the effect of burn blister fluids on the neovascularization has not been fully studied. Circulating blood cells were observed in burn blister, suggesting a positive role of blister fluid in the recruitment and activation of blood cells. Although burn wound outcomes are quite different in terms of burn depth, no studies ever examined the differential neovascularization between SPTB and DPTB wounds. Burn blister, occurring early in burn injury, may be responsible for neovascularization of burn wound healing.

Types of Pain during Burn Injury:

Procedural Pain: (e.g., primary mechanical hyperalgesia) is the most intense and most likely type of burn injury pain which remains undertreated. Patients describe procedural pain as having an intense burning and stinging quality that may continue to a lesser degree but may be accompanied by intermittent sharp pain for minutes to hours after dressing changes and physiotherapy have ended.

Background Pain: Burn-injured patients with high anxiety also tend to report more background pain. Similar to procedural pain, wide variability has been documented in the intensity of background pain after burn injury. Background pain is characterized by its prolonged duration, relatively constant nature, and mild to moderate intensity. Burn background pain is typically described as a continuous "burning" or "throbbing" pain that is present when the patient is relatively immobile.

Breakthrough Pain: Similar to postoperative patients, patients with burns experience transient worsening of pain most frequently associated with movement that is referred to as breakthrough pain. Burn-injured patients also describe spontaneous components of breakthrough pain. Spontaneous breakthrough pain may be due to changing mechanisms of pain over time as well as inadequate dosing, which occurs when serum blood levels of analgesics drop below what is needed to control background pain. Spontaneous breakthrough pain is commonly reported by patients in qualitative terms, viz., "stinging," "pricking," "shooting," and "pounding".

External Treatment

'Hypertonic Saline Soaking Therapy' (HSST) has been used to treat small-area skin wounds, particularly burns, with hypertonic saline mixed with local anesthetic to manage the pain. However, saline solution slow under gravity, therefore, it is difficult to keep the saline solution remain immobilized over the burn injured areas. HSST applies to hypertonic saline not only at the stage of granulation edema but also at the beginning of the treatment, without causing infiltrative edema or infection.

The concentration of hypertonic saline used initially ranged from 5% to 10%. With their experience, however, they set the concentration at 3%. 0.2% lidocaine hydrochloride was used on the wound surface to relieve pain, and the overall effect was satisfactory. Lidocaine is a rapidly effective amide topical anesthetic. It can stabilize the electric potential of cytomembranes, improving cell metabolism; low concentrations of lidocaine are less toxic and can dilate capillaries, improving microcirculation of the wound surface. However, it is unable to restore $K_i^+/K_e^+$ balances, initial acidosis and subsequent alkalosis and rectify the electrophysiology of various cells governed by narrow ion balances. Medium- and small-area burns are the most common, so these concentrations are suitable in most cases.

It is important to note that HSST never treated large-area burns by this method, but for such wounds a reduction in the concentration of sodium chloride to 1-1.5% was considered and a similar reduction in the concentration of lidocaine; in their experience, a dosage of less than 400 mg lidocaine was considered safe for external use. This treatment with low concentration of sodium chloride solution may be detrimental to larger area burn because Na$^+$ and Cl-ion may also accompany infiltration of water molecule inside the edema or blister fluid due to the high concentration of water in the solution and swell the blister fluid. In addition, for larger area burn, it is difficult to submerge large burn areas or when different parts of the body have islanded affected areas along the body while keeping the solution immobilized on the skin surface due to the lower viscosity (fluidity) of saline water. Some experts worry that the wet compress of hypertonic saline may cause hypernatremia (Na$^+$≥145 mEq/L) and hyperchloremia, however, as 10% sodium chloride is given intravenously in the treatment of cerebral edema, it should be safe to apply 3% saline externally; electrolyte disorder should also be regulated in the course of holistic treatment.

Bogart et al. (U.S. Pat. No. 5,271,943) presented three gel mixture formulations comprised of sodium chloride (NaCl), gelling agent and sterile water (pH~6.8) with three different levels of salt concentrations to nurse and heal any kind of open wounds including infected burn wounds. According to the inventors, the purpose of using water is to create moist environment and create gel formation. Bogart et al. (U.S. Pat. No. 5,271,943) asserts that no cationic gelling agents should be used whereas the present disclosure proposes cationic (only $Na^+$ and never $K^+$ ion substituted) and non-crosslinked gelling agents may be used as gelling agents to prevent film formation over burn injured areas that would eliminate any barrier formation during sodium ($Na^+$) and potassium ($K^+$) ion transport across unopened transdermal routes. These three formulations in (U.S. Pat. No. 5,271,943) are hypertonic ($\geq$40 wt %), isotonic (0.9 wt %) and hypotonic (0.5 wt %) in sodium chloride (NaCl) concentration and these formulations serve different purposes. However, they emphasized that pH of their formulation should around 6.8. They also point out that the concentration of gelling agent should be less than 4 wt % or so. In the present disclosure, the gelling agent concentration may well exceed 4 wt % since the polydispersity index and degree of polymerization of natural polymers as gelling agents may be variable in nature.

Bogart et al. (U.S. Pat. No. 5,271,943) emphasizes that these formulations are applicable for already infected open wounds and never mentioned that it should be used at the onset of burn shock injury. Bogart et al. (U.S. Pat. No. 5,271,943) intends to deliver sodium chloride (NaCl) salt inside the open wound and conform to the interstices of the wounds; which is contrary to the present disclosure i.e., to prevent hypernatremia and stinging pain to the patients caused by sodium chloride infiltration through the open wound. The hypertonic salt formulations (Bogart et al, U.S. Pat. No. 5,271,943) are applied at the beginning inside the infectious open wounds to kill bacteria in the wound bed itself and to clean bacterial infections, remove exudates, eschars, and debris. In addition to the bactericidal property, the hypertonic formulation of U.S. Pat. No. 5,271,943 is also intended for softening, liquefying and sloughing off the eschars and should remain for "some time" and initiate drainage from the wound. Ironically, it is well known that at the later stages of burn shock injury, external fluid drainage is not recommended for any total large burn surface area (TBSA$\geq$10-20%) that would aggravate hypovolemic shock and thereby causing damage to the vital organs (heart and kidney).

In the present disclosure, it is intended to use Formulation (I) to minimize blister formation, prevent hypovolemic fluid loss and minimize blister fluid proliferation thereby proactively reverse wound opening from blister puncture or blister rupture to subsequently prevent or cause any drainage. Therefore, for large total burn surface area ($\geq$10-20% TBSA), it is highly undesirable to initiate any hypovolemic fluid loss from patients' interior of the body that risks the lives of the patients through huge fluid loss and hypothermia via open wound. Therefore, application of such hypertonic formulation (U.S. Pat. No. 5,271,943) is not fit for patients with large TBSA ($\geq$10-20%) with open wounds. They (Bogart et al, U.S. Pat. No. 5,271,943) also leave it open to use other dressings over their applied formulations over the open wound to soak debris, dead bacteria, exudates etc.

Bogart et al. (U.S. Pat. No. 5,271,943) acknowledges that hypertonic formulations are physiologically incompatible and cytotoxic in nature and can potentially harm or kill any healthy cells when they infiltrate in the human body. Therefore, it was recommended by Bogart et al. (U.S. Pat. No. 5,271,943) that hypertonic gel mixture formulation needs to be removed to prevent physiological incompatibility that may kill healthy cells before applying isotonic and hypotonic ($\geq$0.4 wt % and $\leq$0.9 wt %) gel mixture formulations to deliver medications. In addition, this recommendation may be further ineffective (or may be harmful in case of severe burn injury) if prolonged application of their formulation is maintained for long hours (8) which may cause hypernatremia and excessive fluid loss due to wound opening near blisters. After removing hypertonic gel mixture formulations from open wound, it was recommended by Bogart et al. (U.S. Pat. No. 5,271,943) that the isotonic and hypotonic gel formulations should be used for delivering medications inside the open wounds. Again, for large TBSA ($\geq$10-20%), the application of hypotonic gel mixture formulations (in U.S. Pat. No. 5,271,943) with lower pH (6.8) in open wound may aggravate fluid loss, cause ion and pH imbalances in extracellular fluids which is highly undesirable for large TBSA ($\geq$10-20%).

Bogart et al. (U.S. Pat. No. 5,271,943) also creates the gel mixture formulations with buffering ingredients to maintain pH6.8. Application of lower pH formulation on burn wound create acidosis or acid imbalance no matter whether it is applied on open or closed wounds. On the contrary, the present disclosure uses two gel mixture formulations; Formulation I with pH control agents present creates pH8.5 or higher (up to pH 10) rectify the initial acidosis in the extracellular fluid and the Formulation II uses pH control ingredients to create pH level between 7.01$\leq$pH$\leq$7.35 to rectify subsequent alkalosis if there is a delay in applying the Formulation I at the onset of burn shock injury.

Moreover, Bogart et al (U.S. Pat. No. 5,271,943) also allows the use of buffer components comprising of potassium (K) salt mixture. This in effect would aggravate hyperkalemia or preexisting hyperkalemia for burn injured patients once potassium ($K^+$) ions starts infiltrating inside the body when the formulations of Bogart et al (U.S. Pat. No. 5,271,943) remains applied for 4-8 hours. On the contrary, in the present disclosure, it is strictly prohibited to introduce any potassium (K) salt or potassium ($K^+$) ion-based pH control ingredients to create desired pH levels in both the gel mixture Formulations (I and II). Therefore, Bogart et al (U.S. Pat. No. 5,271,943) formulation would aggravate hyperkalemia and acidosis (due to low pH in their formulation) when applied on burn injured patients as a result or other injuries.

In addition, Bogart et al (U.S. Pat. No. 5,271,943) also proposes edema fluid out of burn injured areas whereas in the present disclosure, the blister fluid expulsion is discouraged from the wound or blister while the Formulation I and II is applied on unopened wound/blisters which helps the edema or blister fluid to get back to vascular region or cell interiors and avoid fluid loss as such that it would prevent life threatening situation (hypothermia and hypovolemic shock) for patients' with $\geq$10-20% TBSA.

Bogart et al (U.S. Pat. No. 5,271,943) encourages the use of their formulations long after the injury has occurred, i.e., when the wound is already infected and leave them applied between four to eight (4-8) hours; whereas in the present disclosure, it is most propitious to apply the formulations at the onset of burn injury and replace them every 3-5 minutes with fresh formulations to minimize blister formation, prevent hypovolemic fluid loss, rectify pH imbalance and prevent hyperkalemia and hyponatremia.

Internal (In Vivo) Treatment

Fluid Management (Conventional Intravenous Treatment)

The goal of conventional fluid management in major burn injuries is to maintain the tissue perfusion (passage of fluid through the circulatory system) in the early phase of burn shock, in which hypovolemia initially occurs due to steady fluid extravasation from the intravascular compartment.

Current approaches to fluid management are to determine optimal route and the necessity of formal resuscitation.

Burn injuries of less than 20% are associated with minimal fluid shifts and can generally be resuscitated with oral hydration, except in cases of facial, hand and genital burns, as well as burns in children and the elderly. As the total burned surface area (TBSA) involved in the burn approaches 15-20%, the systemic inflammatory response syndrome is initiated with massive fluid shifts, which result in burn edema and in such cases burn shock is always be expected leading to hyponatremia and hyperkalemia. However, in vivo regimens are unable to quickly restore $K_i^+/K_e^+$ balances and rectify the action potentials of the cardiac, nerve or other cells.

Due to the unavailability of instant in vitro (external) remediation treatments, minimization of blister/edema formation with simultaneous suppression of hyponatremia ($Na^+ \leq 135$ mEq/L) and hyperkalemia ($K^+ \geq 5.5$ mEq/L) to remove $K^+$ ion by in situ transdermal counter diffusion with immediate pain remediation remains unchecked during the first hours of injury as the transcapillary leakage often may continue for 24 hours and further aggravate the situation. However, if proper initial remediation could be introduced at the onset of burn shock to the burn area, the probability of renal and cardiac damage could be significantly lowered in the first hours followed by immediate introduction of appropriate conventional resuscitation regimen (if required).

The route for fluid management and ion management is of principal importance in these instances to safeguard the renal and cardiac functions. Although enteral resuscitation has been attempted for even major burn injuries, vomiting has been a limiting problem for this route. Current recommendations are to initiate formal intravascular fluid resuscitation when the surface area burned is greater than 20%; however, instantaneous or prompt resuscitation can be rarely made available and major damage is caused by hyperkalemia. In other words, for patients with major burns, the formal intravascular route is the preferred choice, except in mass casualty situations where access to medical care is limited, and provided the gastrointestinal tract remains uninjured. In such circumstances, enteral resuscitation with balanced salt solutions can also be initiated.

Formal fluid resuscitation formulas that were introduced in the 1960s and 1970s have been used effectively all over the world. The "Parkland" formula, which calculates the amount of fluid required to resuscitate a patient based on percentage-burn, remains the most commonly used formula in the United Kingdom and Ireland many burn units use it. Similarly, a recent survey of burn units in the United States and Canada revealed that significant number of hospitals or clinics use the Parkland formula to estimate resuscitation volumes.

In centers experienced with pediatric burns, formulas that are sufficient for pediatric fluid management have been developed, as the body surface area to mass ratio in children is higher than in adults and hepatic glycogen stores in young children are depleted after 12-14 hours of fasting. Baxter found out patients with inhalation injury required additional fluid in comparison to others. Pruitt also reported that patients with electrical burns and those in whom resuscitation was delayed routinely also required additional fluid. However, there is growing evidence that other patients with major burns also receive far more fluid than the Parkland formula recommends. The explanation of this experience is unclear, but large volumes of resuscitation fluids are associated with increased risk of infectious complications, acute respiratory distress syndrome (ARDS), abdominal compartment syndrome and death. Pruitt has coined the term "fluid creep" to describe such phenomenon.

Formulas Used for Fluid Management in Major Burns:

The most commonly used formulas are the Parkland, modified Parkland, Brooke, modified Brooke, Evans and Monafo's formulas. These formulas take into account the body weight and the burn surface area. Several formulas that were specifically developed for children by pediatric burn centers have achieved similar acceptance.

Choice of Fluids

The ideal burn resuscitation is the one that effectively restores plasma volume and should restore hyperkalemia and hyponatremia with no adverse effects. Isotonic crystalloids, hypertonic solutions and colloids have been used for this purpose, but every solution has its advantages and disadvantages. None of them is ideal, and none is superior to any of the others.

Hypertonic Solutions

The importance of sodium ions in the pathophysiology of burn shock has been emphasized in some previous studies. The sodium shift into the cell results in cellular edema and hypo-osmolar intravascular fluid volume. Rapid infusion of hypertonic sodium solutions has proven to increase the plasma osmolality and limit cellular edema.

Using solutions with a concentration of 250 mEq/L, effective physiological resuscitation has been achieved with a lower total volume when compared to isotonic solutions in the initial 24 hours. It has been found that after 48 hours cumulative fluid loads of the patient groups who were treated with hypertonic salt solutions or resuscitation liquid (RL) were similar and that hypertonic sodium solution resuscitation was associated with an increased incidence of renal failure and death.

Currently, hypertonic fluid resuscitation seems to be an attractive choice for its theoretically physiological function, but the need for close monitoring and the risk of hypernatremia ($Na^+ \geq 145$ mEq/L) and renal failure are the main focus of debates. However, hypertonic salt solution cannot rectify hyperkalemia or rectify the electrophysiology of the cells.

Colloids

Leakage and accumulation of plasma proteins outside the vascular compartment contributes substantially to edema formation. The time at which the protein leakage stops has been found to differ by various authors. Baxter's early work showed that capillary leak may persist for 24 hours post burn. It has been found that albumin extravasation stops 8 hours after injury, that capillary leakage of protein significantly ceases about 12 hours following the burn, and that endothelial dysfunction and capillary leakage are present within 2 hours after burn injury and last for a median of 5 hours.

Colloids, as hyperosmotic solutions, are used to elevate the intravascular osmolality and to stop the extravasation of the crystalloids. Therefore, controversy focusses on the administration of protein-based colloids: whether to provide them or not, which solutions to use, and when to begin. Some studies have shown that colloids provide little clinical benefit when given in the first 24 hours post burn and may have some detrimental effects on pulmonary function. Therefore, it is critical to develop an in vitro burn treatment solution that would rapidly restore in vivo ion balances by simultaneously rectifying hyperkalemia (overall $K^+ \geq 5.5$ mEq/L) and hyponatremia ($Na^+ \leq 135$ mEq/L) with the application of pH controlled gel mixture formulations on skin surfaces which would also minimize edema formation, balance the pH, pump in sodium ($Na^+$) ion, pump out extracellular potassium ($K^+$) ions which are arriving via transdermal route to the gel mixture formulations from the onset of the burn shock.

This is vitally important because it would expedite highly and locally concentrated potassium ($K^+$) ion removal in situ from blister/extracellular fluid (in vivo), via alternative transdermal route (in vitro) before potassium ($K^+$) ions get the opportunity to get dispersed into the vast network of the circulatory system. The regular route for potassium ($K^+$) ion excretion takes place via kidney; therefore, when potassium ($K^+$) ions suddenly gets sharply elevated during severe burn shock and if it is allowed to get dispersed in extracellular and trans vascular fluids, the high levels of potassium ($K^+$) ion in the fluid could cause renal failure and cardiac arrest leading to patient death. This is the most undesirable situation for any severely burn injured patients.

Fluid Management in Electrical Burns

Patients with electrical burns require additional fluid. In one of the previous study in which an 11-year experience was reported; there, it was found that during two major complications of electrical injuries: musculoskeletal involvement in 44% of patients, which required major amputation in 79%, and acute renal failure (ARF) in 14.51% of patients. In spite of treatment with peritoneal dialysis or hemodialysis, the mortality rate for patients with renal failure turns out to be reasonably very high (59%). In the light of these data, it is clear that the main threat in the initial period is the development of acute tubular necrosis (death of tubular epithelial cells that form the renal tubules of the kidneys) and ARF related to the precipitation of myoglobin and other cellular products.

Myoglobinuria is a common finding in patients with electrical injuries. The phenomenon is exhibited as high-concentrated and pigmented urine. For such burn, one of the primary missions is to maintain a urine output of 1-2 ml/kg/hour until the urine clears. In non-responding patients, alkalization of the urine and the use of osmotic agents may prevent death.

Acute Renal Failure (ARF) and Dialytic Support in Severe Burns

ARF is a severe complication of burns, which occurs in 0.5-30% of burn patients. ARF is related to the size and depth of burns. Microalbuminuria and urinary malondialdehyde are useful markers for prediction of renal outcome in such group of patients. Burn size and septicemia proved to be the only clinical parameters that predict renal outcome.

Two forms of acute renal failure have been described in burn patients: The first form occurs in the initial few hours after injury. Therefore, the present disclosure is a unique solution to minimize patient mortality rate by correcting the potassium ($K^+$) ion imbalances, provided it is applied from the onset of the burn shock. Burn shock leads to hypovolemia resulting in low cardiac output, and systemic vasoconstriction during the resuscitation period.

However, this form of ARF became less frequent due to the aggressive fluid resuscitation policy at the acute stage of the burn management. Significant plasma volume deficits accompany the total fluid loss but are unreplaceable in the early post burn period because capillary permeability is so increased that protein molecules ranging from 60,000 to 340,000 daltons pass as freely as sodium ions from the intravascular to extravascular space. This results in an unbalanced decrease in the circulating plasma volume, which cannot be restored by plasma expanders (colloid solutions) until capillary permeability is restored.

By 24 hours, post burn capillary permeability is restored and recovered sufficiently to permit rapid restoration of the plasma volume. However, in case of severe burn injury, an hour of delay in administering resuscitating fluid might be too little too late when local excess potassium ($K^+$) ions already begins to disperse throughout the vast network of the circulatory system. This is best done with fresh or shelf-stored plasma, requiring 0.5 ml per % burn per kg, administered in the interval between 24 and 36 hours.

In very massive burns, the restoration of capillary integrity may be somewhat slower, and additional volumes of plasma may be necessary between 32 to 40 hours following injury. Plasma substitutes are not recommended since they may further impair immunologic incompetence. Water requirements for the first 24 hours are adequately met by the "free" $H_2O$ of lactated Ringers solution. Since the $Na^+$ concentration is ~130 mEq/L, 80 cc of "free" $H_2O$ is given with each liter.

The detailed understanding of pathophysiology of burn treatment is helpful to formulate a gel mixture formulation matrix for its external application (in vitro) over the skin surfaces as a prompt and first response, beginning from the onset of mild or severe burn shock to minimize the most of the complications arising from burn injuries. In the present disclosure, gel mixture formulations are applied over the unopened burn injured areas at the onset of burn shock injury to transport ions across the transmembrane route to rectify the pH and ion imbalances in extracellular fluid, thereby, restoring the homeostasis condition in blister/extracellular fluid.

Severe burn injury results in hyponatremia ($Na^+ \leq 135$ mEq/L), initial acidosis (pH$\leq$7.35); as well as cell lysis, tissue necrosis which results in severe hyperkalemia (local $K^+ \geq 70$), followed by subsequent alkalosis (pH$\geq$7.45) with agonizing pain along with translocation of vascular fluid to extracellular or interstitial space resulting in the disruption of regular homeostasis as shown in FIGS. 3, 4 and 5; subsequently causing severe malfunctions in multiple organs. Hyponatremia ($Na^+ \leq 135$ mEq/L) in extracellular fluid is caused by translocation of vascular serum/fluid via transcapillary fluid loss into interstitial spaces, thus, diluting the $Na^+$ ion concentration in extracellular fluid that commence at the beginning of burn shock as local events. During this event, both extracellular fluids and sodium ($Na^+$) move into intercellular spaces causing cellular edema too. As a result of hyponatremia ($Na^+ \leq 135$ mEq/L), the sodium ($Na^+$) ions move less rapidly from the extracellular/plasma fluid through the gated ion channels into the cells and cannot keep up with their usual transport rates (flatter slope), thus, $Na^+$ ions face uphill battle in raising the action potentials in varieties of cells during depolarization stages at the normal rate.

In addition, the pH in extracellular/blister fluids also drops below 7.35 resulting in initial acidosis which causes hydrogen ($H^+$) ion concentration to increase (due to rapid dissociation of lactic acid from metabolic acidosis) in extracellular/plasma fluids which consequently leads to hydrogen ($H^+$) ions to move inside the unharmed cells thus ejecting substantially additional amount of potassium ($K^+$) ions into the extracellular fluids. In parallel, during such injuries, excessively high levels of local hyperkalemia initially occur, e.g., due to cell lysis, tissue necrosis and adrenocortical response, initial respiratory and skeletal metabolic acidosis which results in raising the local release of highly concentrated intercellular $K^+$ ions into the local extracellular, blister and vascular fluid as shown in FIGS. 3, 4 and 5.

Subsequently, as the locally released and highly concentrated potassium ($K^+$) ions prefers to rapidly pervade into the intravascular and greater part of the extracellular fluid, while this dispersion is transported into the highly interconnected vast network of the circulatory system, resulting in hyperkalemia ($K^+ \geq 5.5$ mEq/L) across the vascular system. This is also shown in FIGS. 3, 4 and 5. The dispersion of potassium ($K^+$) ions throughout the vast network of the circulatory system could take place via several mechanisms, viz., diffusion, capillary flow and momentum transfer etc. Therefore, the first few minutes to few hours from the onset of burn shock is critically vital to simultaneously contain and mitigate initial acidosis, hyponatremia, hyperkalemia and subsequent alkalosis. If not rapidly checked, eventually during severe burn injury, this leads to overall increase in the equilibrium extracellular and intravascular concentration of potassium ($K^+$) ions, beyond 5.5 mEq/L, following the transportation of ions and their dispersion, causing destabilization of homeostasis in human body. This condition is depicted in FIGS. 3 and 5.

Higher concentration of potassium ($K^+$) ion present in extracellular fluid in turn raises the membrane potential above the threshold potential. Thus, several gated sodium ($Na^+$) ion channels remains unopened as they all only get activated when the membrane potentials increase from standard resting membrane potential to certain threshold potential (except pace maker cells; they don't have any resting membrane potential), thus only decreased number of $Na^+$ ions get the opportunity to cross through the ion channels across the cell membranes due to the reduced number of $Na^+$ ion channels could open up.

Figure 6:
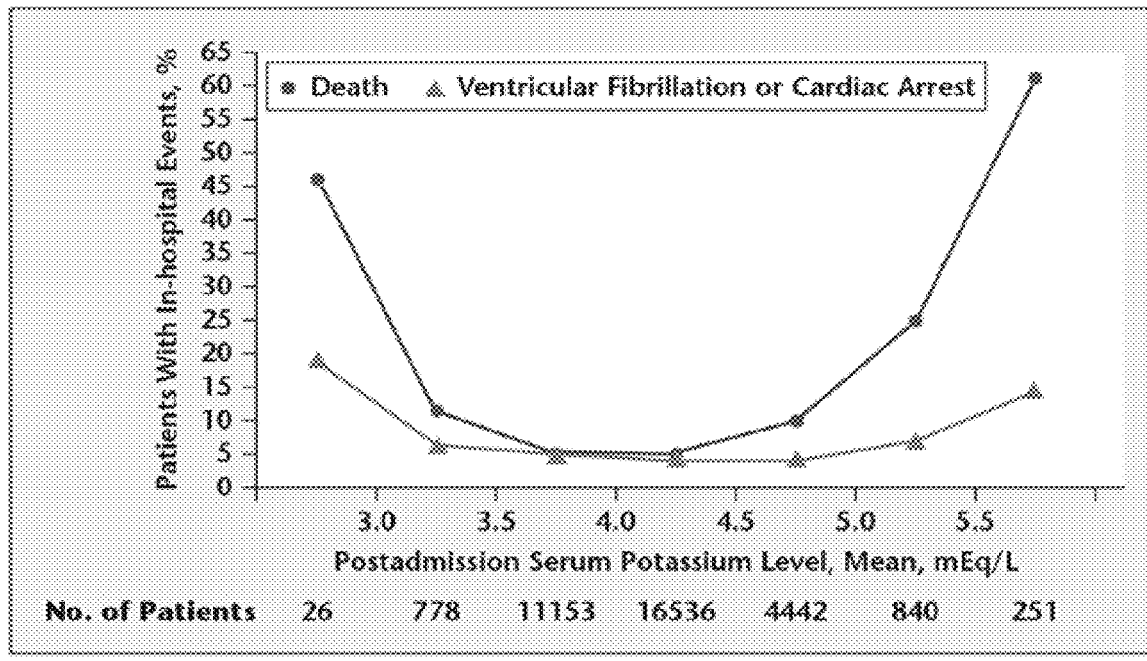
FIG. 6: A graph showing post admission percent death and ventricular fibrillation or cardiac arrest versus serum potassium ($K^+$) ion.

Higher concentration of potassium ($K^+$) ions in extracellular or plasma fluid leads to abnormally raising the resting membrane potentials than their usual higher levels, thus deactivating some of the ($Na^+$) ion channels of the cell membranes. On top of that the presence of lower concentration (level) of $Na^+$ in extracellular fluid also reduces the rate of $Na^+$ ion intrusion inside the cells thus reducing the slope of the action potentials in nerve, skeletal muscle and other cells. This anomaly is also observed in myocytes and results in severe deviations in the action potentials during both the depolarization and repolarization stages of the cardiac cells, thus, the optimal electrophysiology of these cells gets disrupted; as a result, may eventually lead to fatalities, once the potassium ($K^+$) ion concentration levels overshoots 5.5 mEq/L and above. This is shown in FIGS. 6, 7 and 12.

The detrimental impact of hyperkalemia clearly becomes evident in the electrocardiogram (ECG) in myocytes (cardiac cells) when potassium ($K^+$) ion concentration in extracellular fluid and serum exceeds 6.5 mEq/L and above, as shown in FIG. 12. Consequently, the abnormally low and high concentrations of $Na^+$ and $K^+$ ions leads to destabilization and disruptions of regular homeostasis, which consequently leads to other organ dysfunctions from the beginning of the severe burn shock.

Since kidney is the organ that is responsible for the excretion of excess or most of the $K^+$ ions from the human body to reestablish the normal homeostasis, the excess $K^+$ ion must traverse a very long path along the vast and interconnected network of the circulatory system before the ions are excreted through the kidney. It should be noted that it takes four (4) hours to excrete $K^+$ ion, probably due to the reason $K^+$ ions need to traverse a longer path along the vast and interconnected network of the circulatory system to reach the renal system, since the length of the circulatory system (See FIG. 11) stretches as long as ~60,000-100,000 miles in normal human body. Therefore, after severe burn injuries, excess concentration of local potassium ($K^+$) ions after their dispersion raises the overall average potassium ($K^+$) ion concentration although by only few mEq/L; however, only few mEq/L rise in potassium ($K^+$) ion concentration is very sensitive to maintaining the electrophysiology of the vital organs (kidney and cardiac) of the burn patients; and with large volume of translocated extracellular and intravascular fluid puts a severe constraints on the renal functions, if these locally accumulated fluid and heavily concentrated potassium ($K^+$) ions are not both rapidly managed and locally (in situ) purged respectively from the burn shock regions and their vicinities, preferably through the alternate transdermal route, while bypassing renal excretion. Else, excessively higher concentration of potassium ($K^+$) ion in serum and extracellular fluid even after their dispersion and with higher volume would create severe load on kidney and in some cases result in renal failure unless potassium ($K^+$) ions are purged rapidly at the onset of burn shock.

However, before the high concentration of local potassium ($K^+$) ions get dispersed into the serum and extracellular fluid, if these highly concentrated local potassium ($K^+$) and hydrogen ($H^+$) ions resulting from the released lactic acid dissociation due to metabolic acidosis could be ousted across the local transdermal routes and push them to get entrapped outside (in vitro) into the gel mixture formulation, it would not only reduce the excretion/purge time, however, also reduce its deleterious impact on kidney as well as the cardiac functions. The expulsion or ouster of such locally concentrated potassium ($K^+$) ions are more favorable as long as higher concentration gradient could be maintained across the transdermal route.

Figure 8:
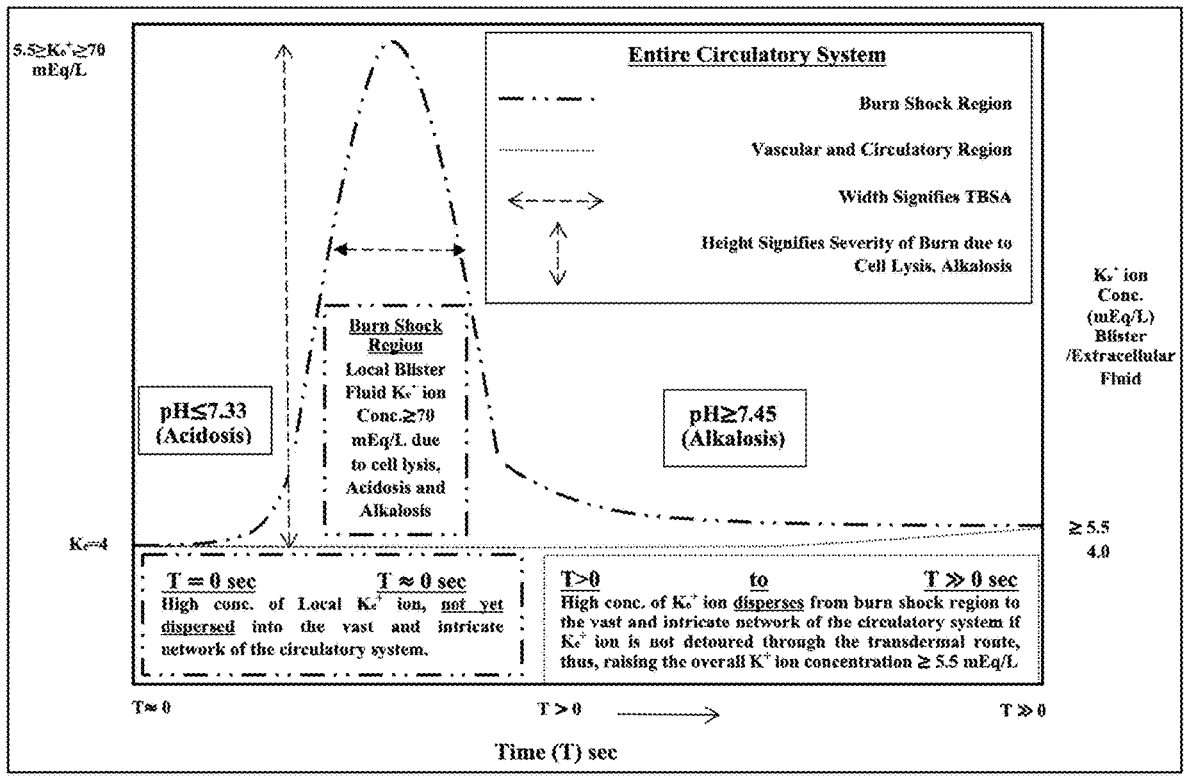
FIG. 8: A figure showing the local surge in potassium ($K_e^+$) ion concentration that eventually disperses across the vast network of the circulatory system over time, thus raising the overall extracellular potassium ($K_e^+$) ion concentration in excess of 5.5 mEq/L once dispersed.

However, after severe burn injury, even if very high local concentration of potassium ($K^+$) ions in blister fluid would level out or get diluted over time due to dispersion, overall, it may still overshoot 5.5 mEq/L levels in the extracellular or vascular fluid in case of severe burn injury, unless this excess potassium ($K^+$) ions are not quickly ejected by other means from the very beginning of the burn shock, as shown in FIGS. 8 and 9.

Therefore, it would be highly practical, beneficial, and in many cases a lifesaving endeavor, to create an environment, in vitro, inside a gel mixture/substrate/matrix formulation spread over the burn injured skin surfaces, if the gel mixture formulations could be effortlessly applied all over the burn affected areas on the outside skin surface and its vicinities to impose a steep concentration gradient to help diffuse in sodium ($Na^+$) and pH control ions through the transdermal route, to balance the initial hyponatremia ($Na^+ \leq 135$ mEq/L) and initial acidosis right from the onset of burn shock on one hand; and on the other hand, during the same process, simultaneous and counter diffusional in situ expulsion of excess potassium ($K^+$) ions are also expeditiously facilitated from the blister/edema/extracellular fluid via the same route in the opposite direction before potassium ($K^+$) ions get the opportunity to disperse themselves along the vast and complex network of the circulatory system, provided the gel mixture formulation is very swiftly and immediately applied on the injured burn surfaces and its vicinities right from the onset of the burn shock. Therefore, to maintain higher potassium ($K^+$) ions expulsion rate, the applied gel mixture formulation may be replaced with fresh ones to maintain the concentration gradients in every few minutes at the onset of burn injury especially when the patients suffer from more than 10-20% total burn surface area (TBSA) injury.

Thus, in situ pumping of sodium ($Na^+$) ion as well pH control agents from the gel formulation matrix (in vitro) through the transdermal route also helps retard and diminish the blister fluid accumulation by reversing the transcapillary fluid loss if the gel mixture formulation is applied right from the very beginning of the burn shock. Here, it should be noted that pumping equal amounts of sodium ($Na^+$) and chloride ($Cl^-$) ions via the transdermal route, i.e., it may potentially raise the local concentration of chloride ($Cl^-$) ions and may eventually create a net surplus if the applied gel mixture formulation is maintained continuously for several hours and thus may create a negative impact in the serum/plasma to some degree.

During the regular homeostasis conditions, the counter chloride ($Cl^-$) ion in the extracellular fluid may not be allowed to exceed ~112 mEq/L with respect to sodium ($Na^+$) ion concentration (140 mEq/L) because the excess sodium ($Na^+$) ~38 mEq/L balances other anions in the extracellular fluid/plasma. Excess chloride ($Cl^-$) ion pumping would thus cause hyperchloremic condition in plasma/extracellular fluids and result in hyperchloremic acidosis.

There are several definitions concerning varieties of acidosis, and one method of classification is on the basis of related ionic imbalances that needs to be discussed in this context, viz., the anion gap (AG), which is defined as the molar concentration of sodium ([Na]) in blood plasma minus those of chloride ([$Cl^-$]) and bicarbonate ([$HCO_3^-$]):

$$AG = [Na^+] - ([Cl^-] + [HCO_3^-]) \quad \text{EQN 3}$$

Here, it should be mentioned that chloride ($Cl^-$) ion is not a "metabolic" product. Therefore, any hyperchloremia related chloride ($Cl^-$) surge in the plasma/extracellular fluid is in reality are not related to "metabolic" acidosis, yet they may contribute to acidosis. However, the release of lactic acid ($CH_3CHCOOH$) and their dissociation to hydrogen ($H^+$) ions from skeletal muscle cells due to any kind of shock causes initial metabolic acidosis and thus contribute to the drop in pH in the extracellular fluid. Here, it is critical to note that lactic acidosis, however not hyperlactatemia, closely correlates with the mortality risk and serves as a window into cell level oxygen-dependent processes.

There is another definition that relates to ion balance or imbalance is given by strong ion difference (SID) which is given by the following:

$$SID = ([Na^+] + [K^+] + [Mg^{2+}] + [Ca^{2+}]) - ([Cl^-] + [(CH_3CHCOO^-)]) = [\text{Dissociated Strong Cations}] - [\text{Dissociated Strong Anions}] \quad \text{EQN 4}$$

Figure 13:
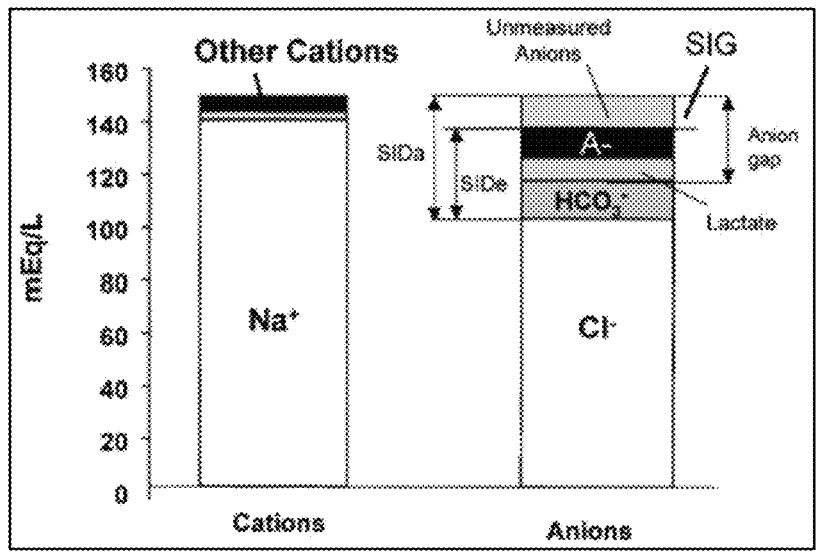
FIG. 13: A graph illustrating sodium ($Na^+$) ions in extracellular fluid or plasma balanced by chloride ($Cl^-$) ions and other anions, viz., bicarbonate ($HCO_3^-$), lactate, charged proteins (amino acid anions) etc. Here, chloride ($Cl^-$) ion increase leads to hyperchloremia leading to undesirable acidosis.

It should be noted that the relatively lower concentration of dissociated bicarbonate ($HCO_3^-$) ions are present in blood serum/extracellular fluids; therefore, strong ions, i.e., only dissociated ions shows up as significant in the above SID equation (EQN 4). Here it should be noted that SID must be counterbalanced by equal and opposing charges, termed as the effective strong ion difference ($SID_e$) as shown in FIG. 13. This measurable difference is referred to as the 'apparent' SID ($SID_a$), with the understanding that not all ions may be accounted for. In healthy humans this number is close to +40 mEq/L. The law of electro-neutrality states that there must be an equal and opposing charge to balance the positive charge, and so the +40 mEq/L is balanced by an equal negative force comprised mostly of weak acids ($A_{TOT}$). These weak acids include plasma proteins (predominately albumin) and phosphates.

Therefore, in case of excess chloride ($Cl^-$) ions accumulating in plasma would result in a narrowed strong ion difference (SID) and therefore, resulting in a reduced plasma positive net strong ion charge. When relative plasma positive charge is reduced, as commonly occurs with significant chloride ($Cl^-$) ion loading (reduced SID); as a result, an immediate and compensatory response is the proton or hydrogen ($H^+$) ion generation to assist in restoring the charge equilibrium. The clinicians identify this physiologic disordered process as decreased pH or hyperchloremic acidosis. With hyperchloremic acidosis, it would create a spuriously more negative base deficit (or increased base excess, e.g., lactate ($CH_3CHCOO^-$), i.e., excess anion from lactic acid dissociation) as the $Cl^-$ decreases the pH unaccompanied by hypoperfusion and lactic acidemia. Such hyperchloremic condition would initiate acidosis in extracellular fluid with lactic acid dissociation, which is also highly undesirable because of excess hydrogen ($H^+$) ions production (releasing excess $K^+$ ion from intracellular compartments) during homeostasis while the body manages SID in extracellular/plasma fluid.

To circumvent this anomaly, the addition of sodium bicarbonate ($NaHCO_3$) and other biocompatible sodium (Na) salts of organics acid(s) ions (e.g., lactate, acetate, citrate etc.) in the gel mixture formulations also help transport bicarbonate ($HCO_3^-$) ions and/or biocompatible organic acid anion(s) and/or their counterpart ($Na^+$) ions as well as generated hydroxyl ($OH^-$) ions from the anions gets transported via diffusion process across the same transdermal route as a pH control component to mitigate initial respiratory/metabolic acidosis in the blister/extracellular/plasma/serum fluids. Two examples for sodium salts of weak acids (sodium bicarbonate and sodium acetates respectively) are shown in the following equations:

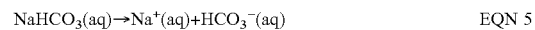

$$NaHCO_3(aq) \rightarrow Na^+(aq) + HCO_3^-(aq) \quad \text{EQN 5}$$

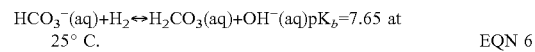

$$HCO_3^-(aq) + H_2 \leftrightarrow H_2CO_3(aq) + OH^-(aq) \, pK_b = 7.65 \text{ at } 25° C. \quad \text{EQN 6}$$

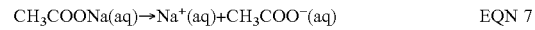

$$CH_3COONa(aq) \rightarrow Na^+(aq) + CH_3COO^-(aq) \quad \text{EQN 7}$$

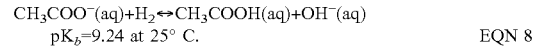

$$CH_3COO^-(aq) + H_2 \leftrightarrow CH_3COOH(aq) + OH^-(aq) \, pK_b = 9.24 \text{ at } 25° C. \quad \text{EQN 8}$$

The addition of these sodium salts of various weak acids in aqueous system and their different concentration result in producing different alkaline or acidic pH at 25° C. as shown in Tables 1 and 2. Incidentally, these equilibrium reactions follow Le Chatelier's principle. Therefore, the combined pH of a mixture of more than one sodium salt mixtures of weak acids results into equilibrium conditions (T, pH etc.) that govern the overall pH change and the final equilibrium pH in the Formulations (I and II) to create steeper pH gradient across transdermal membrane to minimize initial acidosis and prevent $K^+$ ion release from the intracellular compartments into the extracellular fluid to counter subsequent alkalosis.

It should be noted that the presence of strong and weak electrolytes in the gel mixture Formulations (I and II) would give rise to non-ideal conditions which may result in deviations from pH presented in Tables 1 and 2 without varying activity coefficients in the Formulation (I) and Formulation (II).

TABLE 1

Approximate pH Values versus Various Sodium Salt of Weak Acid Concentration.

| Mol. Wt. | Salt of Weak Acids | Eq/L | pKa | pH (approx.) | mg/L |
|---|---|---|---|---|---|
| 84.0 | Sodium Bicarbonate | 5.00E−01 | 6.35 | 10.02 | 42000.00 |
| 84.0 | (NaHCO3) | 4.50E−03 | 6.35 | 9.00 | 378.00 |
| 84.0 | | 1.40E−03 | 6.35 | 8.75 | 117.60 |
| 84.0 | | 2.00E−04 | 6.35 | 8.32 | 16.80 |
| 84.0 | | 4.50E−05 | 6.35 | 7.99 | 3.78 |
| 84.0 | | 3.00E−05 | 6.35 | 7.90 | 2.52 |
| 84.0 | | 2.00E−05 | 6.35 | 7.81 | 1.68 |
| 84.0 | | 1.00E−05 | 6.35 | 7.65 | 0.84 |
| 82.0 | Sodium Acetate | 1.00E+00 | 4.76 | 9.38 | 82000.00 |
| 82.0 | (CH3COONa) | 1.00E−01 | 4.76 | 8.88 | 8202.36 |
| 82.0 | | 1.00E−02 | 4.76 | 8.38 | 820.24 |
| 82.0 | | 2.00E−03 | 4.76 | 8.03 | 164.05 |
| 82.0 | | 3.00E−04 | 4.76 | 7.62 | 24.61 |
| 82.0 | | 2.00E−04 | 4.76 | 7.53 | 16.40 |
| 82.0 | | 4.00E−05 | 4.76 | 7.18 | 3.28 |
| 112.0 | Sodium Lactate | 1.40E+00 | 3.86 | 9.00 | 156800.00 |
| 112.0 | (C3H5O3Na) | 1.00E−01 | 3.86 | 8.43 | 11200.00 |
| 112.0 | | 1.50E−02 | 3.86 | 8.02 | 1680.00 |
| 112.0 | | 6.00E−03 | 3.86 | 7.82 | 672.00 |
| 112.0 | | 3.50E−03 | 3.86 | 7.70 | 392.00 |
| 112.0 | | 1.50E−03 | 3.86 | 7.52 | 168.00 |
| 112.0 | | 2.00E−03 | 3.86 | 7.58 | 224.00 |
| 112.0 | | 2.50E−03 | 3.86 | 7.63 | 280.00 |
| 258.1 | Trisodium Citrate | 1.64E+00 | 3.14 | 8.68 | 423218.40 |
| 258.1 | (C6H5O7Na3) | 1.00E+00 | 3.14 | 8.57 | 258060.00 |
| 258.1 | | 1.65E−01 | 3.14 | 8.18 | 42579.90 |
| 258.1 | | 1.00E−01 | 3.14 | 8.07 | 25810.00 |
| 258.1 | | 5.00E−02 | 3.14 | 7.92 | 12905.00 |
| 258.1 | | 1.00E−03 | 3.14 | 7.07 | 258.06 |
| 258.1 | | 5.00E−04 | 3.14 | 6.92 | 129.03 |
| 258.1 | | 3.00E−04 | 3.14 | 6.81 | 77.42 |
| 258.1 | | 2.00E−04 | 3.14 | 6.72 | 51.62 |

Note:
Atmospheric $CO_2$ dissolves into gel mixture formulation and may significantly reduce the overall pH of the mixture over time ((Without the use of Activity Coefficients)

TABLE 2

Examples of Concentrated Sodium Bicarbonate and Sodium Carbonate Buffers at Different Ratios to Create a Wider pH Range (~9-10) in Ideal Solution Scenario (Without the use of Activity Coefficients)

| MolFrac NaHCO3 | MolFrac Na2CO3 | Ka1 | Ka2 | Eq/L NaHCO3 | Eq/L Na2CO3 | mg/L NaHCO3 | mg/L Na2CO3 | pH |
|---|---|---|---|---|---|---|---|---|
| 0.66604 | 0.33381 | 4.47E−07 | 5.01E−11 | 3.33E−01 | 1.67E−01 | 27973.68 | 17691.97 | 10 |
| 0.71511 | 0.28469 | 4.47E−07 | 5.01E−11 | 3.58E−01 | 1.42E−01 | 30034.56 | 15088.56 | 9.9 |
| 0.75954 | 0.24019 | 4.47E−07 | 5.01E−11 | 3.80E−01 | 1.20E−01 | 31900.77 | 12729.98 | 9.8 |
| 0.79895 | 0.20069 | 4.47E−07 | 5.01E−11 | 3.99E−01 | 1.00E−01 | 33556.10 | 10636.48 | 9.7 |
| 0.83327 | 0.16626 | 4.47E−07 | 5.01E−11 | 4.17E−01 | 8.31E−02 | 34997.42 | 8811.76 | 9.6 |
| 0.86267 | 0.13672 | 4.47E−07 | 5.01E−11 | 4.31E−01 | 6.84E−02 | 36231.97 | 7246.34 | 9.5 |
| 0.88748 | 0.11173 | 4.47E−07 | 5.01E−11 | 4.44E−01 | 5.59E−02 | 37274.23 | 5921.55 | 9.4 |
| 0.90816 | 0.09082 | 4.47E−07 | 5.01E−11 | 4.54E−01 | 4.54E−02 | 38142.91 | 4813.27 | 9.3 |
| 0.92520 | 0.07349 | 4.47E−07 | 5.01E−11 | 4.63E−01 | 3.67E−02 | 38858.47 | 3895.04 | 9.2 |

Therefore, salt(s) of weak acid, e.g., sodium bicarbonate ($NaHCO_3$) or combined mixture of other biocompatible sodium salt of weak acids mixtures, viz., sodium lactate, sodium acetate, trisodium citrate must be added singly or in various combinations in the gel mixture formulation to minimize/rectify acidosis (respiratory, metabolic and hyperchloremic) in blister/extracellular/plasma fluids during burn shock treatments and prevent negative effect of hyperchloremic acidosis, prevent reduction in SID while the corresponding anions also move inside across transdermal route.

It should also be noted that the addition of sodium lactate and other salts (e.g., sodium acetate) of weak acids including sodium bicarbonate added in the gel mixture formulation helps their intrusion via diffusion across transdermal route to mitigate SID narrowing and neutralizing the excess hydrogen ($H^+$) ions (in vitro) as a result of the dissociation of lactic acid release (from skeletal cells via initial metabolic acidosis) by newly formed hydroxyl ($OH^-$) ions as the salt of weak acid(s) dissociate (in vitro) and neutralize the hydrogen ($H^+$) ions arriving (in vitro) by counter-diffusion through transdermal route, while protecting the overall SID contraction in the extracellular fluids while the lactate ions from sodium lactate dissociation prevents the released lactic acid from dissociation due to Le Chatelier's principle.

It is important to recognize that the changes in plasma electrolyte concentration are mEq/L in scale, while the corresponding changes in proton concentrations are at nano Eq/L scale, i.e., pH ($7.35 \leq pH \leq 7.45$) scale and therefore, not a large concentration of sodium salts of weak acids would be required to correct the pH of the extracellular/blister/plasma fluid.

In addition, strong cationic liquid polyelectrolytes comprised of primarily sodium ($Na^+$) ions, viz., sodium polystyrene sulfonate (Na-PSS; Kayexalate) and/or sodium polyacrylate may also be added as ingredients to prepare the gel mixture Formulations (I and II) as such that they are part of supplementary ingredients in the gel mixture formulations, both for regular (I) and follow up Formulation (II). Formulation (II) may be applied if at least three fourth (¾) of an hour has passed after the occurrence of burn shock with prior application of Formulation (I) or with at least after the eighth replacement of fresh gel mixture Formulation (I) has already been recurrently applied and replaced (every 2-3 minutes), to prevent proliferation of hyperchloremia in the blister/extracellular/plasma fluid since Formulation (II) has lower concentration of sodium chloride present in the Formulation (II).

Figure 14:
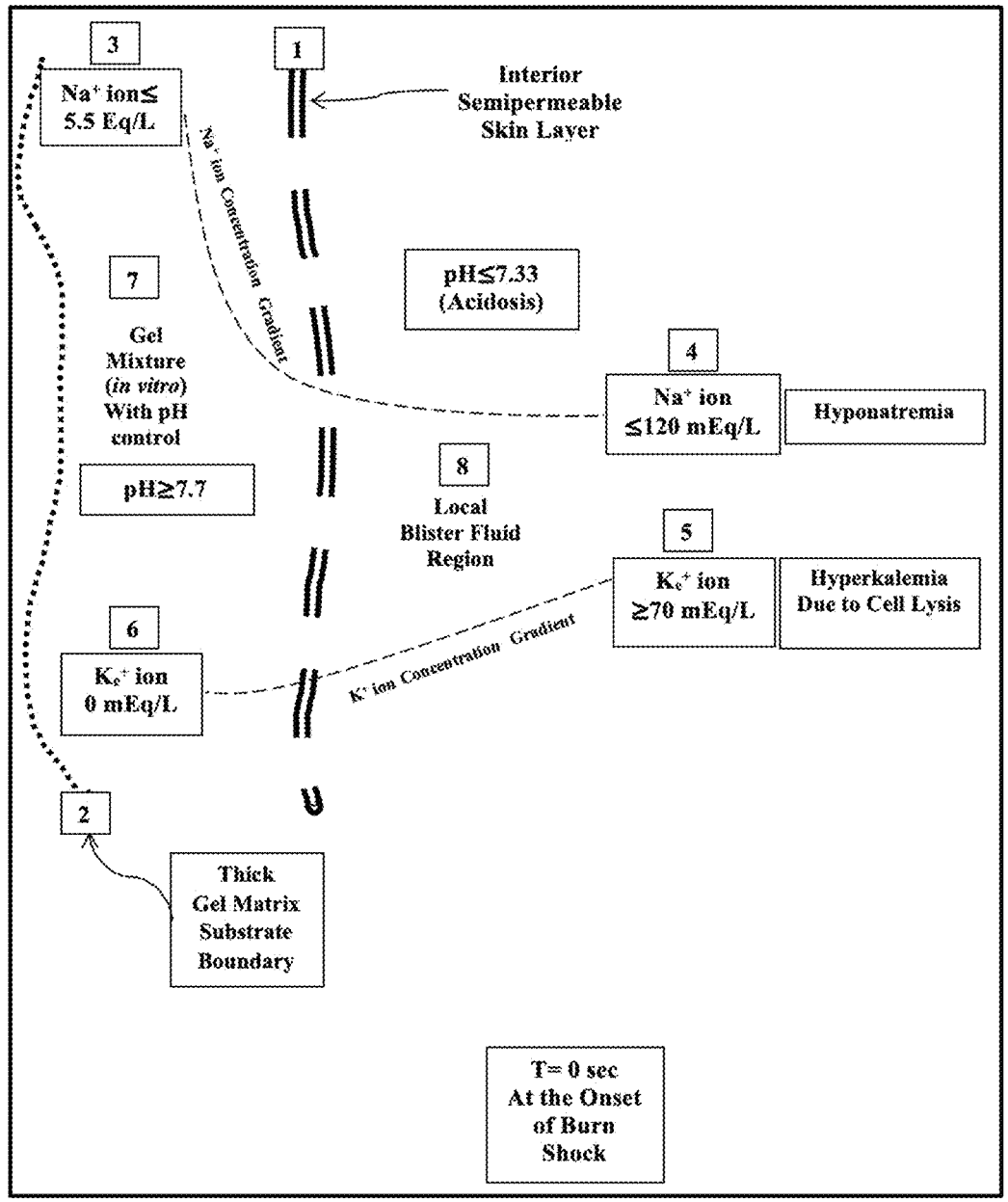
FIG. 14: A diagram of counter diffusional mass transfer of sodium ($Na^+$) and local extracellular/blister potassium ($K_e^+$) ions across the transdermal barrier with initial acidosis at the onset of burn shock ($T \approx 0$).
Figure 15:
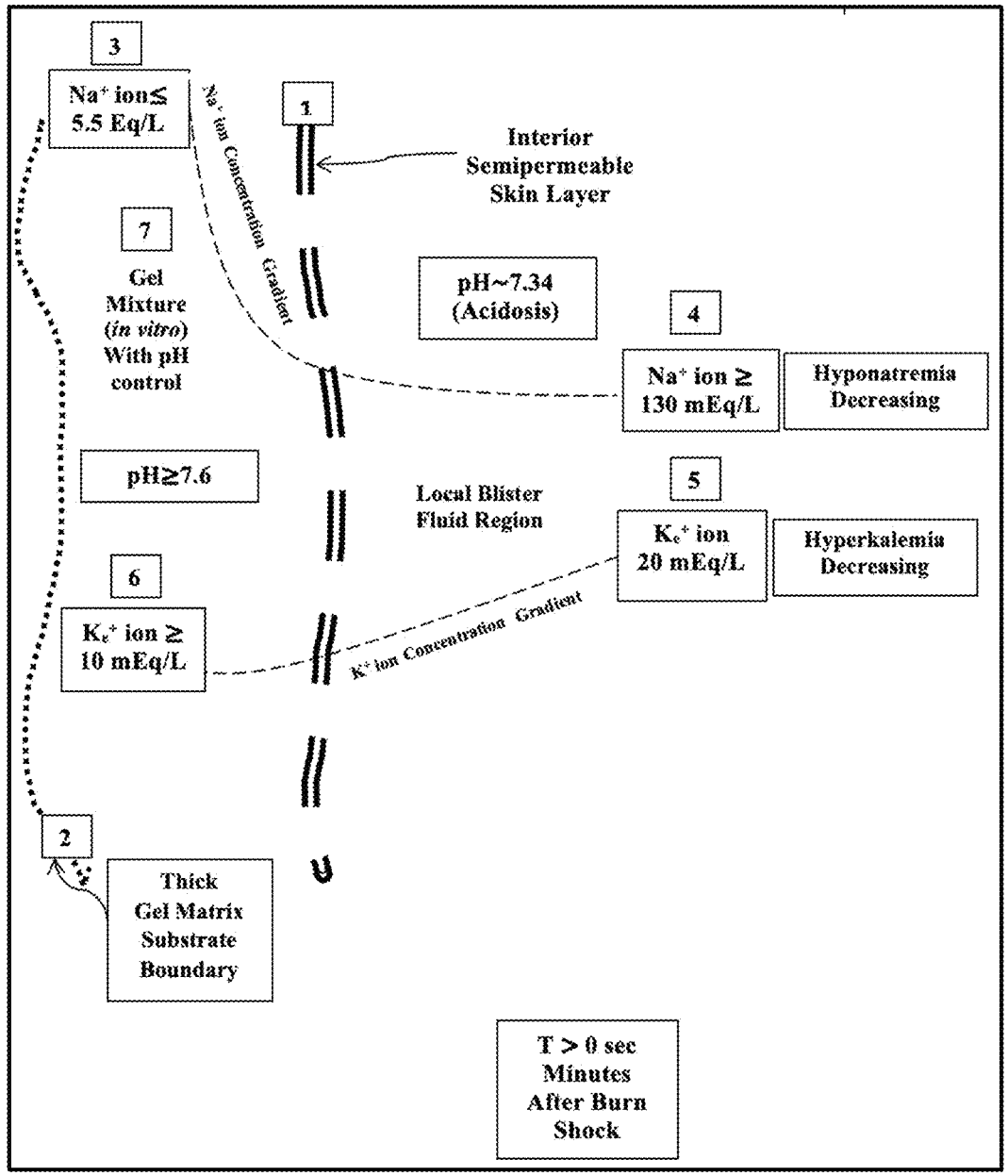
FIG. 15: A diagram of counter diffusional mass transfer of sodium ($Na^+$) and local extracellular/blister potassium ($K_e^+$) ions across the transdermal barrier with initial acidosis at ($T>0$) and subsequent pH balance.
Figure 16:
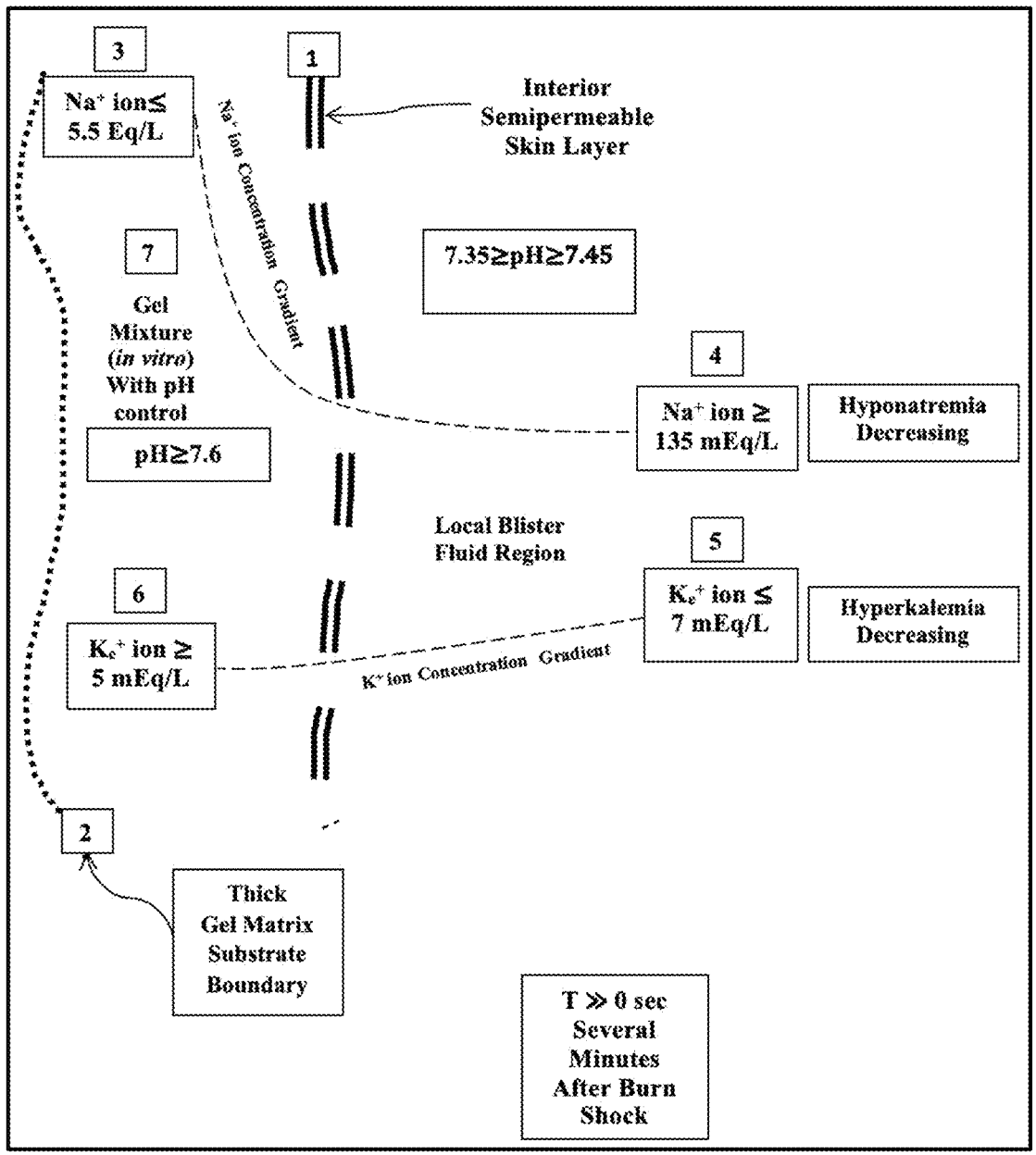
FIG. 16: A diagram of sodium ($Na^+$) and local extracellular/blister potassium ($K_e^+$) ion concentration across the transdermal barrier with initial acidosis (at $T>>0$).
Figure 17:
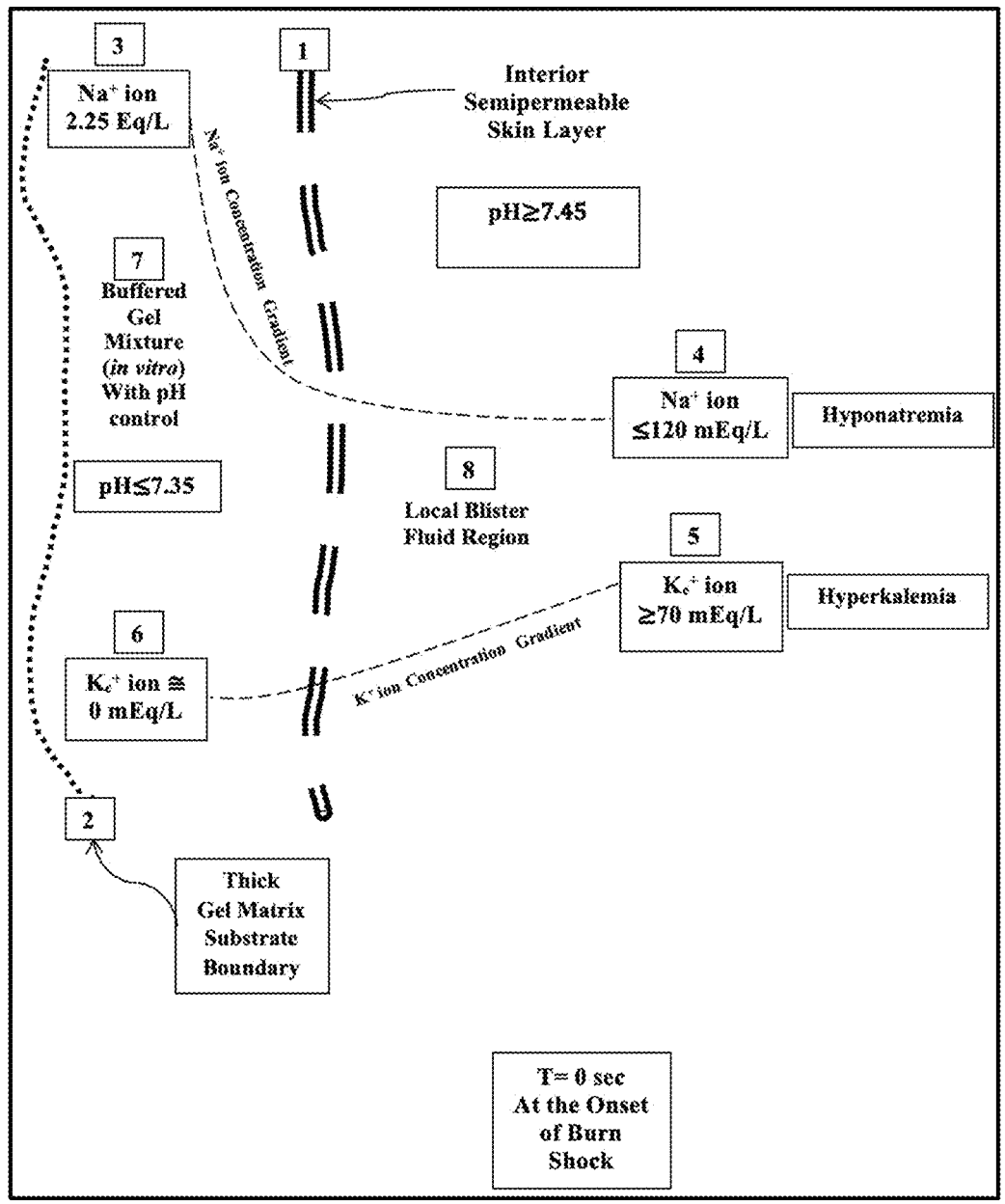
FIG. 17: A diagram of counter diffusional mass transfer of sodium ($Na^+$) and local extracellular/blister potassium ($K_e^+$) ions across the transdermal barrier with subsequent alkalosis at the onset of burn shock ($T \approx 0$).
Figure 18:
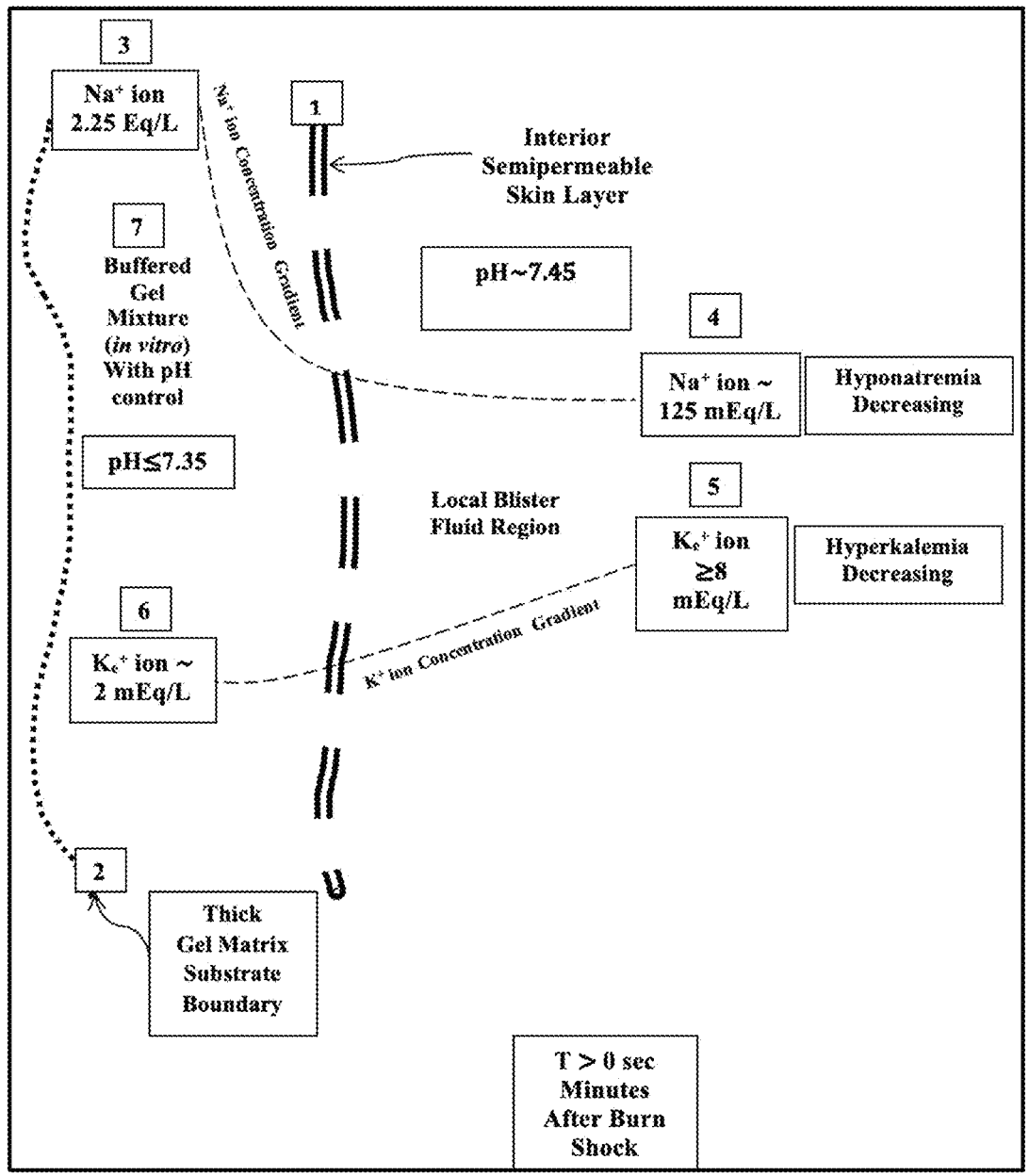
FIG. 18: A diagram of counter diffusional mass transfer of sodium ($Na^+$) and local extracellular/blister potassium ($K_e^+$) ions across the transdermal barrier with subsequent alkalosis (at $T>0$) and subsequent pH rectification.
Figure 19:
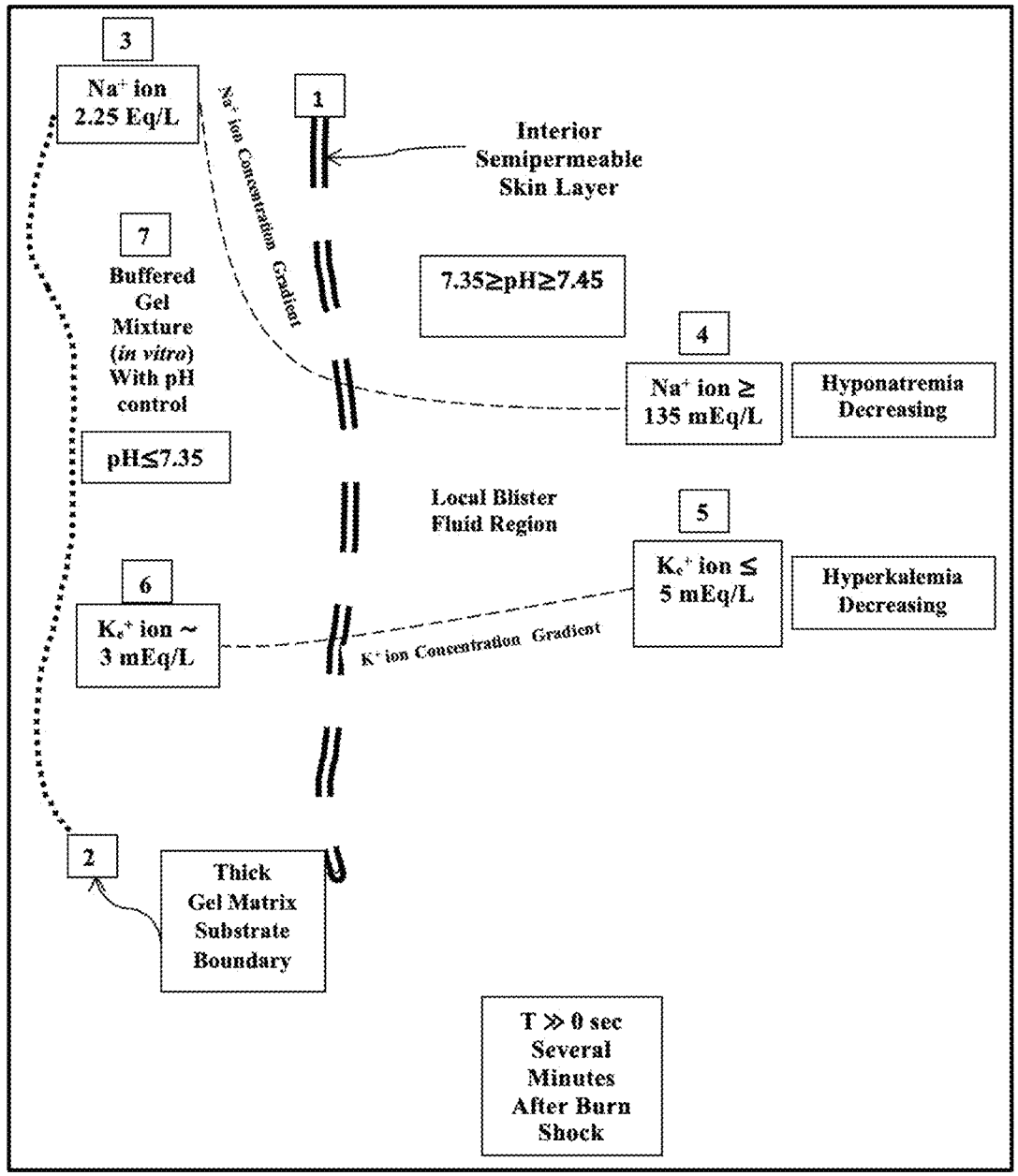
FIG. 19: A diagram of severely burn injured patient's intracellular cell ion concentration with subsequent alkalosis (time, $T>>0$) versus local surge in extracellular fluids/plasma ($K^+$) ion concentrations.

Again, it should be noted that the usual intracellular potassium ($K^+$) ion concentration is ~140 mEq/L (See FIG. 1), therefore, during severe burn injury, the discharge of potassium ($K^+$) ions to the extracellular fluid due to cell lysis, tissue necrosis, initial respiratory and metabolic acidosis ($H^+$ ion release due to lactic acid dissociation) and respiratory acidosis raises the local extracellular/blister potassium ($K^+$) ion concentrations to very high levels from the very beginning of the burn shock injury, depending on the severity and depth of burn injury. This is depicted in FIGS. 14 and 17.

Therefore, swift removal of potassium ($K^+$) and hydrogen ($H^+$) ions are very critical and could be only achieved early, if the application of this gel mixture is spread over the burn areas and their vicinities at the onset of burn shock to swiftly initiate potassium ($K^+$) and hydrogen ($H^+$) ion transfer in situ via transdermal route via counter-diffusion (in vitro) since only at that point the concentration gradient of potassium ($K^+$) ion is maximum across the transdermal route. This too are depicted in FIGS. 8, 9, 14-19.

Similarly, the presence of sodium salt of weak organic acids existing as other active ingredients in the Formulation (I) presented the present disclosure would also swiftly retard the continuous decrease in pH levels (pH≤7.35) in the extracellular/blister fluids once the anions of weak organic acids and hydroxyl ($OH^-$) ions moves through the transdermal route (via diffusion) into the extracellular/blister fluid region (in vivo) or excess hydrogen ($H^+$) ions present in blister/extracellular fluid begins to move out (in vitro) via counter-diffusion into the gel mixture Formulation (I) and swiftly minimize initial acidosis in parallel. This in turn, would reduce potassium ($K^+$) ion release from healthy cells into extracellular/blister fluids from the initial stages of burn shock injury.

Figure 20:
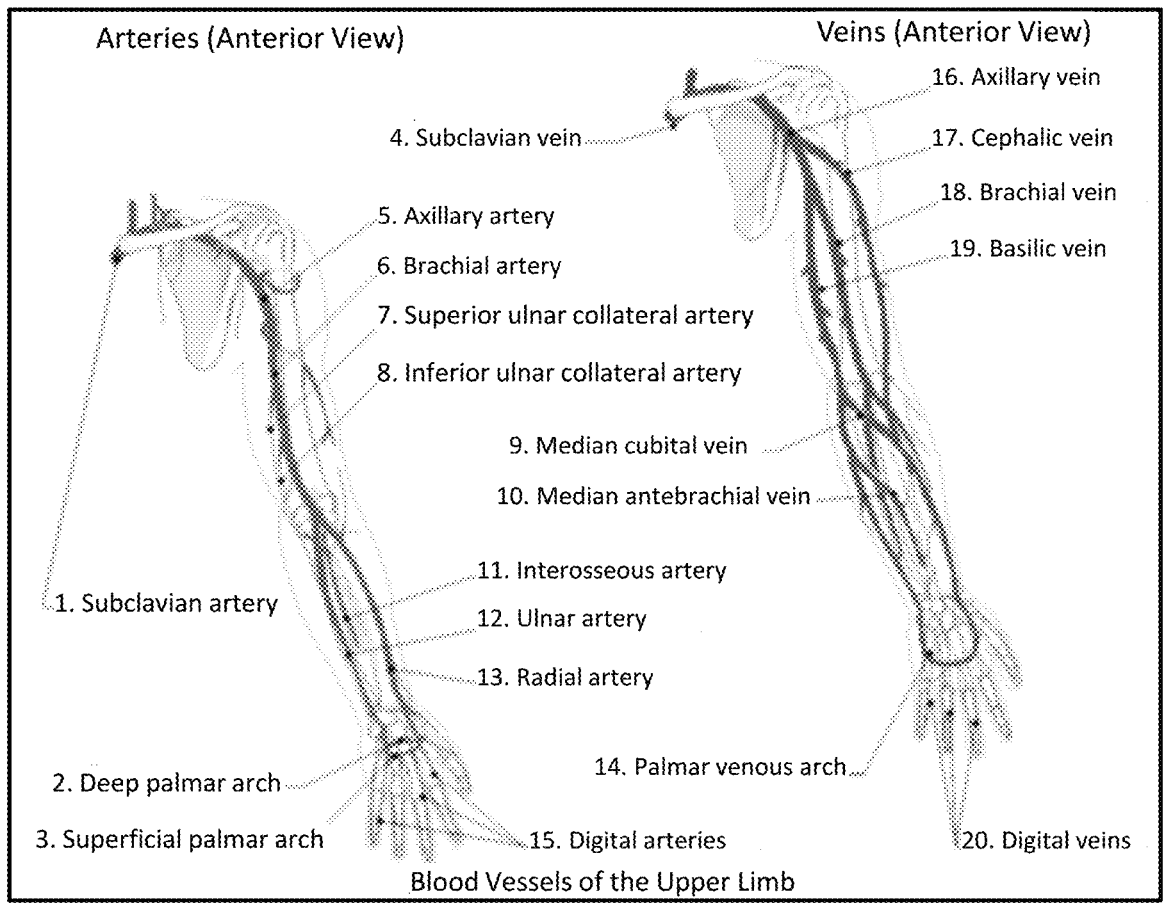
FIG. 20: A schematic of major blood vessels of the left upper limb (closer to heart).

The effective burn treatment is possible only when the right governing principles and fundamental laws of science are applied to develop effective protocols/regimens as such that the present disclosure offers a method to simultaneously pump $Na^+$ ion across the transdermal route as soon as the gel mixture formulation is spread over the affected burn areas and their vicinities while the highly concentrated localized potassium ($K^+$) ions are ousted from the affected areas towards the gel mixture formulation (through transdermal route) outside (in vitro) before they begin to disperse into the vast and intricate network of the circulatory (See FIGS. 11 and 20) system (in vivo) with concurrent pH correction in the extracellular fluid.

Therefore, in case of severe burn injury, it is indispensable to immediately initiate the expulsion of the excess, highly localized and concentrated potassium ($K^+$) ions as well as hydrogen ($H^+$) from blister/extracellular fluid (due to metabolic acidosis) through alternative transdermal routes; bypassing the renal route and thus, safeguarding both kidney and cardiac functions, while entrapping the potassium ($K^+$) ions within (in vitro) the formulation gel mixture which is applied over the skin surface while simultaneously suppressing initial acidosis (pH≤7.35) and checking the subsequent alkalosis (pH≥7.45) and bring back the pH within $7.35 \leq pH \leq 7.45$.

Here, it should be noted that although the diffusional mass transfer is relatively slower process (across the transdermal route) to transport potassium ($K^+$) and hydrogen ($H^+$) ions across the skin surface, yet it traverses relatively much shorter distance/route, for their expulsion or ejection and entrapment into the gel mixture formulation (in vitro) by opening this detour; and thus, averting a much longer route (many thousands of miles) through the vast and intricate network of the circulatory system for their renal excretion.

Therefore, prompt application of gel mixture over the exterior burn injured skin surfaces has multiple benefits. First of all, it ensures quick restoration of regular homeostasis, i.e., to attain quick corrections of the ratio of $Na^+/K^+$ ionic balance, mitigate the initial respiratory and metabolic acidosis ($H^+$ ion invasion in extracellular/blister fluid) to restrict the subsequent alkalosis and prevent ejection of potassium ($K^+$) ions from healthy cells; provided the gel mixture formulation chemistry (pH control ingredients, ion pump, ion exchange compounds, gel chemistry) is optimized, provided it is timely applied, replaced every few minutes and correctly tuned with the exterior and interior chemistry of the skin, blister fluid, vascular and extracellular fluid to restore the normal homeostasis conditions.

Secondly, early initiation of in situ expulsion of potassium ($K^+$) ions (in vitro) from the extracellular or blister fluids prevents induction of any detrimental effects on the cardiac and renal system by restricting the overall increase of potassium ($K^+$) ion concentration, i.e., keeping the concentration within the threshold ($3.5K^+ \leq 5$ mEq/L) limits in allowed in the extracellular/plasma fluid.

Thirdly, early application of the gel mixture formulation helps retard transcapillary fluid loss towards the extracellular fluid and thus prevent excessive blister fluid proliferation due to the rapid in vivo inflow of sodium ($Na^+$) ions in situ through the transdermal route by diffusion.

Fourthly, the organic salt anions (e.g., bicarbonate, acetate, lactate, citrate, $H^+$, $OH^-$ etc.) components of the gel mixture formulation mitigate and neutralize the respiratory, metabolic (lactic acid release from muscle cells and its dissociation in the extracellular fluid) and hyperchloremic acidosis (pH≤7.35) and also mitigate SID imbalances, i.e., the inflow of other anions moving in the extracellular fluid (in vivo) prevent narrowing of SID; which is followed by checking the potassium ($K^+$) ion invasion in serum/extracellular fluid as the pH balanced is swiftly rectified in the extracellular fluid.

Finally, the swift in situ restoration of severe local potassium ($K^+$), sodium ($Na^+$) and hydrogen ($H^+$) ions ion imbalance towards the normal homeostasis; which in turn helps the nerve cells to function to near normal and thus reduce and relieve the severe initial pain.

The application temperatures (~25-38° C.) of gel mixture formulation, the duration of gel mixture application during each period, the frequency of total number of replacements and replenishments of the gel mixtures from the injured skin exterior from the onset of burn shock are also critical for effective and quick pain relief and blister minimization.

Optionally, to speed up potassium ($K^+$) ion expulsion in situ through the transdermal route, the initially applied gel mixture is slowly, softly and periodically need to be re-spread or re-mixed using sterile, soft silicone brush every 2-5 minutes for its effective mass transfer to eliminate any boundary layer ion stagnation or ion accumulation to improve sluggish ion movements or ion stagnation across the transdermal route followed by scraping off the applied gel mixture with subsequent supplementary application of fresh gel mixture formulation over the injured burn skin surfaces in also very critical to maintain steeper pH and ion gradients.

Depending on the severity of the burn injury, the initially applied gel mixture needs to be replaced immediately after scraping away/off (after 2-5 minutes) with fresh gel mixture with re-spreading and remixing over the exterior skin surface for better and faster pain relief too. In case of severe burn injury with over 10 percent TBSA, the applied gel mixture formulation may be replaced every 2-4 minutes to ensure that the potassium ($K^+$) and hydrogen ($H^+$) ions rapidly get purged out in situ, from the extracellular and blister (in vivo) fluid inside the gel mixture Formulation (II) (in vitro) and this periodic replacement should be continued up to two (2) hours (if required) or until the patient is brought to the burn unit or hospitalization. In case of severe over 10 percent TBSA, after continuing with the application of Formulation (I) from the onset of burn injury to approximately 45 minutes to 1 hour or so, Formulation (I) needs to be replaced with Formulation (II) (with pH≤7.35) to minimize hyperchloremia which will be subsequently discussed in detail later.

To prevent hypothermia and faster ion transport via diffusion, the gel mixture formulation should be applied between 25-37° C. for best result. Consequently, as the regular homeostasis is quickly established followed by correction of the cellular action potentials; subsequently, the nerve cells start operating correctly (due to the restoration of $Na^+/K^+/H^+$ ion balance) resulting in faster pain relief, depending on the extent of TBSA and severity of the burn injury.

When negligible chemical reactions are occurring, the Fick's Second Law of Diffusion equation is applicable in the system for the assortment of ion transport via diffusion across solids, semisolid, viscous or stationary liquids is given by the following equation:

$$\frac{\partial c_A}{\partial t} = D_{AB} \cdot \nabla^2 c_A \qquad \text{EQN 9}$$

The solution for the above equation (EQN 9) depends on different boundary conditions, such as diffusion across a thick semipermeable membrane; diffusion across an interface between stirred and unstirred regions; diffusion across a uniform membrane depends on solubility of the ions; and diffusion through the pores. Therefore, the mathematical solution of the governing equation for change in concentration in the x direction (perpendicular to the skin surface) via diffusion with respect to time is dependent on assortment of boundary conditions.

For severely burnt patients with high TBSA (>20%), to maintain constant sodium ($Na^+$) ion pump, the initial concentration for sodium ($Na^+$) ion in gel mixture formulation could be as high as M=5.15 Eq/L (for $Na^+$ ion) at t=0; to impose ion pumping for faster diffusion of sodium ($Na^+$) ions into the extracellular fluid as the in vivo (blister/extracellular/plasma) concentration of sodium ($Na^+$) ion rapidly falls much below ~135 mEq/L due to the transcapillary fluid loss; to control hyponatremia. On the other hand, the initial and local concentration of potassium ($K^+$) ion in the extracellular/blister fluid (in vivo) is $M_{K^+} \geq 5.5$ mEq/L to as high as $M_{K^+} \geq 70$ mEq/L (highly localized concentration in the blister fluid near burn injured areas) is expelled out from the blister and extracellular fluid (in vivo) through the transdermal route, before the potassium ($K^+$) ions get the opportunity to disperse themselves away from the burn shock region and its vicinities along the vast network of the circulatory system. Initially, the outside (in vitro) concentration of potassium ($K^+$) ion, $M^+_K$(in vitro)=0 mEq/L at t=0, in the gel mixture formulation, where the transport of bicarbonate ions ($HCO_3^-$) from sodium bicarbonate ($NaHCO_3$), other anions from organic sodium salts of weak acids supplements and their surrogate ions, viz., hydrogen ($H^+$), hydroxyl ($OH^-$), lactate ions etc. also helps prevent initial acidosis and SID imbalance.

Therefore, simultaneous in situ diffusion of sodium ($Na^+$), hydroxyl ($OH^-$), bicarbonate ($HCO_3^-$) and other salt anions ions towards the blister fluid (in vivo) while the frequent and periodic replacement of gel mixture formulation is expected to transpire into upkeeping of the concentration gradients with simultaneous external (in vitro) expulsion of potassium ($K^+$) and hydrogen ($H^+$) ions via counter diffusional ion transport in the opposite direction (in vitro) towards the gel mixture (as ion sink) towards the externally applied gel mixture formulations; which has been already spread on the skin surface (in vitro).

EQN 9 is applicable for sodium ($Na^+$) and potassium ($K^+$) ions and as well as other anions in the opposite directions for ion transport through transdermal route as long as the concentration gradients never diminish. The significantly higher viscosity of gel mixture formulations impedes both smaller and larger size cations and anion(s) transport outside (in vitro) unless physical mixing and spreading of the gel mixture is intermittently gently mixed over the skin surface. As time progresses, the concentration of potassium ($K^+$) ion is expected to increase in the gel mixture (in vitro) over time. Therefore, for severe burn injury, the applied gel mixture formulation should be replaced every 2-4 minutes to maintain higher concentration gradient.

It should be noted that the rates of diffusivities of ions are dependent on the formula weight of the ions, function of temperature, viscosity of gel mixture formulation etc. Therefore, the gel mixture formulation needs to be spread over the injured skin surface between 25-37° C., preferably near the body temperature right from the onset of the burn injury.

The application of this gel mixture over the injured skin surface above the room temperature, in turn, is going to expedite the in situ diffusion process due to the increased magnitude of diffusivities compared to room temperature. Therefore, in case of ten (10) percent or more TBSA with higher severity and burn depth, the frequency of replacing the gel mixture from the injured skin surface is critical to maintain higher ion concentration gradient as well as removal of any other ions and toxins which may get accumulated in the gel mixture formulations over time.

This process should be repeated until the patient is brought to the medical/clinical facilities or burn units to continue to maintain speedy potassium (K⁺) removal in situ from the burn injured areas and its vicinities. Therefore, this process needs to be made mandatory for severe and deep burn injuries with 20% TBSA; i.e., the scrapping off the already applied gel mixture surface is recommended with enhanced frequency (every 2-4 minutes) from the injured burn surface and its vicinities followed by application of fresh gel mixture formulation. However, Formulation (II) needs to be applied after an hour or so. Therefore, such preventative measure is going to lower the subsequent follow up requirements of the conventional intravenous/oral/enteral fluid resuscitation treatments (usually initiated in the burn units) which usually takes place during the clinical/hospital treatment (when the resuscitation fluid is administered via intravenous or enteral routes usually hour (s) after the burn injury, when the patients are brought to the medical facilities, viz., burn units).

Similarly, burn victims with pre-existing alkalosis; may require lower pH control (7.01≤pH≤7.35) ingredients and would require special Formulation (II) described subsequently in this application. However, this mixture may also be used when initial acidosis is replaced with subsequent alkalosis sometime after the burn injury has occurred and when local extracellular/blister fluids has already accumulated severe potassium (K⁺) ions due to the delay in applying the Formulation (I) right at the onset of burn injury.

For NaCl, ($M_w$=58.5 g/mole), the diffusivity of NaCl in water $D_{AB}$=13.9·10-6 cm²/s. For KCl ($M_w$=76.5 g/mole), the diffusivity of KCl in water $D_{AB}$=13.6·10⁻⁶ cm²/s can be assumed since KCl has larger molecular weight. As an example, for NaHCO₃ ($M_w$=84.01 g/mole), the diffusivity of NaHCO₃ in water $D_{AB}$~(11.7–13.4)·10⁻⁶ cm²/s is assumed since NaHCO₃ (Leaist et al) also has larger molecular weight. These diffusivity values are applicable at 25° C. and can be adjusted for 37° C. during the formulation of the mixture. It is noted that the viscosity (η) of water at 37° C. is 0.70 cP. However, it should be noted that the diffusivity values of Na⁺, K⁺ ions and HCO₃ and other anions would be much lower in the gel mixture media versus water or extracellular/blister/plasma fluid since the gel mixture Formulations (I and II) viscosity is prepared between 100-150,000 cP.

Diffusivity values have been reported for individual HCO₃⁻ ions at various temperatures using molecular modeling method which may be applicable for human body temperature 37° C. However, blister fluid arising from burn shock and its different severity levels would have different diffusion coefficients for ions at different temperatures due to change in burn blister fluid (BBF) composition; therefore, depending on the severity of the burn shock, blister fluids compositions are expected to dictate the diffusivities of the incoming ions (in vivo).

It should also be noted that the diffusivities of ions in general, increases with increasing temperature for liquid, aqueous and viscous system. However, it should be pointed out that the diffusivity of all the above mentioned cations and anions are sluggish in viscous fluid, especially when the viscosity ranges between 100-150,000 cPs. Therefore, it is expected that diffusion process would slow down in in vitro gel mixture formulation unless some form of external physical and manual remixing and re-spreading (with smooth fine sterile silicone brush) of gel mixture can be coordinated after the mixture is spread over the exterior skin layer to enhance mass transfer of the ions. It should be also noted that sodium bicarbonate is broadly used as a physiological buffer in cell culture applications in combination with appropriate weaker acid in combination.

In the present disclosure, sodium bicarbonate and/or other salts of weak acid(s) is/are being deployed as one of the pH control components to control initial acidosis in extracellular/blister fluids. The p$K_a$ for bicarbonate↔carbonic acid reaction is 6.35 at 25° C. The p$K_a$ for bicarbonate↔carbonate reaction is 10.3. Therefore, sodium bicarbonate (NaHCO₃) has two p$K_a$s, 6.35 and 10.3 at 25° C. Sodium bicarbonate (NaHCO₃) is a physiological buffer in vivo conditions, where the equilibrium equations are given by the following:

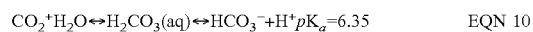  EQN 10

  EQN 11

Therefore, sodium bicarbonate is also used as a component of gel mixture for pH control for in vivo pH management. Thus, the external (in vitro) presence of sodium bicarbonate (NaHCO₃) as one of the pH controlling ingredients in the gel mixture formulation also serves as supplemental dissolved sodium (Na⁺) ions, in addition to already dissolved sodium chloride (NaCl), plus sodium (Na⁺) ions from biocompatible sodium salt(s) of weak organic acids (e.g., sodium lactate, sodium acetate etc.) as components of the pH control ingredients, in addition also acts as sodium (Na⁺) ion pump when the mixture is spread over the burn injured skin surfaces and its vicinities to increase sodium (Na⁺) ions concentration in blister and extracellular fluids to rapidly abate hyponatremia (Na⁺≤135 mEq/L), thereby, pushing back or restricting or minimizing intravascular transcapillary fluid leakage into extracellular, interstitial space that causes blister formation when the fluid begins to accumulate inside the blister/extracellular fluid in the interstitial space beginning from the onset of burn shock.

Therefore, the blister fluid accumulation is minimized by resisting and rectifying (hyponatremia), i.e., increasing Na⁺ ion concentration within (135≤Na⁺≤142 mEq/L) usual boundary limits in the blister, extracellular, vascular fluid while simultaneously restricting the transcapillary fluid loss via external sodium (Na⁺) ion pumping. This in turn, would significantly retard blister fluid accumulation, swelling and subsequently prevent the blister membrane to become less vulnerable to mechanical deformation, thinning and in some cases, rupture.

Simultaneously, it is also critical to rapidly remove highly concentrated local (in vivo) potassium (K⁺) (due to cell lysis, tissue necrosis and initial acidosis) and hydrogen (H⁺) ions in situ via counter diffusion (in vitro) from blister fluid or edema into the externally applied gel mixture formulation from the very initial stages of the burn shock before their dispersion (or spreading out) of potassium (K⁺) and hydrogen (H⁺) ions throughout the vast and intricate network of the circulatory system via viz., diffusion, capillary flow and momentum transfer to cause systemic hyperkalemia which may start as early as few minutes after the burn shock depending on the severity. Therefore, this mixture should be made readily available in work places, e.g., as well as residential and commercial settings as a part of any first aid kit. The accessibility of such mixture requires that this type of gel formulation mixture needs to be ubiquitously available as off the shelf medication as first aid treatment as such that the Formulations (I and II) are readily available and made accessible near any burn accident prone work areas, viz. kitchen, restaurants, coffee shops, machine shops, car mechanic shops, any industrial settings etc.

On the contrary, any delay in the application of this mixture may allow relatively faster blister formation in conjunction with initial acidosis in the extracellular fluid and internal dispersion of the highly concentrated locally released K⁺ ions (after their subsequent release from the cell lysis, tissue necrosis and assortment of acidosis) from the injured burn areas (e.g., blister fluid, zone of necrosis etc.) to disperse themselves throughout the vast network of the circulatory system. Although, the dispersion would indeed reduce the local (near the burn injured areas) potassium (K⁺) ion concentration, however, the average overall potassium (K⁺) ion concentration may surpass well above 5.5 mEq/L and thus would create near fatal or fatal conditions for the patients' survival, since several organs are very sensitive to minute changes in potassium (K⁺) ion concentration rise.

The ideal timing to apply this gel mixture formulation, for best result, is its application right at the onset of burn shocks over the local burn injured areas and its vicinities. This is the ideal zone of the Formulation (I) are the areas where maximum potassium (K⁺) ion concentrates locally, i.e., near the burn injured areas at the beginning of the burn shock and from these locations the removal of potassium (K⁺) and hydrogen (H⁺) ions from extracellular fluid should be maximized through the transdermal route (in situ), as this is where the potassium (K⁺) ion concentration gradients reach their maxima; thereafter, potassium (K⁺) ions starts dispersing throughout the vast and intricate network of the circulatory system unless initially applied gel mixture formulation is not frequently replaced (every 2-5 minutes) over next hour (Formulation I). In case of any delays or with patients with preexisting alkalosis, Formulation II is more applicable.

In the absence of any such external or internal intervention (or treatments) to mitigate potassium (K⁺) ion concentration, the undesirable dispersion potassium (K⁺) ions remains unchecked, almost right after any severe burn injury, after which the overall potassium (K⁺) ion concentration may reach and surpass danger level (5.5 mEq/L) in the extracellular, intravascular and blister fluid. In addition, also due to the unrestricted continuation of hypovolemic shock, resulting in excessively large quantities of extracellular fluids in the interstitial spaces, the cardiac and renal failures may become a morbid reality due to the imbalances in the electrophysiology in the patient's body.

At the beginning, the local extracellular/intravascular/blister potassium (K⁺) ion concentration spikes (See FIGS. 14 and 17) much above the threshold limit of homeostasis, however, after potassium (K⁺) ion dispersion over time, the potassium (K⁺) ion concentrations apparently drops, yet may easily overshoot the maximum limits of regular homeostasis condition. From this point onwards, after the dispersion, the alkalosis condition would begin and replace initial acidosis in the extracellular fluid and at this point, even with the application of gel mixture Formulation (II), it may become rather difficult to purge out the potassium (K⁺) ions in situ, as the final potassium (K⁺) ion concentration gradient across the transdermal route becomes much flatter even near the burn injured areas (e.g., blistered areas) compared to the initial stages at the onset of the burn shock; therefore, the subsequent rate of the potassium (K⁺) ion expulsion in situ through the transdermal route becomes very sluggish if the application of Formulation (I) is delayed. Moreover, if the overall potassium (K⁺) ion concentration surpasses alarming levels (K⁺≥5.5 mEq/L) in the extracellular/plasma fluid, it would cause destabilization or dysfunction of cardiac and renal functions because these organs are very vulnerable to even small elevation of K⁺ ion concentration.

On the same note, even with the application of the gel mixture Formulations (I or II) and their frequent replacement, as the potassium (K⁺) ion concentration gradient across transdermal route (near blister areas) eventually becomes relatively less steep, thus rapid in situ potassium (K⁺) ion expulsion from the blister or extracellular fluids becomes relatively much less efficient and slower through the transdermal route. It should be critically noted that severe hyperkalemia (serum K⁺≥6.5 mEq/L), initial acidosis (H⁺ ion invasion in extracellular fluids from metabolic activity) followed by alkalosis etc. are all potentially life-threatening electrolyte disorders that has been reported to occur in 1% to 10% of all hospitalized patients (See FIG. 6) and constitutes a medical emergency requiring immediate treatment.

Mixture Preparation

The following are the shared ingredients for preparing assortments of customized formulations:

Active Ingredients: Pharmaceutical/clinical and/or food grade sodium chloride (NaCl), and sterile & DI water are one of the primary ingredients for the formulation(s). Biocompatible pharmaceutical grade sodium salts of weak acids, viz., sodium bicarbonate (NaHCO₃), sodium acetate (CH₃COONa), sodium lactate (CH₃CHCOONa), trisodium citrate (C6H5O7.3Na), etc. are required at various concentrations and different combinations to create external pH control additives externally in the formulations for adjusting the internal pH of the burn injured patients with initial acidosis followed by subsequent alkalosis with simultaneous SID management. Pharmaceutical grade liquid strong cationic (sodium) polyelectrolytes such as water-soluble cation (Na⁺) exchange oligomers or water-soluble strong cation exchange polyelectrolytes, e.g., sodium polystyrene sulfonate (Na-PSS; Kayexalate), sodium polyacrylate (combinedly ≤300 ppm or less preferably 200 mg/L to avoid skin rash) etc. are also considered as part of sodium (Na⁺) ion pump constituents to avoid chloride (Cl⁻) ion invasion in extracellular/fluid and thus minimize hyperchloremia thereby shielding or minimizing the narrowing down of SID from its usual/normal range. All ingredients must meet pharmaceutical/clinical/food grade specifications.

Water soluble, biodegradable and natural biopolymers are used as viscosity modifiers which also acts as reservoir for maintaining high concentration of sodium (Na⁺) ion components, viz., sodium chloride (NaCl) in ionic form (as Na⁺ ions), non-crosslinked cation (Na⁺) ion exchange polyelectrolytes, e.g., sodium polystyrene sulfonate (Na-PSS; Kayexalate), sodium polyacrylate and also polyacrylic acid (combinedly 300 mg/L and less preferably 200 mg/L to avoid skin rash) including pH control components (sodium bicarbonate, sodium acetate, sodium lactate, sodium citrate or other biocompatible sodium (Na) salts of weak organic acids).

These sodium salts of weak acids (Formulation I) and in some cases (Formulation II) salts of weak acids and their parent acids in various concentrations and in different combinations are capable of creating either pH levels (between pH 7.55≤pH≤10.0) to mitigate initial acidosis (pH≤7.35) in Formulation (I); or to create pH levels (~pH, 7.01≤pH≤7.35) to mitigate the subsequent alkalosis (pH≥7.45) in extracellular/blister/plasma fluid with the application of Formulations (II) respectively. (Please note Tables 1 and 2 as examples).

For assortment of patients, the gel matrix formulation base may be created with natural sugar based unsubstituted and/or sodium ((Na⁺) substituted polymer/oligomers, viz., water soluble cellulose derivatives, e.g., CMC, HEC, *xanthium* gum, guar gum, gum Arabic and their derivatives etc. dissolved in sterile and DI water.

Patients with preexisting alkalosis (pH≥7.45), non-crosslinked polyacrylic acid and/or other biodegradable oligomers/polymers and/or their sodium (Na) substituted derivatives, viz., such as hexose sugar and their derivatives including derivatives of cellulosic (glucose) oligomers/polymers, viz., carboxymethyl cellulose (CMC), hexaethyl cellulose (HEC) etc., pentose sugar oligomers/polymers and their derivatives, other sugar derived derivatives, viz., guar gum, gum Arabic etc. could be used as base for the gel matrix or gel substrates dissolved in sterile and deionized (DI) water where concentrated ionized sodium chloride (up to 5.15 Eq/L) is used in dissolved forms including pH control ingredients/additives, viz., sodium bicarbonate, sodium acetate and sodium lactate etc. in various combinations which are also in dissolved form in DI and sterile water to manage initial acidosis in Formulation (I). Formulation (II) requires pH control additives including lactic acid, acetic acid, boric acid, citric acid, sodium lactate and sodium citrate etc. in various combinations to create level ($7.01 \leq pH \leq 7.35$) to mitigate the subsequent alkalosis, if not prevented beforehand. For example, specialty cellulose derivative, viz., ethyl hydroxy-ethyl cellulose (HEC) has a degree of polymerization DP≅400-2000, which corresponds to high molecular weight, is used as viscosity modifiers as an example.

As additional examples, since most of the cellulose derivatives have variable and high polydispersity index (PDI) due to variable source of parent sugar based polymers, e.g., cellulose or its derivatives; as a result, the mixture should be prepared as such the final viscosity in the Formulation (I) is experimentally adjusted with respect to pH control component concentration (to adjust internal extracellular fluid pH within $7.35 \leq pH \leq 7.45$, sodium chloride up to 5.15 Eq/L in concentration and with right amount of sterile and DI water in the final composition. Similar Formulation (II) could be prepared with lower sodium chloride concentration.

It should be noted that due to the variation in polydispersity index, the final viscosity of the gel mixture must be corrected during the final mixing process. The combined gel mixture should have a kinematic viscosity of 100-150,000 mm²/s (cP) at (~20° C.) for assortment of patients with both initial acidosis and subsequent alkalosis conditions. The mixture formulations that should be in semisolid or viscous and gel matrix form so that its fluidity is retarded in comparison with the aqueous solution to maintain as a slow-moving viscous fluid when subjected to mechanical or gravitational or shear forces. However, it should be amenable to easily being washed away by sterile and deionized (DI) water or scraped away by silicone brush or similar soft tools anytime during the treatment.

DI and sterile water with lower level of pH control (pH between $\sim 7.01 \leq pH \leq 7.35$) ingredients are required in gel matrix Formulation (II) for patients with preexisting alkalosis pH (≥7.45) in special cases, to formulate a gel mixture formulation with above mentioned viscosity modifiers to create gel matrix with pharmaceutical grade sodium chloride (NaCl up to ~5.15 Eq/L) and/or cationic ion exchange compounds, non-crosslinked sodium substituted polyelectrolytes, e.g., sodium polyacrylate, polyacrylic acids and other sodium substituted water-soluble sugar based polymers/oligomers.

Gel Mixture Formulation for Regular Burn Victims to Minimize Hyperkalemia and Initial Acidosis Deionized (DI) and sterile water is the primary solvent for dissolving the mixture components. Here, also the gel mixture substrate is prepared by the above-mentioned common polymer/oligomer ingredients, non-crosslinked polyacrylic acid & sodium polyacrylate (≤300 ppm and less preferably 200 mg/L to avoid skin rash), cation exchange soluble resins, e.g., non-crosslinked sodium polystyrene sulfonate (Na-PSS; Kayexalate) etc.

Pharmaceutical/clinical grade sodium chloride is used (up to 5.15 Eq/L) to create a hypertonic salt solution in sterile DI water containing sodium ($Na^+$) for its subsequent use to form the gel mixture substrate. This hypertonic sodium ($Na^+$) ion containing salt gel mixture helps prevent mass transfer of water from the gel mixture formulation into the blister or edema fluid, however, may also draw (in vivo) water outside through the transdermal route. This hypertonic salt containing sodium ($Na^+$) ions in the formulations pump ($Na^+$) ions into the extracellular/blister/edema fluid to rectify hyponatremia (within $135 \leq Na^+ \leq 145$ mEq/L) in those interior extracellular/plasma fluids. The dissociation of sodium salts of weak organic acids (including sodium bicarbonate, sodium acetate, sodium lactate etc.) in the Formulation (I) also corrects the initial intravascular/extracellular acidosis either by neutralizing hydrogen ($H^+$) ions from the dissociation of lactic acid from metabolic acidosis, or by supplying hydroxyl ($OH^-$) ions from in vitro or expelling out hydrogen ($H^+$) ions in vitro through transdermal route via ionic diffusion, whereas the incoming lactate ions prevents dissociation of lactic acid in the extracellular fluid by Le Chatelier's principle.

In a typical preparation protocol (Formulation I), pH controlled ingredients may or may not be comprised of sodium ($Na^+$) ion based buffers (weak organic acid and their sodium salts or combination of sodium salts with two acid dissociation constants with $pK_{a2}$) and/or combination of sodium bicarbonate/sodium carbonate ($NaHCO_3/Na_2CO_3$) and/or other sodium salt mixtures of biocompatible weak organic acids, e.g., sodium lactate, sodium acetate ($CH_3COONa$) and/or trisodium citrate etc. are added in combination or separately in the right amount to create pH control gel mixture Formulation (I), mimicking (up to pH~$7.7 \leq pH \leq 10.0$) as such that after application of this gel mixture it helps maintain the extracellular serum or blood plasma pH ($7.35 \leq pH \leq 7.45$). During such mixture preparation, such pH adjustments needs to be carried out using a calibrated pH meter and estimation protocol similar to shown in Examples 1 through 4 to determine and estimate the final pH of the Formulation (I) while continuously monitoring the final pH of the gel mixture for a minimum of 30 minutes.

Other sodium salts of organic weak acids (e.g., lactic acid, trisodium citrate, acetic acid etc.) with right base/acid dissociation constant ($pK_b/pK_a$) values are the other examples to create appropriate buffered pH control in gel mixture formulation(s) (pH up to ~$7.7 \leq pH \leq 10.0$) as the combined salt mixtures is used to adjust the internal pH of blood plasma/serum/extracellular fluid during the initial acidosis condition. In addition, the transport of the anions in the extracellular fluid from those above-mentioned gel matrix Formulation (I) also help maintain SID. Tables 1 and 2 provide examples of pH control ingredients in the gel mixture Formulations (I and II).

The mixture/formulation should have moderate pH control capacity; therefore, right concentrations of salt(s) of acid(s) are used to prepare gel mixture Formulation (I) with pH control capacity (examples shown in Tables 1 and 2). It is preferable to use predominantly bicarbonate ($HCO_3^-$) anions and sodium ($Na^+$) cations in combination with sodium ($Na^+$) cations and lactate salt anions in the gel mixture preparation as well as pH control components in the gel mixture Formulation (I) to mitigate initial acidosis in the extracellular fluid and blood plasma or serum since these fluids contains both of these ions as buffer components. However, salts with potassium ($K^+$) ions which are components of pH control ingredients must be avoided in the gel mixture formulations as it would aggravate hyperkalemia in the serum/extracellular/blister fluid. It should be noted that in blood plasma/serum/extracellular fluid, the buffer is naturally created by dissolved carbon dioxide ($CO_2$) as aqueous carbonic acid ($H_2CO_3$) and bicarbonate ($HCO_3^-$) anions inside the human body that follow the Henderson-Hasselbalch equation.

All salt (s) of the organic acids must be biocompatible to prepare the pH-controlled gel mixture formulation(s). Here, water soluble and biocompatible organic sodium salts are dissolved in deionized (DI) and sterile water to create the pH control agent. The matrix formulation may be created either from sodium (Na) substituted non-crosslinked sodium polyacrylate or other biodegradable and water soluble oligomers/polymers derivatives, viz., such as hexose sugar and their derivatives including derivatives of cellulose (glucose) oligomers/polymers, viz., carboxymethyl cellulose (CMC), hexaethyl cellulose (HEC) etc., pentose sugar based oligomers/polymers and their derivatives, other cellulose derivatives as base/foundations for the gel matrix or gel substrate dissolved in sterile and deionized (DI) water where concentrated sodium chloride and sodium salts of biocompatible organic weak acids also remain in dissolved form.

Alternatively, for Formulation (II), sodium chloride (NaCl) can also be added in lower concentrations (2.25 Eq/L) in the DI and sterile water, however, which must be above the concentration of $Na^+$ ions present in blister fluids to maintain higher concentration gradient to sustain the $Na^+$ ion pumping during the transdermal diffusion process to rectify hyponatremia.

Formulation (II) is added as a follow-up application if the treatment is delayed or after 30 minutes have elapsed after the application of Formulation (I). The combination of salt mixture ingredients present in the Formulations (I/II) independently have a synergistic effect on simultaneously mitigating the acidosis (Formulation I), alkalosis (Formulation II), hyponatremia and hyperkalemia in the extracellular/blister fluid and other organs. These gel mixture formulations should not be applied over punctured blisters since high concentration of sodium chloride (NaCl) may cause severe irritation below the skin surfaces.

Gel Mixture Formulation (I) for Regular Burn Victims (with Pre-Existing Alkalosis)

The matrix formulation may be created especially for patients with preexisting alkalosis by adding non-crosslinked polyacrylic acid & sodium salt of polyacrylic acid ($\leq 300$ ppm or less preferably 200 mg/L to avoid skin rash), sodium exchanged water-soluble non-crosslinked polymers or other biodegradable oligomers/polymers derivatives, viz., such as hexose sugar and their derivatives including derivatives of cellulose (glucose) oligomers/polymers, viz., carboxymethyl cellulose (CMC), hexaethyl cellulose (HEC) etc., pentose sugar oligomers/polymers and their derivatives, cellulose derivatives, could be used as a base for the gel matrix or gel substrates dissolved in sterile and deionized (DI) water where all including concentrated ionized sodium chloride (up to 2.25 Eq/L) remains in dissolved form.

For patients with alkalosis and hyperkalemia, the pH control components including sodium ($Na^+$) ion containing buffers and/or combination of various biocompatible sodium (Na) salts of organic acids, e.g., sodium lactate (and lactic acid), trisodium citrate (and citric acid), sodium acetate (and acetic acid) etc. (as shown in Tables 1 and 2 as examples) and/or their corresponding weak organic acids remain in various combinations along with/without dissolved sodium bicarbonate ($NaHCO_3$) in gel mixture Formulation (II) to create lower pH~($7.01 \leq pH \leq 7.35$) which is used to prepare the gel mixture Formulation (II) for these special case patients. It should be noted that the ratio of acid anion(s) to their corresponding acid(s) counterpart(s) must be greater to create mild acidic to mildly alkaline condition ($7.01$ pH$\leq 7.3$). Such gel mixture formulation(s) should be easily washed away by sterile and deionized (DI) water or scraped away by soft silicone brush or similar tools anytime during the treatment.

In case of severe burn injury and high TBSA, more frequent (2-4 minutes) replacement of gel mixture is a necessity when excessively high concentration of potassium ($K^+$) ions is expected to surge locally within and near the blister fluid, extracellular and edema fluid due to cell necrosis/lysis and metabolic acidosis followed by expulsion of potassium ($K^+$) ion expulsion from healthy cells due to hydrogen ($H^+$) ion intrusion in healthy cells. Therefore, depending on the depth of the burn injury and percent TBSA, to sustain higher rate of sodium ($Na^+$) ion diffusion into and counter diffusional expulsion of potassium ($K^+$) ions from the interior to the external mildly acidic to mildly alkaline gel mixture Formulation (II) with frequent fresh gel mixture replacement at higher frequency helps rapid ouster of the relatively highly concentrated and locally accumulated potassium ($K^+$) and hydroxyl ($OH^-$) ions from the extracellular/blister fluids through the transdermal route before these ions also begin to disperse throughout the vast and intricate network of the circulatory system.

Such application of this mixture on the burn injured area and its vicinities is also focused towards subsequently minimizing the volume requirement of the conventional resuscitating fluid administered during the follow up clinical treatments in burn units, viz., where various intravenous fluid resuscitation is initiated during the subsequent hospitalization period where over resuscitation may sometimes become a problem due to undesirable "fluid creep."

In effect, rapid transdermal ionic restoration of ionic balances is offered through the gel formulations herein at the onset of burn shock that would minimize subsequent "fluid creep" as the conventional clinical resuscitation needs are significantly diminished for the burn injured patients. This in turn, would restrict the overall increase in the potassium ($K^+$) ion concentration in the intravascular and extracellular fluid as such that the risks of cardiac arrest/failure and renal failure are significantly reduced.

It should be noted from FIG. 6 that patient death sharply increases as vascular and extracellular potassium ($K^+$) ion concentration surges above 5.5 mEq/L concentration. Therefore, immediate application of the gel mixture Formulation (I) as first aid treatment as first response at the onset (within minutes) of the burn injury or burn shock requires its instant availability as household first aid treatment solution. However, if treatment is delayed or patients with severe hyperkalemia of alkalosis, Formulation (II) is a more reliable treatment. Here, it is again reiterated, that the combination of salt mixture and their parent acids as buffer ingredients and sodium ion ($Na^+$) ions present in the Formulations (II) helps rectify alkalosis, hyperkalemia and hyponatremia simultaneously and have a synergistic effect on mitigating the alkalosis (Formulation II) to restore normal homeostasis in the extracellular/blister fluid and other organs.

All percentages and ratios used herein are by Eq/L and mEq/L of the total composition and all measurements made are between 25-37° C. unless otherwise noted. All percentages, parts and ratios are based upon the molarity of the compositions of the present disclosure, unless otherwise specified. All such weights as they pertain to listed ingredients are based on the active level and, therefore, do not include solvents or by products that may be included in commercially available materials, unless otherwise specified.

Application of the Gel Formulation Mixture Over Burn Injured Surface Areas

This gel mixture Formulations (I and II) is only applicable for burn injuries resulting from hot food & drinks, hot objects, steam, electrical burn injuries etc., i.e., for First and Second-degree burns; it is not applicable for chemical burn injuries or third degree burn injuries where exterior skin is damaged or got peeled off or punctured. Any pretreatment, viz., application of ice, water cold or warm water on the burn injured area are highly detrimental and strictly discouraged or forbidden prior to applying this gel mixture formulation on the burn injured skin area and its vicinities. For best results, the Formulations must be applied at the onset of burn injury. Soft silicone type brush, facial tissue or very soft cloth type material could be used to allow uniform mixing to enhance ionic diffusion and mass (ion) transfer. In case of second-degree burn, it should be ensured that clothing, watches, or jewelry near or covering the surrounding burned area must be removed too.

For optimal results, the gel mixture formulations must be profusely spread over the burn areas for deep and higher total burn injured areas (TBSA) over 10-20%, its vicinities and strategic locations at the very onset of the burn shock to quickly minimize blister proliferation, pain management, hyponatremia, hyperkalemia, initial acidosis, follow-up alkalosis, prevent blister rupture and/or skin damage from blister damage/rupture/puncture.

Soft silicone type brush, facial tissue or very soft cloth type material could be used for scraping off gel mixture formulation from the injured skin surface and its vicinities in case of severe burn which may require recurrent replacement of gel mixture formulation as the increased amount of potassium ($K^+$) ions may accumulate at the interface between the skin and the applied gel matrix formulations as time progresses.

For up to 10% TBSA, the applied gel mixture formulation may be replaced every 3-5 minutes for better results, while for more than 10% TBSA the frequency of replacement should be between 2-4 minutes. In special cases, patients' arms, limbs, torso etc. could be dipped into a bath filled with such gel mixture formulations for faster actions and pain relief. It is important to understand the simplified schematics of human circulatory system (See FIGS. 11 and 20) of human body and the spectrum of chemical excretions and their composition from different regions of the skin surfaces to provide additional protection, i.e., applying the gel mixture formulations to enhance further ionic mass transfer via transdermal routes.

For example, if there is a large injury over upper limb areas, gel mixture formulations may be profusely applied inside the armpit areas as such that major blood vessels (major/minor arteries) and extracellular fluids near the armpit areas (See FIGS. 11 and 20), carrying higher concentration of potassium ($K^+$) and hydrogen ($H^+$) ions could discharge these ions (in vitro) outside in the gel mixture formulations to counter hyperkalemia and acidosis; whereas the sodium ($Na^+$) and hydroxyl ($OH^-$) ions are supplied (in vivo) from the formulations to rectify hyponatremia and acidosis while maximizing diffusional ionic mass transfer and maintain higher concentration gradients before the extracellular fluid or blood plasma gets the opportunity to disperse the potassium ($K^+$) and hydrogen ($H^+$) ions across the circulatory system and damage the cardiac and renal functions.

In another example, the formulations may also be profusely applied all over groin areas for injuries covering large areas in the lower limb regions to protect the rectify acidosis, hyperkalemia and hyponatremia. Here, it should be borne in mind that both the armpit and groin regions are in general acidic in nature as the sweat glands in those regions excrete (as they discharge higher levels of perspiration, e.g., 3-methylbutanoic acid, E-3-methylhex-2-enoic acid, 3-hydroxy-3-methylhexanoic acid, isovaleric acid or 3-methyl butanoic acid etc.) higher levels of organic acids, and therefore, the applied formulation needs to be replaced very frequently to maintain higher diffusional ionic mass transfer, maintain larger concentration gradients to neutralize organic acids (released from sweat glands) in vitro as well as neutralize excess hydrogen ($H^+$) ions dissociated from lactic acids during burn injuries.

Most importantly, the treatment must begin with the application of the formulations of over the burn injured areas and their vicinities. The optimum temperature of the mixture during its application is between 25-37° C. to avoid hypothermia and enhance higher rate of ionic diffusions. For regular burn victims, application of Formulation (I) is highly encouraged from the onset of burn injury to minimize physiological disorders as the initial damage control procedure.

For burn patients with preexisting hyperkalemia and alkalosis, appropriate mildly acidic to alkaline ($7.01 \leq pH \leq 7.3$) gel mixture Formulation (II) may be applied all over the skin surface except, eyes, nose interior, ear interiors to mitigate hyperkalemia by allowing excess removal of potassium ($K^+$) ions via transdermal routes to rectify and maintain the optimum homeostasis conditions, i.e., to resist any slight changes in $K_i^+/K_e^+$ ratio. The application of Formulation (II) particularly important for kidney patients with preexisting hyperkalemia conditions for both acute and chronic situation. In addition, the mildly acidic to mildly alkaline pH ($7.01 \leq pH \leq 7.3$) present in Formulation (II) would also help remove excess hydroxyl ($OH^-$) ions via transdermal ionic diffusion from the blister/extracellular fluid to restore the homeostasis pH balance.

Addition of one of these salts and their combinations with right concentration would create different pH levels required for the gel mixture Formulation (I) and Formulation (II) that would prevent initial respiratory and metabolic acidosis as well as subsequent alkalosis.

EXAMPLES

Additional detailed embodiments of formulations are described as Examples, which should not be viewed as limiting the scope of other embodiments previously described.

The purpose of gel formulation matrix, with the ingredients present inside, would provide the basis for the remediation from the burn injuries which are described below:
1. Prevent/rectify acidosis (pH≤7.35) in the extracellular/blister/plasma fluid.
2. Prevent/rectify subsequent alkalosis (pH≥7.45) in extracellular/blister/plasma fluids.
3. Prevent increase in the potassium ($K^+ \geq 5.5$ mEq/L) ion concentration in the extracellular/blister fluid) if applied at the onset of the burn shock injury.

4. Expel excess potassium ($K^+$) ion from the local extracellular/blister fluid through the transdermal route outside into the gel formulation matrix to prevent hyperkalemia ($K^+ \geq 5.5$ mEq/L).
5. By imposing a strong sodium ($Na^+$) ion gradient, sodium ($Na^+$) ion transport is enforced from the gel matrix formulation by diffusion through the transdermal route inside into the local extracellular/blister fluid to minimize hyponatremia ($Na^+$) and also the translocation of vascular (blood vessel) fluid.
6. Therefore, immediate application of the gel mixture formulation on the burn injured areas and their vicinities would help rapid rectification of local sodium (within $135 \geq Na^+ \geq 145$ mEq/L); rectification of the pH ($7.35 \geq pH \geq 7.45$) in the local and overall extracellular/blister fluid; rectification of local potassium (within $3.5 \geq K^+ \geq 5.0$ mEq/L) ion balance, which may locally skyrocket abnormally to as high as ($K^+ \geq 70$ mEq/L) concentration; to help rapidly restore the normal functioning of neural, cardiac, skeletal and renal functions before the displaced potassium ($K^+$) ions disperses into the vast network of the circulatory system, thus restricting the overshoot of overall potassium ($K^+$) ion concentration in the extracellular fluid before their renal excretion and thus preventing the potassium ($K^+$) overload on the renal system.
7. Specifically, the rectification of sodium ($Na^+$) and potassium ($K^+$) ion concentrations in the local extracellular/blister fluid would gradually help manage pain within hours due to the quicker restoration of the action and resting transmembrane potentials of the neural cells within and around the burn injured areas and its vicinities.
8. In addition, the rectification of sodium ion concentration in the extracellular fluid within the normal homeostasis ($135 \geq Na^+ \geq 145$ mEq/L) condition and that would also help pushback rapid translocation or transcapillary plasma/serum fluid loss from blood vessels into the extracellular fluid in the interstitial space, thus preventing excessive fluid load on the renal system.

Purpose of Aqueous Gel Matrix Formulation
1. Create an aqueous gel matrix reservoir for sodium chloride (NaCl) in dissolved ionic form, i.e., to create concentrated sodium ($Na^+$) ion pump to transport through the transdermal route via diffusion.
2. Create a reservoir to dissolve other sodium salts of several other weak organic acids to pH destabilization, viz.,
2A. Create pH Pump: The pH pump (created by the mixtures of organic acid salts at different concentration) is deployed to balance (increase/decrease) the pH (in vivo) of the extracellular/blister fluid due to burn shock injuries using dissolved in the gel mixture formulation(s) via diffusion. (pH control calculation as shown in the Examples 1-4, Table 1). The initial burn shock injury causes acidosis (pH decrease) followed by alkalosis (pH increase). Therefore, at the onset of the injury (acidosis), Formulation (I) needs to be applied on an immediate basis. If the application gets delayed or patients with pre-existing hyperkalemia (alkalosis), Formulation (II) has to be applied over the burn injured skin surfaces, since by that time alkalosis may have already started or spread.
2B. In addition, supplying/transporting assortment of anions, viz., bicarbonate, acetate, lactate, citrate ions of sodium salts in various combinations from the gel matrix formulation into the extracellular/blister fluid would also balance Strong Ion Difference (SID) in the extracellular/blister fluid.
2C. These anions may also serve as counter ions for outgoing/expelled potassium ($K^+$) ions via the transdermal route into the gel mixture formulation matrix, depending on the direction of the concentration gradients of different anions.
3. The gel mixture formulation matrix also serves as a sink to receive the expelled potassium ($K^+$) ions through the transdermal route by counter diffusion from the extracellular/blister fluid region with anions and chloride ions as counter ions to capture the expelled potassium ($K^+$) ions.
4. The gel mixture formulation is viscous (100-150000 cP) and semisolid in consistency as such that it resists the flow of gel mixture formulation or only allow slight and slow slide over the skin surface resisting the gravitational flow.
5. The gel (polymer/oligomers) are chemistry has polarity due to the electronegativity difference between the constituent elements. The gel is prepared by dissolving the polymers/oligomers in DI water.
6. High molecular weight biopolymers/oligomers of hexose and/or pentose sugar derivatives, e.g., carboxymethyl cellulose (CMC), hexaethyl cellulose, pectin, etc. can is used in various combinations as gel formulation matrix which are all soluble in water.
7. High molecular weight water soluble poly ethylene glycol can also be used as gel formulation matrix ingredients in combination with the above-mentioned biopolymers/oligomers or as a standalone polymer.
8. Non-crosslinked polyacrylic acid (300 ppm or less 300 mg/L, preferably 200 mg/L to avoid skin rash) or sodium polystyrene sulfonate (Na-PSS; Kayexalate) can be added as additive in polymer/oligomers gel mixture formulation as ion exchange compounds to exchange some of the incoming potassium ($K^+$) ions and lessen the risks of hyperchloremia in the extracellular/blister fluid.
9. Sodium salts (300 mg/L or less 300 mg/L, preferably 200 mg/L to avoid skin rash) of polyacrylic acid and/or sodium polystyrene sulfonate (Na-PSS; Kayexalate) can be added to the gel mixture formulation as ion exchange compound to exchange some of the expelled potassium ($K^+$) ions and lessen likelihoods of hyperchloremia in the extracellular/blister fluid.
10. The nature of gel chemicals is discussed below.

Ingredients in the Gel Matrix Formulation
It should be noted that the gel could be a dissolved single polymer/oligomer derivative or a mixture of more than one polymer/oligomer and their derivatives in sterile and deionized (DI) water in various combinations, viz.,
1. High molecular weight polymers, hexose and/or pentose sugar polymer/oligomer dissolved in sterile water.
2. Polyethylene glycols dissolved in sterile water.
3. Polyacrylic acid and its sodium salts and/or sodium polystyrene sulfonate (Na-PSS; Kayexalate) dissolved in sterile water to ion exchange am potassium ($K^+$) ions in vitro to minimize risks of hyperchloremia in the extracellular/blister fluid.
4. Sodium chloride (NaCl) remains in dissolved state in the gel mixture formulation.
5. Other sodium salts (sodium bicarbonate, sodium acetate, of weak organic acids in different concentrations to create pH (7.5-10, Formulation I) and pH (7.01-7.35, Formulation II) to rectify acidosis and alkalosis respectively. Note that diffusion of atmospheric $CO_2$ in the formulation over time would decrease the overall pH of the gel mixture formulation.

When dissolved in (for our case, sterile and DI) water, these polymers/oligomers and their derivatives assumes a consistency of liquid gel. These polymer/oligomer derivatives are not crosslinked and smaller (shorter in chain length) in degree of polymerization in comparison to their natural precursors, as a result, dissolves in the solution.

To prepare the gel mixture Formulations (I and II), right amount of sodium chloride (NaCl) is dissolved. In addition, for Formulation (I), alkaline condition (pH~7.88) is created by adding sodium bicarbonate ($NaHCO_3$), sodium acetate ($CH_3COONa$) and sodium lactate ($CH_3CH(OH)COONa$) to create the pH~7.88 condition and Formulation (I) must be added at the onset of the burn shock injury. It should be noted that the gel mixture Formulation (I) pH may drop over time (as it sits in the shelves); as the atmospheric $CO_2$ slowly infiltrates/diffuses in the bottle.

This Formulation (I) is applicable to prevent acidosis and Formulation (II) is required for rectifying the subsequent alkalosis in the extracellular fluid and for patients with pre-existing hyperkalemia Formulation (II) must be added at the onset of the burn shock injury. Formulation (II) is prepared with right amount of sodium chloride (NaCl) and sodium lactate and sodium citrate, dissolved in the gel mixture as such that it has lower pH (~7.01-7.3). Now we need to discuss the calculation protocol to determine the pH contribution of these sodium salts of weak organic acids at different concentrations.

As Examples 1-3 indicate, from the numerical values of the $pK_a$ of different organic acids, i.e., which salt anions would produce higher hydroxyl ion concentration after their dissolution in water. Note that $pK_{a1}$ values of different salts placed in descending order: Carbonic acid ($pK_{a1}$=6.35); Acetic Acid ($pK_{a1}$=4.76); Lactic Acid ($pK_{a1}$=3.86); Citric Acid ($pK_{a1}$=2.92). Therefore, according to the above numerical $pK_a$ values, it should be noted that salt of sodium bicarbonate would produce highest pH among the four salts with citric acid being the lowest with same molar concentration.

The anions from sodium bicarbonate ($HCO_3^-$), sodium lactate ($CH_3CH(OH)COO^-$), sodium acetate ($CH_3COO^-$), trisodium citrate ($C_6H_5O_7^{3-}$) etc. also serves several critical roles in the Formulations (I and II), which are as follows:

1. Depending on the concentration of the dissolved salts in the solution (gel mixture formulations), they create different pH levels in the gel mixture formulations and thus, create pH gradients, either to supply hydroxyl ($OH^-$) or hydrogen ($H^+$) ions with respect to pH levels in the extracellular/blister fluid across the skin (transdermal route) to minimize acidosis or alkalosis respectively in the extracellular/blister fluid (see Table 1). Therefore, the higher concentration of the salts of weaker acids (with relatively higher $pK_a$ values) in the gel mixture Formulation (I) would help increase pH levels in the extracellular/blister fluid.

2. At the onset of burn shock injury, the pH of extracellular/blister fluid may fall below pH 7.35 (acidosis), therefore, the gel mixture Formulation (I) must possess pH level higher than 7.7, as such that the formulation mixture can rectify the pH of the extracellular/blister fluid by imposing a pH gradient to supply/transport hydroxyl ($OH^-$) ions into the extracellular/blister fluid via the transdermal route to neutralize acidosis (in vivo), i.e., bring the pH within homeostasis ranges ($7.35 \geq pH \geq 7.45$).

Additionally, all the anions of sodium salts present in the gel mixture formulation are also capable of act as counter ions for (in vitro) potassium ($K^+$) ions after the ions are expelled/transported out from the extracellular/blister fluid (in vivo) via ionic counter diffusion; while simultaneous concurrent sodium ($Na^+$) ion pumping into the local extracellular/blister fluid via diffusion (in vivo) towards the burn injured extracellular/blister/edema fluid are ongoing. The expulsion of potassium ($K^+$) ions is also facilitated by the presence of chloride ($Cl^-$) anions from sodium chloride (NaCl) present in the gel mixture formulation in addition to the other ions. This gel mixture Formulation (I) is applied at the onset of burn shock injury for 2-5 minutes and subsequently replaced every 2-5 minutes with fresh gel mixture formulation for at least an hour to maintain large ion gradients for diffusion ($Na^+$) and counter diffusion ($K^+$).

Subsequently, after an hour or so, another gel mixture Formulation (II) with lower sodium chloride (NaCl) concentration (1 Eq/L) or sodium ($Na^+$) ion pump with lower strength. In addition, this Formulation (II) would contain lower concentration of sodium salts of organic acid mixtures as such that the combined pH of the gel mixture formulation is maintained between 7.01-7.35 to prevent alkalosis from the first Formulation (I). However, both Formulation (I and II) would facilitate potassium ($K^+$) ion expulsion in vitro into the gel matrix formulations.

If the application of the gel mixture Formulation (I) gets delayed by more than five or more minutes, then depending on the severity and Total Burn Surface Area (TBSA), alkalosis (local pH increase above 7.45) in the blister fluid would begin to commence; in that scenario, the gel mixture Formulation (II) or alternate gel mixture formulation must be applied which should be comprised of lower concentration of sodium salt of the organic acids as such that the pH of the gel mixture formulation should be below 7.35 to transport hydrogen ions into the extracellular/blister fluid to adjust the homeostasis pH of the patients back within $7.35 \geq pH \geq 7.45$ level. In addition, the second gel Formulation (II) must be applied for patients with pre-existing hyperkalemia.

The anions from the organic acids would also help cross through the skin (transdermal membrane) to maintain and optimize Strong Ion Difference (SID) in the extracellular/blister fluid depending on the concentration gradient of the anions.

However, it is most important to apply the gel mixture Formulation (I) (for regular patients) at the onset of burn shock injury to minimize blister fluid proliferation by forcing sodium ($Na^+$) ions, prevent/neutralize acidosis (due to the in vitro presence of salt anions leading to the formation of hydroxyl ions and its diffusional entry into the local extracellular/blister fluid) with subsequent minimization of undesirable ejection of significant amount of potassium ($K^+$) ions from the healthy cells into the extracellular/blister fluid. In addition, it would help prevent quick dispersion of locally highly concentrated (as high as 70 mEq/L) potassium ($K^+$) ions in the complex network of the circulatory system as such that the overall potassium ($K^+$) ion concentration would get undesirably elevated from 4 to 5.5 mEq/L and above. Note that a small increase in the concentration of potassium ($K^+$) ion from 4 mEq/L to 5.5 mEq/L and above would severely destabilize the cardiac function.

pH Properties of Different Salts

The calculation protocols of pH change with respect to concentration are given in Examples 1-4.

Example 1

As sodium bicarbonate is dissolved in water, completely dissociates into aqueous sodium ($Na^+$) and bicarbonate ($HCO_3^-$) ions. Say, the initial concentration of sodium bicarbonate is (B), $$NaHCO_3 \rightarrow Na^+(aq) + HCO_3^-(aq) \text{(Complete Dissociation)}$$

Subsequently, aqueous bicarbonate ions partially react (x) with water to form aqueous undissociated aqueous carbonic acid and hydroxyl ($OH^-$) ions.

$$HCO_3^-(aq) + H_2O \leftrightarrow H_2CO_3(aq) + OH^- \text{(Partial Dissociation)}$$

Now using the $pK_b$ and $K_b$ values ($pK_b = 14 - 6.35$), we create an equilibrium equation or relationship, $$(pK_b = 14.00 - pK_a 14.00 - 6.35 = 7.65)$$

$$K_b = 10^{-7.65} = 2.24 * 10^{-6}$$

Which is given by the following equation:

$$K_b = 10^{-7.65} = 2.24 * 10^{-6} = x*x/(B-x)$$

Solving for the above equation, we could get different hydroxyl ion concentration depending on the initial concentration of sodium bicarbonate (as shown in Table 1). The negative logarithm of hydroxyl ($OH^-$) ion concentration is pOH. Therefore, the pH of the solution is given by the following:

$$pH = pK_w - pOH \text{ (is presented in Table 1 for different ion concentrations).}$$

Example 2

Sodium acetate is dissolved in water and completely dissociates into aqueous sodium ($Na^+$) and acetate ($CH_3COO^-$) ions. Say, the initial concentration of sodium lactate is (A).

$$CH_3COONa(aq) \rightarrow Na^+(aq) + CH_3COO^-(aq) \text{(Complete Dissociation)}$$

Subsequently, aqueous lactate ions partially react (x) with water to form aqueous undissociated aqueous acetic acid and hydroxyl ($OH^-$) ions.

$$CH_3CHCOO^-(aq) + H_2O \leftrightarrow CH_3CHCOOH(aq) + OH^-(aq) \text{(Partial Dissociation)}$$

Now using the $pK_b$ and $K_b$ values ($pK_b = 14 - 4.76$) of acetic acid, we are going to create an equilibrium equation or relationship, $$(pK_b = 14.00 - pK_a = 14.00 - 4.76 = 9.24)$$

$$K_b = 10^{-9.24} = 5.75 * 10^{-10}$$

Which is given by the following equation:

$$K_b = 10^{-11.14} = 5.75 * 10^{-10} = x*x/(L-x)$$

Solving for the above equation, we get we could get different hydroxyl ion concentration depending on the initial concentration of sodium lactate. The negative logarithm of hydroxyl ($OH^-$) ion concentration is pOH. Therefore, the pH of the solution is given by the following:

$$pH = pK_w - pOH @ 25° C.$$

$$pH = pK_w - pOH \text{ (is presented in Table 1 for different ion concentrations)}$$

Example 3

As sodium lactate is dissolved in water, it completely dissociates into aqueous sodium ($Na^+$) and lactate ($CH_3CHCOO^-$) ions. Say, the initial concentration of sodium lactate is (L).

$$CH_3CHCOONa(aq) \rightarrow Na^+(aq) + CH_3CHCOO^-(aq) \text{(Complete Dissociation)}$$

Subsequently, aqueous lactate ions partially react (x) with water to form aqueous undissociated aqueous lactic acid and hydroxyl ($OH^-$) ions.

$$CH_3CHCOO^+(aq) + H_2O \leftrightarrow CH_3CHCOOH(aq) + OH^-(aq) \text{(Partial Dissociation)}$$

Now using the $pK_b$ and $K_b$ values ($pK_b = 3.86$) of lactic acid, we are going to create an equilibrium equation or relationship, $$(pK_b = 14.00 - pK_a = 14.00 - 3.86 = 11.14)$$

$$K_b = 10^{-11.14} = 7.24 * 10^{-12}$$

Which is given by the following equation:

$$K_b = 10^{-11.14} = 7.24 * 10^{-12} = x*x/(L-x)$$

Solving for the above equation, we get we could get different hydroxyl ion concentration depending on the initial concentration of sodium lactate. The negative logarithm of hydroxyl ($OH^-$) ion concentration is pOH. Therefore, the pH of the solution is given by the following:

$$pH = pK_w - pOH @ 25° C.$$

$$pH = pK_w - pOH \text{ (is presented in Table 1 for different ion concentrations).}$$

(Le Chatelier's principle could help prevent dissociation lactic acid dissociation) $CH_3CHCOOH \leftrightarrow H^+ + CH_3CHCOO^-$ (Acidosis from Lactic Acid metabolism)

Example 4

As trisodium citrate is dissolved in water, it completely dissociates into aqueous sodium ($Na^+$) and citrate ($C_6H_5O_7^{3-}$) ions. Say, the initial concentration of sodium citrate is (C). which is given by the following reaction:

$$C_6H_5O_7Na_3 \rightarrow C_6H_5O_7^{3-} + 3Na^+ \text{(Complete Dissociation)}$$

Subsequently, citrate ($C_6H_5O_7^{3-}$, $C_6H_5O_7H^{2-}$ and $C_6H_5O_7H^{2-}$) ions sequentially reacts water to eventually form aqueous undissociated aqueous citric acid and altogether three (3) hydroxyl ($OH^-$) ions for each citrate ion (with valency 3) resulting in pH between 7.5 and 9.0 in the solution.

The $pK_a$ values of citric acid are as follows: $pK_{a3} = 5.21$, $pK_{a2} = 4.28$ and $pK_{a1} = 2.92$ (Partial Dissociation)

$$C_6H_5O_7^{3-} + H_2O \leftrightarrow C_6H_5O_7H^{2-} + OH^-(aq) (pK_{b3} = 14.0 - 5.21 = 8.79)$$

$$C_6H_5O_7H^{2-} + H_2O \leftrightarrow C_6H_5O_7H^{2+} + OH^-(aq) (pK_{b2} = 14.0 - 4.28 = 9.72)$$

$$C_6H_5O_7H^{2+}H_2O \leftrightarrow C_6H_5O_7H^{3+} + OH^-(aq) (pK_{b1} = 14.0 - 2.92 = 11.08)$$

Trisodium citrate ($C_6H_5O_7Na_3$) has Mol. Wt. 258.068 g/mol. Trisodium Citrate is the sodium salt of citrate with alkalinizing capability too. After dissolving in water, trisodium citrate dissociates into sodium ($Na^+$) cations and citrate ($C_6H_5O_7^{3-}$) anions. It should be noted that organic citrate ions are also metabolized to bicarbonate ions, resulting in an increase in the plasma bicarbonate concentration, the buffering of excess hydrogen ion, thus raising the pH of blood, and potentially the reversal of acidosis.

The pH of sodium citrate varies between 7.5 and 9.0 (for concentration 5% aqueous solution, i.e., 50 gm/L~0.1937 Eq/L)

Note: The pH of sodium acetate and other sodium salts of weak organic acids in water (or gel mixture formulation) would slowly decrease over time due to the dissolution of atmospheric $CO_2$ via diffusion when the gel mixture Formulations (I and II) are created above 7.0. Shelf Life of the Formulation I and II may be marginally compromised due to very slow infiltration of atmospheric $CO_2$ in the bottled gel mixture formulations.

Example 5

Preparation of Exemplary Formulation (I)

An exemplary Formulation (I) is prepared by first transferring 1.0 liter of deionized water in a 2-liter Erlenmeyer flask and cap it with cotton wool. Place the Erlenmeyer flask in an autoclave to sterilize the DI water at 125° C. for more than 15 minutes. Allow the autoclave to cool down to lower the pressure to normal atmospheric pressure and then open the autoclave lid while wearing thermally insulated gloves (appropriate safety measures) and other personal protective equipment (e.g., safety glass etc.). Bring the Erlenmeyer flask containing sterilized water out of the autoclave. Place the Erlenmeyer flask in UV radiation chamber and irradiate the water filled Erlenmeyer flask. Bring out the Erlenmeyer flask and remove its cotton wool cap. Transfer the steam sterilized Erlenmeyer flask over a magnetically stirred hot plate and continue to maintain 50° C. temperature inside the flask.

Then, weigh 3.78 g of pharmaceutical grade sodium bicarbonate ($NaHCO_3$) on a watch glass. Add this measured amount of sodium bicarbonate ($NaHCO_3$) into the Erlenmeyer flask and turn on the magnetic stirrer for continued mixing and maintain 50° C. temperature until dissolved. Weigh 350.00 g of pharmaceutical grade sodium chloride (NaCl) on a watch glass. Transfer the measured amount of sodium chloride (NaCl) into the Erlenmeyer flask and continue with the mixing over a magnetically stirred hot plate and maintain 50° C. temperature until dissolved. Weigh 25.00 g of pharmaceutical grade sodium lactate ($C_3H_5NaO_3$) on a watch glass. Transfer the measured amount of sodium lactate ($C_3H_5NaO_3$) into the Erlenmeyer flask and continue with the mixing over a magnetically stirred hot plate and maintain 50° C. temperature until dissolved. Remove the magnets from Erlenmeyer flask and place a high-speed mixer with a double impeller blade arrangement (e.g., NovAspestic high-speed mixer) inside the Erlenmeyer flask. Turn on the mixer and maintain at least 1000 rpm speed while ensuring that air does not become entrained into the solution. Transfer the solution containing dissolved sodium bicarbonate, sodium lactate and sodium chloride in a beaker. Continue to maintain higher temperature inside a (1.5-2.0) liter beaker which is also placed over a hot plate.

Then weigh 40 g of pharmaceutical grade hydroxyethyl cellulose on a watch glass. Transfer the weighed hydroxyethyl cellulose slowly into the beaker and continue with the mixing for minimum of 30 minutes over the hot plate while maintaining 50° C. temperature at 4000 rpm speed for 30 minutes or until dissolved. If required increase the rpm of the mixer to speed up the complete dissolution of hydroxyethyl cellulose in water without entraining air. Take a sample of the mixer to determine the viscosity of the mixture at 25° C. Once the viscosity reaches between 1000-150,000 cp stop the mixing. If the viscosity is below 1000 cp, add small amount of hydroxyethyl cellulose and repeat steps 21 and 22. Place the beaker in water bath and continue mixing until the temperature reaches 25° C. Use a pH probe in the mixer to determine the pH of the mixture at 25° C. If the pH reaches 7.8-9 range, stop mixing and bottle the mixture, else add additional sodium bicarbonate until the pH of the mixture reaches 7.8-9 range. The order of addition of ingredients may be changed to facilitate dissolution time.

Example 6

Preparation of Formulation (II)

An exemplary Formulation (II) is prepared by first transferring 1 liter of deionized water in a 2 liter Erlenmeyer flask and cap it with cotton wool. Place the Erlenmeyer flask in an autoclave to sterilize the DI water at 125° C. for more than 15 minutes. Allow the autoclave to cool down to lower the pressure to normal atmospheric pressure and then open the autoclave lid while wearing thermally insulated gloves (appropriate safety measures) and other personal protective equipment (e.g., safety glass etc.). Bring the Erlenmeyer flask containing sterilized water out of the autoclave. Place the Erlenmeyer flask in UV radiation chamber and irradiate the water filled Erlenmeyer flask. Bring out the Erlenmeyer flask from UV irradiation chamber and remove its cotton wool cap. Transfer the steam sterilized Erlenmeyer flask over a magnetically stirred hot plate and continue to maintain 50° C. temperature inside the flask.

Weigh pharmaceutical grade sodium bicarbonate ($NaHCO_3$) on a watch glass. Add the measured amount of sodium bicarbonate ($NaHCO_3$) into the Erlenmeyer flask and turn on the magnetic stirrer for continued mixing and maintain 50° C. temperature until dissolved. Weigh of pharmaceutical grade sodium chloride (NaCl) on a watch glass. Transfer the measured amount of sodium chloride (NaCl) into the Erlenmeyer flask and continue with the mixing over a magnetically stirred hot plate and maintain 50° C. temperature until dissolved. Weigh of pharmaceutical grade sodium lactate ($C_3H_5NaO_3$) on a watch glass. Transfer the measured amount of sodium lactate ($C_3H_5NaO_3$) into the Erlenmeyer flask and continue with the mixing over a magnetically stirred hot plate and maintain 50° C. temperature until dissolved. Then remove the magnets from Erlenmeyer flask and place a high-speed mixer with a double impeller blade arrangement (e.g., NovAspestic high-speed mixer) inside the Erlenmeyer flask. Turn on the mixer and maintain at least 1000 rpm speed while ensuring that air doesn't get entrained into the solution. Transfer the solution containing dissolved sodium bicarbonate, sodium lactate and sodium chloride in a (1.5-2.0) liter beaker. Continue to maintain higher temperature inside a (1.5-2.0) liter beaker which is also placed over a hot plate and maintain at least 1000 rpm speed.

Then, weigh 40 gm of pharmaceutical grade hydroxyethyl cellulose on a watch glass. Transfer the weighed hydroxyethyl cellulose slowly into the beaker and continue with the mixing for minimum of 30 minutes over the hot plate while maintaining 50° C. temperature and continuously increase the speed to 4000 rpm speed or more for 30 minutes or until dissolved. If required increase the rpm of the mixer to speed up the complete dissolution of hydroxyethyl cellulose in water without entraining air. To enhance better dissolution of hydroxyethyl cellulose in water, bring down the temperature of the mixture by stopping the heat. After complete dissolution of hydroxyethyl cellulose, take a sample from the mixer to determine the viscosity of the mixture at 25° C. Once the viscosity reaches between 1000-150,000 cp stop the mixing. If the viscosity is below 1000 cp, add small amount of hydroxyethyl cellulose and repeat steps 21 and 22. Place the beaker in water bath and continue mixing until the temperature reaches 25° C. Use a pH probe in the mixer to determine the pH of the mixture at 25° C. Now slowly add small amount of lactic acid to the mixture while vigorously stirring and wait 30 minutes to allow complete mixing and simultaneously take the pH reading at 25° C. If the pH reaches 7.01-7.2 range, stop mixing and bottle the mixture, else add additional lactic acid until the pH of the mixture reaches 7.01-7.2.

Example 7

Various non-limiting examples of Formulations (I) and (II) that are prepared according to Examples 5 or 6, or according to other embodiments of this disclosure, are provided in tabular form in FIGS. 21-26.

Example 8

Figure 27:
FIG. 27: Picture showing the condition of burn injured area after the application of modified Formulation (I) over burn injured area and its vicinities at the onset of the injury showing no blister formation (Picture taken after 4 days).

FIG. 27 shows a small burn area injury on the backside of an injured patient's left palm where a gel formulation was applied within a minute of the injury. During this incident, while frying chicken over a saucepan, a table spoon of boiling hot butter splashed (as residual water from chicken suddenly became vaporized) on the backside of patient's palm. Immediately, the patient was engulfed with excruciating pain around burn injured areas and its vicinities. The hot butter eventually flowed down towards left index finger and also caused burning sensation too due to the fact that finger tips are relatively more sensitive.

With quick reflex action, the patient immediately applied a gel formulation on the burn injured areas and its vicinities within a minute. A few minutes later, after the application of the formulation, slightly faint reddish color appeared on the upper part of the index finger which was very difficult to discern with naked eye. After the application of the gel formulation, the pain rapidly started to subside. After 20 minutes or so, 95% of the pain receded and was almost gone after 45 minutes with no appearance of blister formation. Next morning, the patient became oblivious to previous day's injury. After few days, the patient noticed dead skin appearing (See FIG. 27) on the burnt areas on the back side of the palm on the burnt areas with no blister. The picture (See FIG. 27) was taken five days after the burn injury.

Since the area was burn injury was less than 10% of TBSA, there was minimal metabolic acidosis (less lactic acid dissociation) and accordingly, modified Formulation (I) was used on the burn injured areas. The composition of this formulation comprised of 340 g/Liter sodium chloride (NaCl) plus 3.8 mg/Liter sodium bicarbonate (NaHCO$_3$) with pH ~8.0 in the gel mixture formulation. This example provides ample evidence that the pain management and blister formation due to thermal burn injury can be avoided with the application of the gel formulation, if applied at the onset of burn injury.

Concise Statements Regarding the Formulations and their Use

Gel mixture Formulations (I and II) are applicable for thermal and electrical burn injuries. Gel mixture Formulations (I and II) are applicable for first and second degree burn injuries. Gel mixture Formulations (I and II) are applicable for external use only. Gel mixture Formulations (I and II) are applied only over unopened burn injured skin surface after removing jewelry, clothes, watch etc. Gel mixture Formulation (I) should be applied from the onset of the burn shock injury. Once applied from the onset of the burn shock injury, it would minimize blister formation, hyponatremia, initial acidosis, hyperkalemia followed by subsequent alkalosis. Once Formulations (I) are applied from the onset of the burn shock injury, it would minimize blister formation and their proliferation.

As a result of burn shock, this gel mixture Formulations (I and II) are applied in vitro for controlling hyperkalemia ($K^+ \geq 5.5$ mEq/L), hyponatremia ($Na^+ \leq 135$ mEq/L), initial acidosis and subsequent alkalosis in extracellular, edema, blister and intravascular fluids by sodium ($Na^+$) ion pump and counter anions of sodium ($Na^+$) ions, viz., bicarbonate ($HCO_3^-$), ($CH_3COO^-$), citrate, hydroxyl ($OH^-$) ions by diffusion with counter diffusional ion transport of potassium ($K^+$), through the transdermal route.

Gel mixture Formulations (I and II) are first aid treatment that should be made available in areas (such as kitchen, industrial settings, steam rooms, boilers etc.) where there are probable chances for burn injuries. Gel mixture Formulations (I and II) could be made available in ambulances too. Gel mixture Formulations (I and II) could be placed inside a specially built bed for immersing burn patients for treatment with large burn areas. Gel mixture Formulations (I and II) should have gel type matrix with high viscosity (100-150,000 cPs at 20° C.). The gel type matrix should be prepared with sterile and DI water by mixing biodegradable and natural biopolymer and/or mixed with non-crosslinked organic polymers (polyacrylic acid or sodium polyacrylate, combinedly ≤300 mg/L and less). The viscosity of the mixture is maintained as such that when applied over skin it resist flow as it remains immobilized and/or barely flow over the skin layer to maintain ion transport across the transdermal route.

Non-crosslinked polyacrylic acid, non-crosslinked sodium polyacrylate, non-crosslinked strong cation ($Na^+$) exchange polymers, polyethylene glycol, and/or other biodegradable water-soluble biopolymers, such as hexose sugar derivatives including cellulose (glucose) oligomers/polymers, hexose sugar oligomers/polymers, pentose sugar oligomers/polymers, e.g., pectin, guar gum, gum arabic, cellulose derivatives, e.g., carboxymethyl cellulose (CMC), hexaethyl cellulose (HEC) and sodium substituted derivatives etc. dissolved in water could be used as base for the gel matrix or gel substrate formulation(s). The biopolymers should be biocompatible, non-crosslinked and should not be allergic to any patient. It should not be applied to patients with allergic reactions to the ingredients of the formulation mixtures. The gel mixture/matrix Formulations (I and II) may contain pain relieving medications.

The polydispersity index of the biopolymers could be PDI≥1 (PDI=$M_w/M_n$).

For best results, the gel mixture Formulations (I and II) with pH control components, should be applied at the onset of the burn injury without applying any other pretreatment, viz., cold water or ice before or after the thermal or electrical burn injuries. This mixture or formulation should be applied on the damaged (not over punctured or ruptured blisters or open wounds) bare skin surface and its vicinities between room temperature and avg. ~37° C., preferably above room temperature (25° C.) and below body temperature (37° ° C.) to prevent any hypothermia or drop in the body temperature (due to heat/fluid loss). This mixture or formulation should not be applied over punctured or ruptured blistered skin due to burn injury to avoid any stinging type pain and also causing hypernatremia because of the presence of salts in the mixture formulation. This mixture or formulation should be profusely applied to unopened burn areas and its vicinities. This mixture or formulation should not be applied over peeled skin from any injury.

This mixture acts as sodium and other ion(s) reservoir to pump sodium ($Na^+$) ion and other ions to rapidly enhance and maintain transport of ions across the exterior of the outer skin membrane and expel potassium ($K^+$) ions from the interior of the skin layer across the transdermal route into the gel mixture formulation (in vitro) to minimize fallout from the ion imbalances to undertake the earliest initiatives towards rectifying electrophysiological trauma while minimizing transcapillary leak (from blood vessels) during inflammatory and diuretic phase of the burn injury.

This mixture specifically pumps as sodium ($Na^+$) ions, components of sodium ($Na^+$) ion containing buffers or pH control ingredients, including bicarbonate ($HCO_3$), acetate ($CH_3COO^-$), lactate ion ($CH_3CHCOO^-$), citrate, hydroxyl ($OH^-$) ions in various combinations from its gel matrix reservoir while maintaining concentration gradient by recurring replacement of the Formulations I or II on the unopened injured skin surfaces to maintain pumping of the ($Na^+$) and other ions for their transport from the exterior of the skin layer (in vitro) to the interior fluids (in vivo) to minimize initial acidosis through the transdermal route.

The pH of the gel mixture Formulation (I) are maintained (up to pH~10.0) by dissolving any sodium ($Na^+$) ion containing buffers or pH control ingredients, including, sodium bicarbonate in ($NaHCO_3$) and/or other pH-controlled components to minimize initial acidosis as well as preventing SID from getting imbalanced. Sodium lactate (Le Chatelier's principle) etc. could be also be used a pH-controlled component along with $NaHCO_3$ or other sodium salt in the gel mixture Formulation (I) to rectify the initial metabolic acidosis as a result from lactic acid dissociation in extracellular fluid; this dissociation forces lowering of pH below 7.35 in plasma/extracellular fluid resulting in initial acidosis. Simultaneously, the lactate anions from sodium salt also help resist the pH imbalance and SID contraction in extracellular/plasma fluid. The pH of the gel mixture Formulation (II) are maintained between ($7.01 \leq pH \leq 7.3$) by dissolving sodium salt of weak organic acids, viz., sodium lactate and sodium citrate or weak acids to minimize subsequent alkalosis as well as to prevent SID getting imbalanced. The combined biodegradable gel mixture formulations (I and II)) also acts as a dissolved viscosity enhancer that resist flow and remain mostly immobilized after its application on the unopened burn injured skin surface.

Gel mixture Formulation (I) is also especially applicable for total large area burns (TBSA≥10-20%) at the onset of the burn injury to minimize blister/edema/vascular fluid loss. For the large area burn, the gel mixture Formulation (I) should be used as a first response to minimize burn after shock, however, Formulation (II) is applied if the initial response gets delayed, or applied after one hour of the application of Formulation (I) and also for patients with preexisting hyperkalemia. For best results, gel mixture Formulation (I) should be immediately applied to help expel the released highly concentrated potassium ($K^+$) ions; as a result of cell lysis, tissue necrosis, initial acidosis (from respiratory, metabolic and hyperchloremic) leading to subsequent alkalosis to prevent overall hyperkalemia ($K^+ \geq 5.5$ mEq/L) in the vast and intricate network of the circulatory system.

Gel mixture Formulation (I) should be used as the first line of defense as a means for resuscitation to normal homeostasis condition of burn injured victims as prehospital care. After the application of gel mixture Formulation (I), restoration the ion imbalances in the extracellular/blister/plasma fluid, like other cells, the nerve cells also rectify its action potentials, thus the pain near the burn injured areas gets relieved. This treatment is applicable for preventing or minimizing any changes in normal homeostasis (both ion and pH imbalances) or rapidly restoring the normal homeostasis if applied right from the beginning, i.e., from the onset of burn shock.

This initial application of this gel mixture Formulation (I) would reduce vasodilation of blood vessels; thereby preventing or minimizing transcapillary permeability, resulting in reducing both extracellular and cellular edema; and thus preventing excessive blister fluid accumulation when sodium ($Na^+$) ion and pH control components/ingredients from the gel mixture formulation(s) are pumped immediately on the onset of the burn shock (preferably within the first minute) through the transdermal route.

The source of potassium ($K^+$) is from cell lysis and assortment of acidosis that causes large fractions of the potassium ($K^+$) ions to enter into extracellular and/or interstitial and/or blister fluids from intracellular compartments thereby elevating the local concentration of potassium ($K^+$) ion and disrupting the normal homeostasis condition which is followed by subsequent alkalosis with ensuing pH level elevation.

As the acidosis is prevented, after the external application of gel mixture Formulation (I), part of the potassium ($K^+$) ions are expected to go back to healthy intracellular compartments or may not get released as such that one avenues of potassium ($K^+$) ion expulsion from healthy cells are minimized; if not, they too find the much shorter transdermal route for their expulsion via counter diffusion just like the released potassium ($K^+$) ions from cell lysis and tissue necrosis as the applied gel mixture formulation (in vitro) acts as (in vitro) ion sink for potassium ($K^+$) ions.

With early expulsion of potassium ($K^+$) ions due to the initial application with periodic replacement of gel mixture Formulation (I) at the onset of burn shock is expected to minimize/prevent acute tubular necrosis at later stages of the burn shock. Expulsion of excess potassium ($K^+$) ions from blister/edema fluid (which results from hyperkalemia due to cell lysis, tissue, necrosis, subsequent alkalosis etc.) outside the skin via diffusion helps minimize cardiogenic shock or cardiac and renal failures after potassium ($K^+$) ions are expelled, which in turn helps keep the overall potassium ($K^+$) ion concentration (within $3.5 \leq K^+ 55.5$ mEq/L) in the extracellular/plasma fluid. This normalizes/rectifies the action potentials and resting membrane potentials of most of the cells (nerve, skeletal, pacemaker, myocardial, renal tissues, etc.).

Application of gel mixture Formulation (preferentially I) is rectifies hyponatremia ($Na^+ \leq 135$ mEq/L) in blister/edema/extracellular/fluid in situ, after it is applied at the onset of burn injuries, thus raising the $Na^+$ ion concentration in extracellular and plasma fluid and thus causing most types of cells to reach right/optimal concentration ($135 \leq Na^+ \leq 145$) ion as such that the nerve, skeletal, pace maker and myocardial cells are able to coordinate their action potentials during depolarization phase. Thus, the application of this treatment rectifies the action potentials across most types of cell membranes by rectifying the homeostasis ions and pH imbalance.

The gel mixture Formulation (I) should be made available as a first aid treatment or as a first responder. This application of Formulation (I) is most effective when applied at the onset (first minutes) of burn shock. For severe burn (≥10-20% or more), this mixture is periodically replaced with fresh mixture in every (2-5) minutes to maintain rapid $K^+$ ion removal in situ, as such that the gel mixture does not allow the concentration gradient of $K^+$ ion across the membrane becoming smaller in magnitude. This procedure should be continued until pain and blister management is controlled successfully or until the arrival of the patients in the burn units or hospitals. The immediate (within a minute) application of this gel mixture Formulation (I) right after the thermal burn injury on the affected area is required for delaying and/or minimizing blister formation from the burn injuries. The immediate applications of this gel mixture Formulation (I) right after the thermal burn injury on the affected area is required for gradual and faster pain relief as a result of burn shock by rectifying the ion imbalances in situ across the nerve cell membranes. The initial application of this gel mixture Formulations (I and II) would reduce the need for large volumes of resuscitation fluid; which would minimize the increased risk of complications, viz., acute respiratory distress syndrome (ARDS), abdominal compartment syndrome and/or death.

I claim:

1. A gel formulation consisting of, per liter of the gel formulation at 25° C.:
   from 80 g to 340 g sodium chloride;
   from $6\times10^{-5}$ g to 42 g sodium bicarbonate;
   from $1.0\times10^{-6}$ g to 1.3 g sodium carbonate;
   from $1.6\times10^{-2}$ g to 156 g sodium lactate;
   from $1.53\times10^{-3}$ g to 82 g sodium acetate;
   from 0.198 g to 420 g trisodium citrate;
   a gelling agent selected from the group consisting of hydroxyethyl cellulose, oligomers of cellulose, pectin, carboxymethyl cellulose, guar gum, gum Arabic, and mixtures thereof; and
   water from a sterilized and deionized source,
   wherein the gel formulation contains only pharmaceutical grade ingredients and has:
   a total sodium-ion concentration greater than or equal to 154 g/L;
   a total bicarbonate-ion concentration from $4.4\times10^{-5}$ g/L to 30.49 g/L;
   a pH from 7.01 to 10.00;
   a yield point of greater than or equal to 1000 poise; and
   an apparent viscosity from greater than 100 centipoise to 150,000 centipoise.

2. The gel formulation of claim 1, wherein all salts present in the gel formulation are sodium salts and the gel formulation does not contain any potassium salts or potassium ions.

3. The gel formulation of claim 1, wherein all salts of the gel formulation are completely dissolved in a gel matrix of the gelling agent and the water.

4. A method for mitigating a burn injury to a burn victim using a gel formulation according to claim 1, the method comprising:
   applying the gel formulation within 10 minutes of a burn injury on injured skin of the burn victim;
   spreading the applied gel formulation on the injured skin to prevent loss of vascular fluid into extracellular regions, to expedite in situ sodium-ion transfer across transdermal membranes in vivo, to in situ expel potassium ions across the transdermal membranes in vitro, and to prevent blister formation or proliferation; and
   reapplying fresh gel formulation on the injured skin to maintain high sodium ion concentration gradient across transdermal membranes in vitro to in vivo and high potassium ion concentration gradient across the transdermal membranes in vivo to in vitro.

5. The method of claim 4, wherein all salts present in the gel formulation are sodium salts and the gel formulation does not contain any potassium salts or potassium ions.

* * * * *